(12) United States Patent
Ramachandran et al.

(10) Patent No.: US 12,287,342 B2
(45) Date of Patent: *Apr. 29, 2025

(54) BIOMARKERS FOR DIAGNOSING NON-ALCOHOLIC STEATOHEPATITIS (NASH) OR HEPATOCELLULAR CARCINOMA (HCC)

(71) Applicant: Venn Biosciences Corporation, South San Francisco, CA (US)

(72) Inventors: Prasanna Ramachandran, Menlo Park, CA (US); Gege Xu, Redwood City, CA (US)

(73) Assignee: Venn Biosciences Corporation, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/454,159

(22) Filed: Aug. 23, 2023

(65) Prior Publication Data
US 2024/0118290 A1 Apr. 11, 2024

Related U.S. Application Data

(63) Continuation of application No. 17/535,018, filed on Nov. 24, 2021, now Pat. No. 11,774,459.
(Continued)

(51) Int. Cl.
*G01N 33/68* (2006.01)
*G01N 30/72* (2006.01)
(Continued)

(52) U.S. Cl.
CPC ..... *G01N 33/6893* (2013.01); *G01N 30/7233* (2013.01); *G01N 33/6848* (2013.01);
(Continued)

(58) Field of Classification Search
None
See application file for complete search history.

(56) References Cited

U.S. PATENT DOCUMENTS

2007/0099251 A1   5/2007   Zhang et al.
2015/0219672 A1   8/2015   Meno et al.
(Continued)

OTHER PUBLICATIONS

Sorino, P et al. Selecting the best machine learning algorithm to support the diagnosis of Non-Alcoholic Fatty Liver Disease: A meta learner study. *PLoS One*. Oct. 20, 2020, vol. 15, No. 10; pp. 1-12.
(Continued)

*Primary Examiner* — Xiaoyun R Xu
(74) *Attorney, Agent, or Firm* — MEDLER FERRO WOODHOUSE & MILLS PLLC

(57) ABSTRACT

Embodiments described herein generally relate to technologies for analyzing peptide structures for diagnosing and/or treating a disease state advancing through a disease progression. A non-limiting example of a method relating to the technologies described in the subject application may include receiving peptide structure data corresponding to the biological sample obtained from the subject, identifying a peptide structure profile, and diagnosing a disease state within a disease progression. The example may further include generating a diagnosis output relating to the disease state. In at least some cases, the peptide structure profile may include glycosylated peptides, aglycosylated peptides, or both.

19 Claims, 30 Drawing Sheets
Specification includes a Sequence Listing.

Related U.S. Application Data

(60) Provisional application No. 63/251,021, filed on Sep. 30, 2021, provisional application No. 63/118,486, filed on Nov. 25, 2020.

(51) Int. Cl.
   *G06N 3/08* (2023.01)
   *G16B 20/00* (2019.01)
   *G16B 40/20* (2019.01)
   *G01N 30/02* (2006.01)

(52) U.S. Cl.
   CPC ............... *G06N 3/08* (2013.01); *G16B 20/00* (2019.02); *G16B 40/20* (2019.02); *G01N 2030/027* (2013.01); *G01N 2440/38* (2013.01); *G01N 2800/085* (2013.01)

(56) References Cited

U.S. PATENT DOCUMENTS

| | | |
|---|---|---|
| 2019/0101544 A1 | 4/2019 | Danan-Leon et al. |
| 2020/0137273 A1 | 4/2020 | Ding et al. |
| 2020/0240996 A1 | 7/2020 | Danan-Leon et al. |

OTHER PUBLICATIONS

International Search Report and Written Opinion issued in corresponding International application PCT/US21/60776 mailed Jun. 24, 2022.

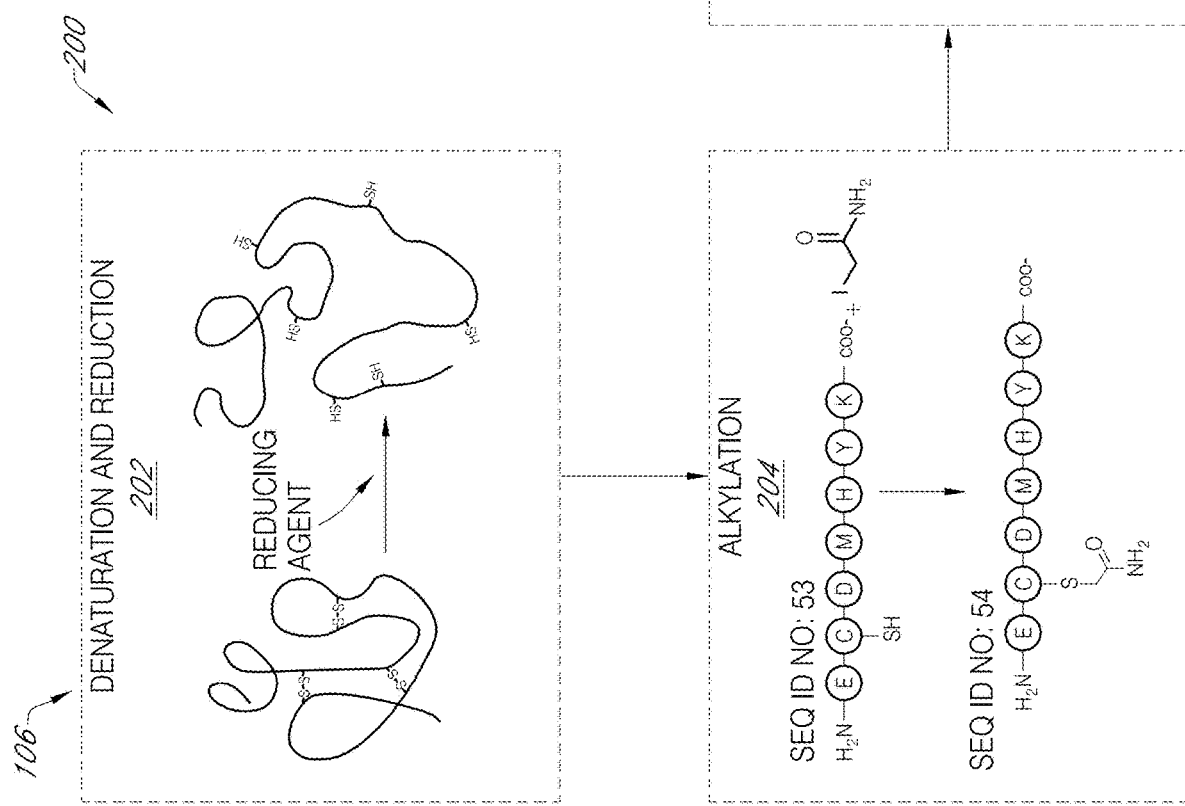

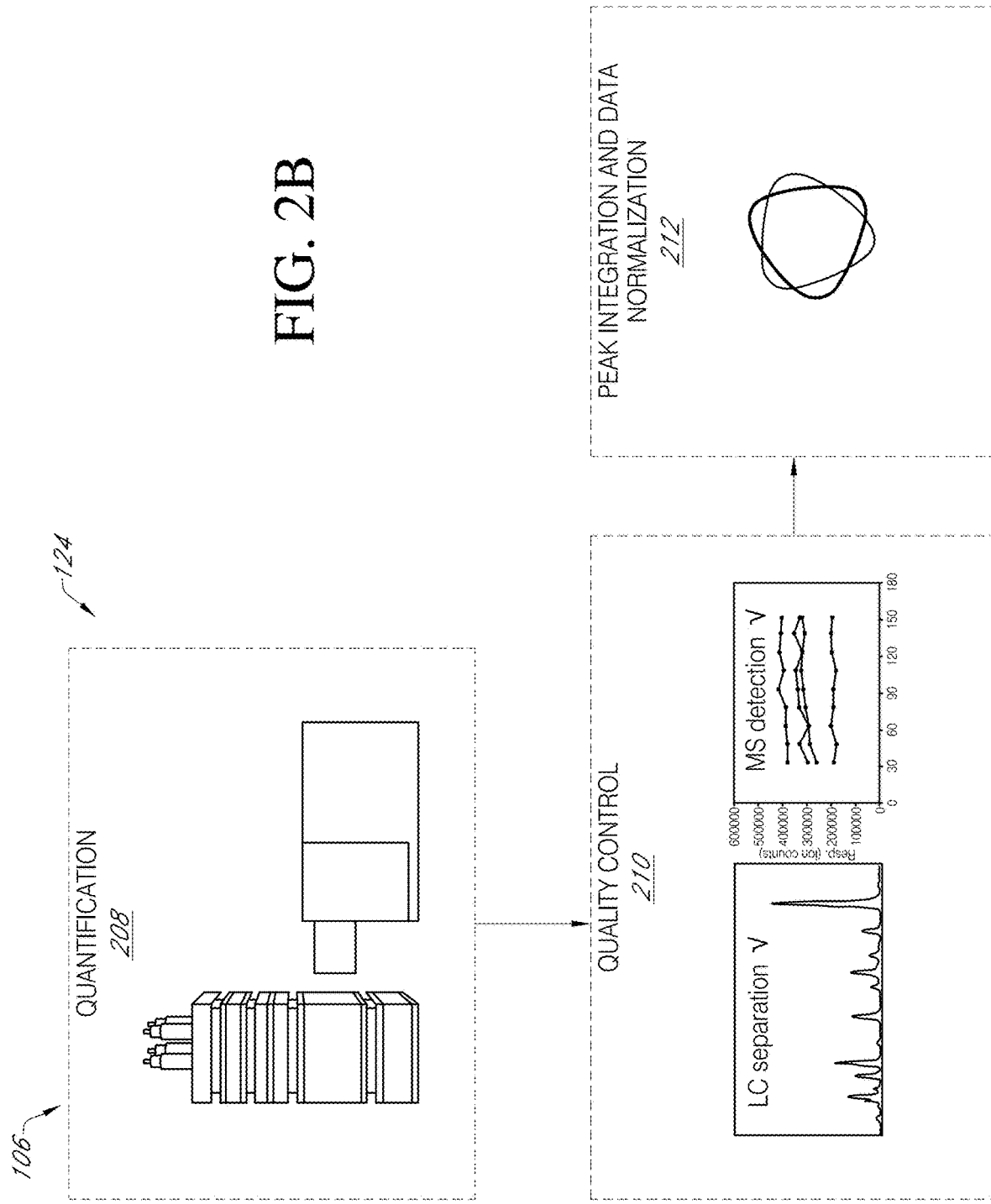

| | Number of subjects | Male | Female |
|---|---|---|---|
| Control | 56 | 26 | 30 |
| NASH | 23 | 10 | 13 |
| HCC | 20 | 16 | 4 |

FIG. 11

| Control (liver-benign) | Number of subjects | Male/Female |
|---|---|---|
| | 28 | 16/12 |
| HCC | 28 | 20/8 |

FIG. 12

FIG. 23A
| Glycan Structure GL NO. | Structure | Composition |
|---|---|---|
| 1102 | 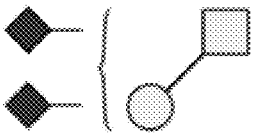 | Hex(1)HexNAc(1)Fuc(0)NeuAc(2) |
| 1202 | 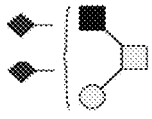 | Hex(1)HexNAc(2)Fuc(0)NeuAc(2) |
| 1300 | 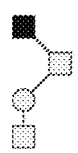 | Hex(1)HexNAc(3)Fuc(0)NeuAc(0) |
| 2110 | 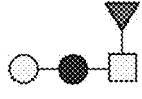 | Hex(2)HexNAc(1)Fuc(1)NeuAc(0) |
| 4400 | 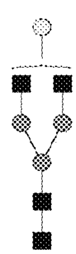 | Hex(4)HexNAc(4)Fuc(0)NeuAc(0) |
| 4411 | 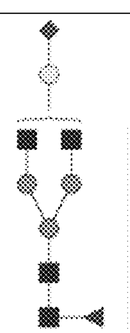 | Hex(4)HexNAc(4)Fuc(1)NeuAc(1) |

FIG. 23B
| | | |
|---|---|---|
| 5200 | 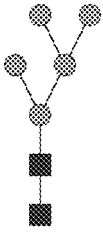 | Hex(5)HexNAc(2)Fuc(0)NeuAc(0) |
| 5400 | 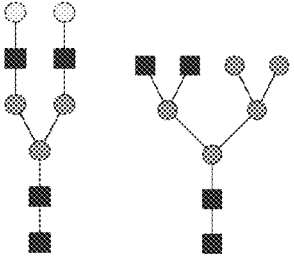 | Hex(5)HexNAc(4)Fuc(0)NeuAc(0) |
| 5401 | 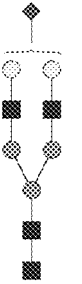 | Hex(5)HexNAc(4)Fuc(0)NeuAc(1) |
| 5402 | 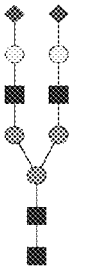 | Hex(5)HexNAc(4)Fuc(0)NeuAc(2) |
| 5410 | 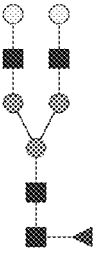 | Hex(5)HexNAc(4)Fuc(1)NeuAc(0) |

FIG. 23C

| | | |
|---|---|---|
| 5411 | | Hex(5)HexNAc(4)Fuc(1)NeuAc(1) |
| 5412 | | Hex(5)HexNAc(4)Fuc(1)NeuAc(2) |
| 5421 | | Hex(5)HexNAc(4)Fuc(2)NeuAc(1) |
| 5431 | | Hex(5)HexNAc(4)Fuc(3)NeuAc(1) |
| 5510 | | Hex(5)HexNAc(5)Fuc(1)NeuAc(0) |

FIG. 23D
| | | |
|---|---|---|
| 5511 | 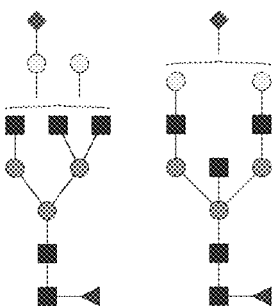 | Hex(5)HexNAc(5)Fuc(1)NeuAc(1) |
| 6200 | 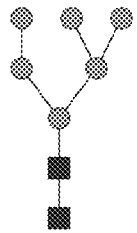 | Hex(6)HexNAc(2)Fuc(0)NeuAc(0) |
| 6300 | 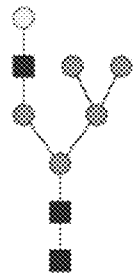 | Hex(6)HexNAc(3)Fuc(0)NeuAc(0) |
| 6501 | 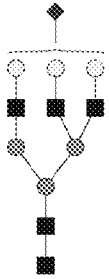 | Hex(6)HexNAc(5)Fuc(0)NeuAc(1) |
| 6502 | 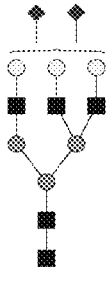 | Hex(6)HexNAc(5)Fuc(0)NeuAc(2) |

FIG. 23E

| | | |
|---|---|---|
| 6503 | | Hex(6)HexNAc(5)Fuc(0)NeuAc(3) |
| 6512 | | Hex(6)HexNAc(5)Fuc(1)NeuAc(2) |
| 6513 | | Hex(6)HexNAc(5)Fuc(1)NeuAc(3) |
| 7601 | | Hex(7)HexNAc(6)Fuc(0)NeuAc(1) |
| 7604 | | Hex(7)HexNAc(6)Fuc(0)NeuAc(4) |

FIG. 23F

| | | |
|---|---|---|
| 7613 | | Hex(7)HexNAc(6)Fuc(1)NeuAc(3) |
| 7614 | | Hex(7)HexNAc(6)Fuc(1)NeuAc(4) |
| 10803 | | Hex(5)HexNAc(4)Fuc(0)NeuAc(1)<br>+<br>Hex(5)HexNAc(4)Fuc(0)NeuAc(2) |
| 11904 | | Hex(5)HexNAc(4)Fuc(0)NeuAc(2)<br>+<br>Hex(6)HexNAc(5)Fuc(0)NeuAc(2) |
| 121005 | | Hex(6)HexNAc(5)Fuc(0)NeuAc(2)<br>+<br>Hex(6)HexNAc(5)Fuc(0)NeuAc(3) |
| 121015 | | Hex(6)HexNAc(5)Fuc(0)NeuAc(2)<br>+<br>Hex(7)HexNAc(6)Fuc(1)NeuAc(3) |

BIOMARKERS FOR DIAGNOSING NON-ALCOHOLIC STEATOHEPATITIS (NASH) OR HEPATOCELLULAR CARCINOMA (HCC)

FIELD

The present disclosure generally relates to methods and systems for diagnosing and/or treating a state of a fatty liver disease (FLD) progression. More particularly, the present disclosure relates to analyzing quantification data for a set of peptide structures detected in a biological sample obtained from a subject for use in a diagnostic assessment of the subject's disease state (e.g., healthy, NASH, HCC) relating to a disease progression and/or treating the subject.

SEQUENCE LISTING

The instant application contains a Sequence Listing which has been submitted via Patent Center and is hereby incorporated by reference in its entirety. Said.xml copy, created on Nov. 2, 2023 is named VENNP0005USC1, and is 104,093 bytes in size.

BACKGROUND

Protein glycosylation and other post-translational modifications play vital roles in virtually all aspects of human physiology. Unsurprisingly, faulty or altered protein glycosylation often accompanies various disease states. The identification of aberrant glycosylation provides opportunities for early detection, intervention, and treatment of affected subjects. Current biomarker identification methods, such as those developed in the fields of proteomics and genomics, can be used to detect indicators of certain diseases, such as cancer, and to differentiate certain types of cancer from other, non-cancerous diseases. However, the use of glycoproteomic analyses has not previously been used to successfully identify disease processes. Further, glycoproteomic analyses has not previously been used to successfully identify a disease state relating to a disease progression.

Glycoprotein analysis is fraught with challenges on several levels. For example, a single glycan composition in a peptide can contain a large number of isomeric structures due to different glycosidic linkages, branching patterns, and/or multiple monosaccharides having the same mass. In addition, the presence of multiple glycans that share the same peptide backbone can lead to assay signals from various glycoforms, lowering their individual abundances compared to aglycosylated peptides. Accordingly, the development of algorithms that can identify glycan structures on peptide fragments remains elusive.

In light of the above, there is a need for improved analytical methods that involve site-specific analysis of glycoproteins to obtain information about protein glycosylation patterns, which can in turn provide quantitative information that can be used to identify disease processes. The present disclosure addresses this and other needs by combining site-specific glycoprotein analysis with machine learning and advanced mass spectrometry instrumentation to quantitatively analyze peptide structures that are indicative of specific disease states, including, but not limited to, NASH and HCC.

Nonalcoholic fatty livery diseases (NAFLD or FLD) are byproducts of a global epidemic of obesity and metabolic syndrome. FLD progresses through stages of fat accumulation and inflammation to NASH, and a small percentage of NASH patients progress to HCC. Knowing an FLD stage of a patient with a high degree of accuracy would allow medical practitioners to customize treatment for individual patients and achieve better outcomes. The problem is that current diagnostic techniques have the accuracy necessary to definitively predict the stage of FLD (e.g. whether a patient just has fat accumulation, NASH, or HCC). Thus, it may be desirable to have methods and systems capable of distinguishing between these and healthy states.

SUMMARY

In one or more embodiments, a method is provided for classifying a biological sample with respect to a plurality of states associated with fatty liver disease (FLD) progression. The method includes receiving peptide structure data corresponding to a set of glycoproteins in the biological sample obtained from a subject. Quantification data identified from the peptide structure data for a set of peptide structures is input into a machine learning model. The set of peptide structures includes at least one peptide structure identified from a plurality of peptide structures in Table 1. The quantification data is analyzed using the machine learning model to generate a disease indicator. A diagnosis output is generated based on the disease indicator that classifies the biological sample as evidencing a corresponding state of the plurality of states associated with the FLD progression.

In one or more embodiments, a method is provided for training a model to diagnose a subject with one of a plurality of states associated with fatty liver disease (FLD) progression. The method includes receiving quantification data for a panel of peptide structures for a plurality of subjects diagnosed with the plurality of states associated with the FLD progression. The quantification data comprises a plurality of peptide structure profiles for the plurality of subjects and identifies a corresponding state of the plurality of states for each peptide structure profile of the plurality of peptide structure profiles. A machine learning model is trained using the quantification data to determine which state of the plurality of states a biological sample from a subject corresponds.

In one or more embodiments, a method is provided for detecting a presence of one of a plurality of states associated with fatty liver disease (FLD) progression in a biological sample. The method includes receiving peptide structure data corresponding to a set of glycoproteins in the biological sample obtained from a subject. The peptide structure data is analyzed using a supervised machine learning model to generate a disease indicator based on at least 3 peptide structures selected from a group of peptide structures identified in Table 1. The presence of a corresponding state of the plurality of states associated with the FLD progression is detected in response to a determination that the disease indicator falls within a selected range associated with the corresponding state.

In one or more embodiments, a method is provided for classifying a biological sample as corresponding to one of a plurality of states associated with fatty liver disease (FLD) progression. The method includes training a supervised machine learning model using training data. The training data comprises a plurality of peptide structure profiles for a plurality of training subjects and identifies a corresponding state of the plurality of states for each peptide structure profile of the plurality of peptide structure profiles. Peptide structure data corresponding to a set of glycoproteins in the biological sample obtained from a subject is received. Quantification data identified from the peptide structure data for a set of peptide structures is input into the supervised machine learning model that has been trained. The set of peptide structures includes at least one peptide structure identified in Table 1. The quantification data is analyzed using the supervised machine learning model to generate a score. A determination is made that the score falls within a selected range associated with a corresponding state of the plurality of states associated with the FLD progression. A diagnosis output is generated, where the diagnosis output indicates that the biological sample evidences the corresponding state. The plurality of states includes a non-alcoholic steatohepatitis (NASH) state, a hepatocellular carcinoma (HCC) state, and a non-NASH/HCC state.

In one or more embodiments, a method is provided for treating a non-alcoholic steatohepatitis (NASH) disorder in a patient to at least one of reduce, stall, or reverse a progression of the NASH disorder into hepatocellular carcinoma. The method includes receiving a biological sample from the patient. A quantity of each peptide structure identified in Table 1 in the biological sample i determined using MRM-MS. The quantity of each peptide structure is analyzed using a machine learning model to generate a disease indicator. A diagnosis output is generated based on the disease indicator that classifies the biological sample as evidencing that the patient has the NASH disorder. Obeticholic acid (OCA) or a derivative thereof is administered to the patient. The administering comprises at least one of intravenous or oral administration in a range of 10-25 mg daily.

In one or more embodiments, a method is provided for treating a hepatocellular carcinoma (HCC) disorder in a patient. The method includes receiving a biological sample from the patient. A quantity of each peptide structure identified in Table 1 in the biological sample is determined using MRM-MS. The quantity of each peptide structure is analyzed using a machine learning model to generate a disease indicator. A diagnosis output is generated based on the disease indicator that classifies the biological sample as evidencing that the patient has the HCC disorder. A treatment is administered, where the treatment includes at least one of: Sorafenib or a derivative thereof to the patient, the administering comprising at least one of intravenous or oral administration in a range of 775-825 mg daily; Lenvatinib or a derivative thereof to the patient, the administering comprising at least one of intravenous or oral administration in a range of 7.5-8.5 mg/day when the patient weighs <60 kg and 11.5-12.5 mg/day when the patient weighs >60 kg; Nivolumab or a derivative thereof to the patient, the administering comprising at least one of intravenous or oral administration in a range of 0.75-1.25 mg/kg; Regorafenib or a derivative thereof to the patient, the administering comprising oral administration in a range of 150-170 mg/day; Cabozantinib or a derivative thereof to the patient, the administering comprising at least one of intravenous or oral administration in a range of 50-70 mg/day; or Ramucirumab or a derivative thereof to the patient, the administering comprising at least one of intravenous or oral administration in a range of 8-12 mg/kg.

In one or more embodiments, a method is provided for designing a treatment for a subject diagnosed with a disease state associated with a fatty liver disease (FLD) progression. The method includes designing a therapeutic for treating the subject in response to determining that a biological sample obtained from the subject evidences the disease state using any one of the methods disclosed herein.

In one or more embodiments, a method is provided for planning a treatment for a subject diagnosed with a disease state associated with a fatty liver disease (FLD) progression, the method comprising generating a treatment plan for treating the subject in response to determining that a biological sample obtained from the subject evidences the disease state using any one of the methods disclosed herein.

In one or more embodiments, a method is provided for treating a subject diagnosed with a disease state associated with a fatty liver disease (FLD) progression, the method comprising administering to the subject a therapeutic to treat the subject based on determining that a biological sample obtained from the subject evidences the disease state using any one of the methods disclosed herein.

In one or more embodiments, a method is provided for treating a subject diagnosed with a disease state associated with a fatty liver disease (FLD) progression, the method comprising selecting a therapeutic to treat the subject based on determining that the subject is responsive to the therapeutic using any one of the methods disclosed herein.

In one or more embodiments, a method is provided for analyzing a set of peptide structures in a sample from a patient. The method includes (a) obtaining the sample from the patient; (b) preparing the sample to form a prepared sample comprising a set of peptide structures; (c) inputting the prepared sample into a reaction monitoring mass spectrometry system to detect a set of product ions associated with each peptide structure of the set of peptide structures; and (d) generating quantification data for the set of product ions using the reaction monitoring mass spectrometry system. The set of peptide structures includes at least one peptide structure selected from peptide structures PS-1 to PS-53 identified in Table 4. The set of peptide structures includes a peptide structure that is characterized as having: (i) a precursor ion with a mass-charge (m/z) ratio within ±1.5 of the m/z ratio listed for the precursor ion in Table 4 as corresponding to the peptide structure; and (ii) a product ion having an m/z ratio within ±1.0 of the m/z ratio listed for the first product ion in Table 4 as corresponding to the peptide structure In one or more embodiments, a composition is provided, the composition comprising at least one of peptide structures PS-1 to PS-53 identified in Table 1.

In one or more embodiments, a composition is provided, the composition comprising a peptide structure or a product ion. The peptide structure or product ion comprises an amino acid sequence having at least 90% sequence identity to any one of SEQ ID NOS: 23-51, corresponding to peptide structures PS-1 to PS-53 in Table 1. The product ion is selected as one from a group consisting of product ions identified in Table 4 including product ions falling within an identified m/z range.

In one or more embodiments, a composition is provided, the composition comprising a glycopeptide structure selected as one from a group consisting of peptide structures PS-1 to PS-53 identified in Table 4. The glycopeptide structure comprises an amino acid peptide sequence identified in Table 5 as corresponding to the glycopeptide structure; and a glycan structure identified in Table 1 as corresponding to the glycopeptide structure in which the glycan structure is linked to a residue of the amino acid peptide sequence at a corresponding position identified in Table 1. The glycan structure has a glycan composition.

In one or more embodiments, a composition is provided, the composition comprising a peptide structure selected as one from a plurality of peptide structures identified in Table 1. The peptide structure has a monoisotopic mass identified as corresponding to the peptide structure in Table 1. The peptide structure comprises the amino acid sequence of SEQ ID NOs: 23-51 identified in Table 1 as corresponding to the peptide structure.

In one or more embodiments, a kit is provided, the kit comprising at least one agent for quantifying at least one peptide structure identified in Table 1 to carry out any one of the methods disclosed herein.

In one or more embodiments, a kit is provided, the kit comprising at least one of a glycopeptide standard, a buffer, or a set of peptide sequences to carry out any one of the methods disclosed herein. A peptide sequence of the set of peptide sequences identified by a corresponding one of SEQ ID NOS: 23-51, defined in Table 1.

In one or more embodiments, a system comprises one or more data processors; and a non-transitory computer readable storage medium containing instructions which, when executed on the one or more data processors, cause the one or more data processors to perform part or all of any one of the methods disclosed herein.

In one or more embodiments, a computer-program product tangibly embodied in a non-transitory machine-readable storage medium is provided, including instructions configured to cause one or more data processors to perform part or all of any one of the methods disclosed herein.

BRIEF DESCRIPTION OF THE DRAWINGS

The present disclosure is described in conjunction with the appended figures:

FIG. 2A (SEQ ID NO: 53-54) is a schematic diagram of a preparation workflow in accordance with one or more embodiments.

FIG. 2B is a schematic diagram of data acquisition in accordance with one or more embodiments.

FIG. 11 is a table of the sample population used for the experiments in accordance with one or more embodiments.

FIG. 12 is a table of the sample population used for validation in accordance with one or more embodiments.

FIGS. 23A-F show a table that identifies and defines the glycan structures included in Table 1. This table identifies a graphical representation of the one or more glycan structures associated with a particular glycan and a coded representation of the composition for each glycan structure included in Table 1. As used herein, the 4-digit GL NO. is a designation that represents the number of hexoses, the number of HexNAcs, the number of Fucoses, and the number of Neuraminic Acids.

DETAILED DESCRIPTION

I. Overview

Figure 1:
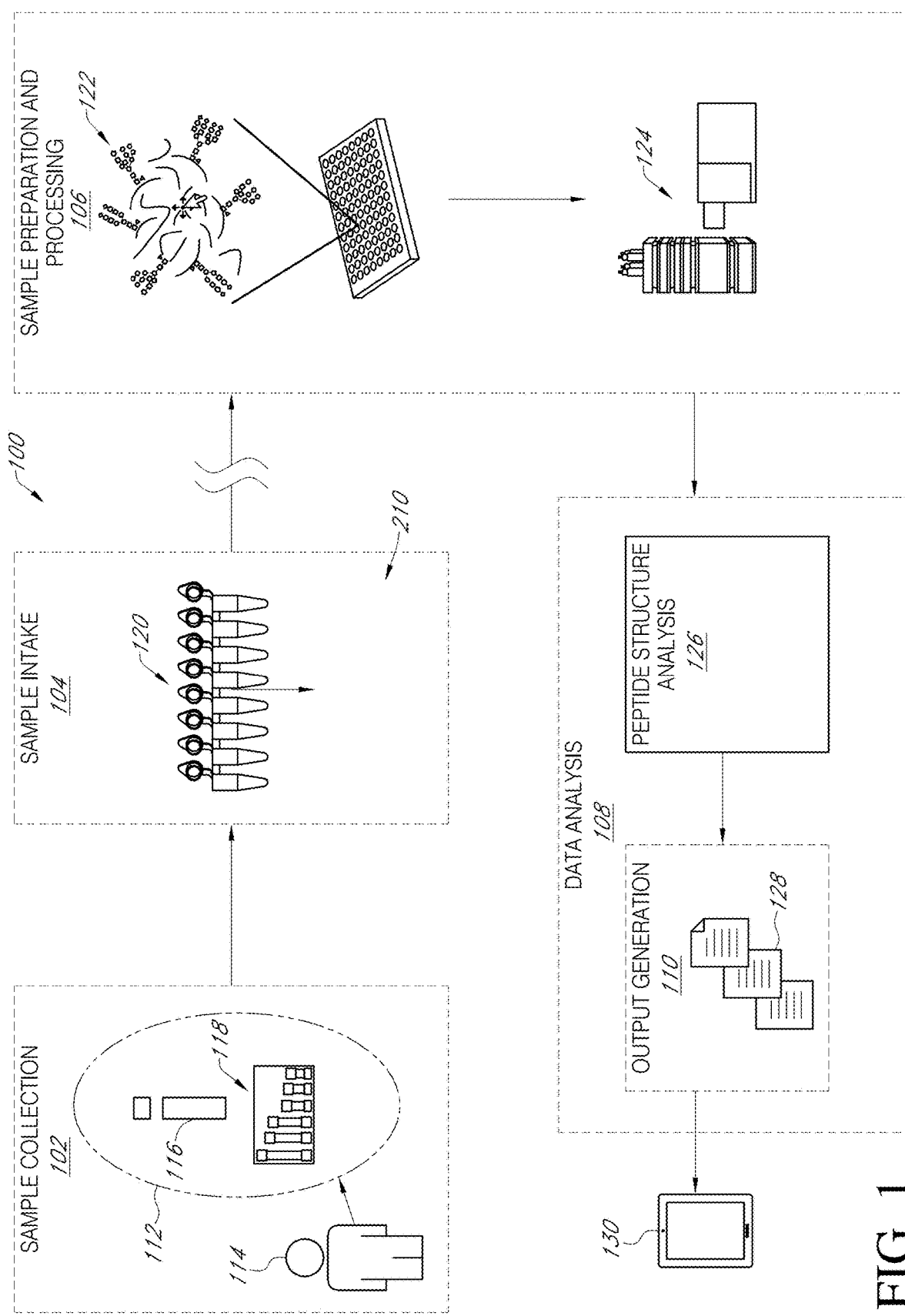
FIG. 1 is a schematic diagram of an exemplary workflow for the detection of peptide structures associated with a disease state for use in diagnosis and/or treatment in accordance with one or more embodiments.

The embodiments described herein recognize that glycoproteomics is an emerging field that can be used in the overall diagnosis and/or treatment of subjects with various types of diseases. Glycoproteomics aims to determine the positions, identities, and quantities of glycans and glycosylated proteins in a given sample (e.g., blood sample, cell, tissue, etc.). Protein glycosylation is one of the most common and most complex forms of post-translational protein modification, and can affect protein structure, conformation, and function. For example, glycoproteins may play crucial roles in important biological processes such as cell signaling, host-pathogen interactions, and immune response and disease. Glycoproteins may therefore be important to diagnosing different types of diseases. Glycoproteins may also be important to differentiating between stages within disease (e.g., the stages of FLD).

Although protein glycosylation provides useful information about cancer, other diseases, and stage determination of a disease analysis of protein glycosylation may be difficult as the glycan typically cannot be traced back to the protein site of origin with currently available methodologies. Glycoprotein analysis can be challenging in general for several reasons. For example, a single glycan composition in a peptide may contain a large number of isomeric structures because of different glycosidic linkages, branching, and many monosaccharides having the same mass. Further, the presence of multiple glycans that share the same peptide sequence may cause the mass spectrometry (MS) signal to split into various glycoforms, lowering their individual abundances compared to the peptides that are not glycosylated (aglycosylated peptides).

But to understand various disease conditions and disease progressions and to more accurately diagnose certain disease states, it may be important to perform analysis of glycoproteins and to identify not only the glycan but also the linking site (e.g., the amino acid residue of attachment) within the protein. Thus, there is a need to provide a method for site-specific glycoprotein analysis to obtain detailed information about protein glycosylation patterns which may be able to provide information about a disease state. This information can be used to distinguish the disease state from other states, diagnose a subject as having or not having the disease state, determine a likelihood that a subject has the disease state, or a combination thereof. Such analysis may be useful in distinguishing between, for example, without limitation, two or more of a non-alcoholic steatohepatitis (NASH) state, a hepatocellular carcinoma (HCC) state, and a non-NASH/HCC state (which may include at least one of a non-alcoholic FLD disease state, a control state, a healthy state, a liver disease-free state, or a benign hepatic mass state).

Accordingly, the embodiments described herein provide various methods and systems for analyzing proteins in subjects and, in particular, glycoproteins. In one or more embodiments, a machine learning model is trained to analyze peptide structure data and generate a disease indicator that provides information relating to one or more diseases. For example, in various embodiments, the peptide structure data comprises quantification metrics (e.g., abundance or concentration data) for peptide structures. A peptide structure may be defined by an aglycosylated peptide sequence (e.g., a peptide or peptide fragment of a larger parent protein) or a glycosylated peptide sequence. A glycosylated peptide sequence (also referred to as a glycopeptide structure) may be a peptide sequence having a glycan structure that is attached to a linking site (e.g., an amino acid residue) of the peptide sequence, which may occur via, for example, a particular atom of the amino acid residue). Non-limiting examples of glycosylated peptides include N-linked glycopeptides and O-linked glycopeptides.

The embodiments described herein recognize that the abundance of selected peptide structures in a biological sample obtained from a subject may be used to determine the likelihood of that subject having a particular disease state (e.g., stage of FLD).

Analyzing the abundance of peptide sequences and glycosylated peptide sequences in a biological sample may provide a more accurate way in which to distinguish the state of progression within FLD. This type of peptide structure analysis may be more conducive to generating accurate diagnoses as compared to glycoprotein analysis that focuses on analyzing glycoproteins that are too large to be resolved via mass spectrometry. Further, with glycoproteins, there may be too many potential proteoforms to consider. Still further, analysis of peptide structure data in the manner described by the various embodiments herein may be more conducive to generating accurate diagnoses as compared to glycomic analysis that provides little to no information about what proteins and to which amino acid residue sites various glycan structures attach.

The description below provides exemplary implementations of the methods and systems described herein for the research, diagnosis, and/or treatment (e.g., designing, planning, and/or manufacturing of a treatment) of a disease state (e.g., a NASH state, an HCC state, etc.) associated with FLD. Descriptions and examples of various terms, as used herein, are provided in Section II below.

II. Exemplary Descriptions of Terms

The term "ones" means more than one.

As used herein, the term "plurality" may be 2, 3, 4, 5, 6, 7, 8, 9, 10, or more.

As used herein, the term "set of" means one or more. For example, a set of items includes one or more items.

As used herein, the phrase "at least one of," when used with a list of items, means different combinations of one or more of the listed items may be used and only one of the items in the list may be needed. The item may be a particular object, thing, step, operation, process, or category. In other words, "at least one of" means any combination of items or number of items may be used from the list, but not all of the items in the list may be required. For example, without limitation, "at least one of item A, item B, or item C" means item A; item A and item B; item B; item A, item B, and item C; item B and item C; or item A and C. In some cases, "at least one of item A, item B, or item C" means, but is not limited to, two of item A, one of item B, and ten of item C; four of item B and seven of item C; or some other suitable combination.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

The term "amino acid," as used herein, generally refers to any organic compound that includes an amino group (e.g. —NH$_2$), a carboxyl group (—COOH), and a side chain group (R) which varies based on a specific amino acid. Amino acids can be linked using peptide bonds.

The term "alkylation," as used herein, generally refers to the transfer of an alkyl group from one molecule to another. In various embodiments, alkylation is used to react with reduced cysteines to prevent the re-formation of disulfide bonds after reduction has been performed.

The term "linking site" or "glycosylation site" as used herein generally refers to the location where a sugar molecule of a glycan or glycan structure is directly bound (e.g. covalently bound) to an amino acid of a peptide, a polypeptide, or a protein. For example, the linking site may be an amino acid residue and a glycan structure may be linked via an atom of the amino acid residue. Non-limiting examples of types of glycosylation can include N-linked glycosylation, O-linked glycosylation, C-linked glycosylation, S-linked glycosylation, and glycation.

The terms "biological sample," "biological specimen," or "biospecimen" as used herein, generally refers to a specimen taken by sampling so as to be representative of the source of the specimen, typically, from a subject. A biological sample can be representative of an organism as a whole, specific tissue, cell type, or category or sub-category of interest. The biological sample can include a macromolecule. The biological sample can include a small molecule. The biological sample can include a virus. The biological sample can include a cell or derivative of a cell. The biological sample can include an organelle. The biological sample can include a cell nucleus. The biological sample can include a rare cell from a population of cells. The biological sample can include any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The biological sample can include a constituent of a cell. The biological sample can include nucleotides (e.g. ssDNA, dsDNA, RNA), organelles, amino acids, peptides, proteins, carbohydrates, glycoproteins, or any combination thereof. The biological sample can include a matrix (e.g., a gel or polymer matrix) comprising a cell or one or more constituents from a cell (e.g., cell bead), such as DNA, RNA, organelles, proteins, or any combination thereof, from the cell. The biological sample may be obtained from a tissue of a subject. The biological sample can include a hardened cell. Such hardened cells may or may not include a cell wall or cell membrane. The biological sample can include one or more constituents of a cell but may not include other constituents of the cell. An example of such constituents may include a nucleus or an organelle. The biological sample may include a live cell. The live cell can be capable of being cultured.

The term "biomarker," as used herein, generally refers to any measurable substance taken as a sample from a subject whose presence is indicative of some phenomenon. Non-limiting examples of such phenomenon can include a disease state, a condition, or exposure to a compound or environmental condition. In various embodiments described herein, biomarkers may be used for diagnostic purposes (e.g. to diagnose a health state, an asymptomatic state, or a symptomatic state).

The term "denaturation," as used herein, generally refers to any molecule that loses quaternary structure, tertiary structure, and secondary structure which is present in their native state. Non-limiting examples include proteins or nucleic acids being exposed to an external compound or environmental condition such as acid, base, temperature, pressure, radiation, etc.

The term "denatured protein," as used herein, generally refers to a protein that loses quaternary structure, tertiary structure, and secondary structure which is present in their native state.

The terms "digestion" or "enzymatic digestion," as used herein, generally refer to breaking apart a polymer (e.g. cutting a polypeptide at a cut site). Proteins may be digested in preparation for mass spectrometry using trypsin digestion protocols. Proteins may be digested using other proteases in preparation for mass spectrometry if access is limited to cleavage sites.

The terms "immune checkpoint inhibitor therapeutic" and "immune checkpoint inhibitor drug," as used herein, generally refer to drugs or therapeutics that can target immune checkpoint molecules (e.g. molecules on immune cells that need to be activated (or inactivated) to start an immune response). Non-limiting examples of immune checkpoint inhibitor therapeutics can include pembrolizumab, nivolumab, and cemiplimab.

The term "disease progression," as used herein, refers to a progression of a disease from no disease or a less advanced (e.g., severe) form of disease to a more advanced (e.g., severe) form of the disease. A disease progression may include any number of stages of the disease.

The term "disease state" as used herein, generally refers to a condition that affects the structure or function of an organism. Non-limiting examples of causes of disease states may include pathogens, immune system dysfunctions, cell damage caused by aging, cell damage caused by other factors (e.g. trauma and cancer). Disease states can include, for example, stages of a disease progression. For example, for FLD, the progression may be from healthy to a stage of fat accumulation and inflammation (Fatty Liver), to non-alcoholic steatohepatitis (NASH), to fibrosis, and to cirrhosis. In some cases, the progression may advance from NASH to hepatocellular carcinoma (HCC). Disease states can include any state of a disease whether symptomatic or asymptomatic. Disease states can cause minor, moderate, or severe disruptions in the structure or function of a subject.

The terms "glycan" or "polysaccharide" as used herein, both generally refer to a carbohydrate residue of a glycoconjugate, such as the carbohydrate portion of a glycopeptide, glycoprotein, glycolipid, or proteoglycan. Glycans can include monosaccharides.

The term "glycopeptide" or "glycopolypeptide" as used herein, generally refer to a peptide or polypeptide comprising at least one glycan residue. In various embodiments, glycopeptides comprise carbohydrate moieties (e.g. one or more glycans) covalently attached to a side chain (i.e. R group) of an amino acid residue.

The term "glycoprotein," as used herein, generally refers to a protein having at least one glycan residue bonded thereto. In some examples, a glycoprotein is a protein with at least one oligosaccharide chain covalently bonded thereto. Examples of glycoproteins, include but are not limited to apolipoprotein C-III (APOC3), alpha-1-antichymotrypsin (AACT), afamin (AFAM), alpha-1-acid glycoprotein 1 & 2 (AGP12), apolipoprotein B-100 (APOB), apolipoprotein D (APOD), complement C1s subcomponent (C1S), calpain-3 (CAN3), clusterin (CLUS), complement component C8AChain (CO8A), alpha-2-HS-glycoprotein (FETUA), haptoglobin (HPT), immunoglobulin heavy constant gamma 1 (IgG1), immunoglobulin J chain (IgJ), plasma kallikrein (KLKB1), serum paraoxonase/arylesterase 1 (PON1), prothrombin (THRB), serotransferrin (TRFE), protein unc-13 homologA (UN13A), and zinc-alpha-2-glycoprotein (ZA2G). A glycopeptide, as used herein, refers to a fragment of a glycoprotein, unless specified otherwise to the contrary.

The term "liquid chromatography," as used herein, generally refers to a technique used to separate a sample into parts. Liquid chromatography can be used to separate, identify, and quantify components.

The term "mass spectrometry," as used herein, generally refers to an analytical technique used to identify molecules. In various embodiments described herein, mass spectrometry can be involved in characterization and sequencing of proteins.

The term "peptide," as used herein, generally refers to amino acids linked by peptide bonds. Peptides can include amino acid chains between 10 and 50 residues. Peptides can include amino acid chains shorter than 10 residues, including, oligopeptides, dipeptides, tripeptides, and tetrapeptides. Peptides can include chains longer than 50 residues and may be referred to as "polypeptides" or "proteins."

The terms "protein" or "polypeptide" or "peptide" may be used interchangeably herein and generally refer to a molecule including at least three amino acid residues. Proteins can include polymer chains made of amino acid sequences linked together by peptide bonds. Proteins may be digested in preparation for mass spectrometry using trypsin digestion protocols. Proteins may be digested using other proteases in preparation for mass spectrometry if access is limited to cleavage sites.

The term "peptide structure," as used herein, generally refers to peptides or a portion thereof or glycopeptides or a portion thereof. In various embodiments described herein, a peptide structure can include any molecule comprising at least two amino acids in sequence.

The term "reduction," as used herein, generally refers to the gain of an electron by a substance. In various embodiments described herein, a sugar can directly bind to a protein, thereby, reducing the amino acid to which it binds. Such reducing reactions can occur in glycosylation. In various embodiments, reduction may be used to break disulfide bonds between two cysteines.

The term "sample," as used herein, generally refers to a sample from a subject of interest and may include a biological sample of a subject. The sample may include a cell sample. The sample may include a cell line or cell culture sample. The sample can include one or more cells. The sample can include one or more microbes. The sample may include a nucleic acid sample or protein sample. The sample may also include a carbohydrate sample or a lipid sample. The sample may be derived from another sample. The sample may include a tissue sample, such as a biopsy, core biopsy, needle aspirate, or fine needle aspirate. The sample may include a fluid sample, such as a blood sample, urine sample, or saliva sample. The sample may include a skin sample. The sample may include a check swab. The sample may include a plasma or serum sample. The sample may include a cell-free or cell free sample. A cell-free sample may include extracellular polynucleotides. The sample may originate from blood, plasma, serum, urine, saliva, mucosal excretions, sputum, stool, or tears. The sample may originate from red blood cells or white blood cells. The sample may originate from feces, spinal fluid, CNS fluid, gastric fluid, amniotic fluid, cyst fluid, peritoneal fluid, marrow, bile, other body fluids, tissue obtained from a biopsy, skin, or hair.

The term "sequence," as used herein, generally refers to a biological sequence including one-dimensional monomers that can be assembled to generate a polymer. Non-limiting examples of sequences include nucleotide sequences (e.g. ssDNA, dsDNA, and RNA), amino acid sequences (e.g. proteins, peptides, and polypeptides), and carbohydrates (e.g. compounds including $C_m(H_2O)_n$).

The term "subject," as used herein, generally refers to an animal, such as a mammal (e.g., human) or avian (e.g., bird), or other organism, such as a plant. For example, the subject can include a vertebrate, a mammal, a rodent (e.g., a mouse), a primate, a simian or a human. Animals may include, but are not limited to, farm animals, sport animals, and pets. A subject can include a healthy or asymptomatic individual, an individual that has or is suspected of having a disease (e.g., cancer) or a pre-disposition to the disease, and/or an individual that is in need of therapy or suspected of needing therapy. A subject can be a patient. A subject can include a microorganism or microbe (e.g., bacteria, fungi, archaea, viruses).

As used herein, a "model" may include one or more algorithms, one or more mathematical techniques, one or more machine learning algorithms, or a combination thereof.

As used herein, "machine learning" may be the practice of using algorithms to parse data, learn from it, and then make a determination or prediction about something in the world. Machine learning uses algorithms that can learn from data without relying on rules-based programming. A machine learning algorithm may include a parametric model, a non-parametric model, a deep learning model, a neural network, a linear discriminant analysis model, a quadratic discriminant analysis model, a support vector machine, a random forest algorithm, a nearest neighbor algorithm, a combined discriminant analysis model, a k-means clustering algorithm, a supervised model, an unsupervised model, logistic regression model, a multivariable regression model, a penalized multivariable regression model, or another type of model.

As used herein, an "artificial neural network" or "neural network" (NN) may refer to mathematical algorithms or computational models that mimic an interconnected group of artificial nodes or neurons that processes information based on a connectionistic approach to computation. Neural networks, which may also be referred to as neural nets, can employ one or more layers of nonlinear units to predict an output for a received input. Some neural networks include one or more hidden layers in addition to an output layer. The output of each hidden layer is used as input to the next layer in the network, i.e., the next hidden layer or the output layer. Each layer of the network generates an output from a received input in accordance with current values of a respective set of parameters. In the various embodiments, a reference to a "neural network" may be a reference to one or more neural networks.

A neural network may process information in two ways: when it is being trained it is in training mode and when it puts what it has learned into practice it is in inference (or prediction) mode. Neural networks learn through a feedback process (e.g., backpropagation) which allows the network to adjust the weight factors (modifying its behavior) of the individual nodes in the intermediate hidden layers so that the output matches the outputs of the training data. In other words, a neural network learns by being fed training data (learning examples) and eventually learns how to reach the correct output, even when it is presented with a new range or set of inputs. A neural network may include, for example, without limitation, at least one of a Feedforward Neural Network (FNN), a Recurrent Neural Network (RNN), a Modular Neural Network (MNN), a Convolutional Neural Network (CNN), a Residual Neural Network (ResNet), an Ordinary Differential Equations Neural Networks (neural-ODE), or another type of neural network.

III. Overview of Exemplary Workflow

FIG. 1 is a schematic diagram of an exemplary workflow 100 for the detection of peptide structures associated with a disease state for use in diagnosis and/or treatment in accordance with one or more embodiments. Workflow 100 may include various operations including, for example, sample collection 102, sample intake 104, sample preparation and processing 106, data analysis 108, and output generation 110.

Sample collection 102 may include, for example, obtaining a biological sample 112 of one or more subjects, such as subject 114. Biological sample 112 may take the form of a specimen obtained via one or more sampling methods. Biological sample 112 may be representative of subject 114 as a whole or of a specific tissue, cell type, or other category or sub-category of interest. Biological sample 112 may be obtained in any of a number of different ways. In various embodiments, biological sample 112 includes whole blood sample 116 obtained via a blood draw. In other embodiments, biological sample 112 includes set of aliquoted samples 118 that includes, for example, a serum sample, a plasma sample, a blood cell (e.g., white blood cell (WBC), red blood cell (RBC) sample, another type of sample, or a combination thereof. Biological samples 112 may include nucleotides (e.g. ssDNA, dsDNA, RNA), organelles, amino acids, peptides, proteins, carbohydrates, glycoproteins, or any combination thereof.

Sample intake 104 may include one or more various operations such as, for example, aliquoting, registering, processing, storing, thawing, and/or other types of operations. In one or more embodiments, when biological sample 112 includes whole blood sample 116, sample intake 104 includes aliquoting whole blood sample 116 to form a set of aliquoted samples that can then be sub-aliquoted to form set of samples 120.

Sample preparation and processing 106 may include, for example, one or more operations to form set of peptide structures 122. In various embodiments, set of peptide structures 122 may include various fragments of unfolded proteins that have undergone digestion and may be ready for analysis.

Further, sample preparation and processing 106 may include, for example, data acquisition 124 based on set of peptide structures 122. For example, data acquisition 124 may include use of, for example, but is not limited to, a liquid chromatography/mass spectrometry (LC/MS) system.

Data analysis 108 may include, for example, peptide structure analysis 126. In some embodiments, data analysis 108 also includes output generation 110. In other embodiments, output generation 110 may be considered a separate operation from data analysis 108. Output generation 110 may include, for example, generating final output 128 based on the results of peptide structure analysis 126. In various embodiments, final output 128 may be used for determining the research, diagnosis, and/or treatment of a state associated with fatty liver disease.

In various embodiments, final output 128 is comprised of one or more outputs. Final output 128 may take various forms. For example, final output 128 may be a report that includes, for example, a diagnosis output, a treatment output (e.g., a treatment design output, a treatment plan output, or combination thereof), or combination thereof. In some embodiments, final output 128 may be an alert (e.g., a visual alert, an audible alert, etc.), a notification (e.g., a visual notification, an audible notification, an email notification, etc.), an email output, or a combination thereof. In some embodiments, final output 128 may be sent to remote system 130 for processing. Remote system 130 may include, for example, a computer system, a server, a processor, a cloud computing platform, cloud storage, a laptop, a tablet, a smartphone, some other type of mobile computing device, or a combination thereof.

In other embodiments, workflow 100 may optionally exclude one or more of the operations described herein and/or may optionally include one or more other steps or operations other than those described herein (e.g., in addition to and/or instead of those described herein). Accordingly, workflow 100 may be implemented in any of a number of different ways for use in the research, diagnosis, and/or treatment of, for example, FLD.

IV. Detection and Quantification of Peptide Structures

FIGS. 2A and 2B are schematic diagrams of a workflow for sample preparation and processing 106 in accordance with one or more embodiments. FIGS. 2A and 2B are described with continuing reference to FIG. 1. Sample preparation and processing 106 may include, for example, preparation workflow 200 shown in FIG. 2A and data acquisition 124 shown in FIG. 2B.

IV.A. Sample Preparation and Processing

FIG. 2A is a schematic diagram of preparation workflow 200 in accordance with one or more embodiments. Preparation workflow 200 may be used to prepare a sample, such as a sample of set of samples 120 in FIG. 1, for analysis via data acquisition 124. For example, this analysis may be performed via mass spectrometry. In various embodiments, preparation workflow 200 may include denaturation and reduction 202, alkylation 204, and digestion 206.

In general, polymers, such as proteins, in their native form, can fold to include secondary, tertiary, and/or other higher order structures. Such higher order structures may functionalize proteins to complete tasks (e.g. enable enzymatic activity) in a subject. Further, such higher order structures of polymers may be maintained via various interactions between side chains of amino acids within the polymers. Such interactions can include ionic bonding, hydrophobic interactions, hydrogen bonding, and disulfide linkages between cysteine residues. However, when using analytic systems and methods, including mass spectrometry, unfolding such polymers (e.g. peptide/protein molecules) may be desired to obtain sequence information. In some embodiments, unfolding a polymer may include denaturing the polymer, which may include, for example, linearizing the polymer.

In one or more embodiments, denaturation and reduction 202 can be used to disrupt higher order structures (e.g., secondary, tertiary, quaternary, etc.) of one or more proteins (e.g., polypeptides and peptides) in a sample (e.g., one of set of samples 120 in FIG. 1). Denaturation and reduction 202 includes, for example, a denaturation procedure and a reduction procedure. In some embodiments, the denaturation procedure may be performed using, for example, thermal denaturation, where heat is used as a denaturing agent. The thermal denaturation can disrupt ionic bonding, hydrophobic interactions, and/or hydrogen bonding.

In one or more embodiments, the denaturation procedure may include using one or more denaturing agents in combination with heat. These one or more denaturing agents may include, for example, but are not limited to, any number of chaotropic salts (e.g., urea, guanidine), surfactants (e.g., sodium dodecyl sulfate (SDS), beta octyl glucoside, Triton X-100), or combination thereof. In some cases, such denaturing agents may be used in combination with heat when sample preparation workflow further includes a cleanup procedure.

The resulting one or more denatured (e.g., unfolded, linearized) proteins may then undergo further processing in preparation of analysis. For example, a reduction procedure may be performed in which one or more reducing agents are applied. A reducing agent may take the form of, for example, limitation, dithiothreitol (DTT), tris(2-carboxyethyl)phosphine (TCEP), or some other reducing agent. The reducing agent may reduce (e.g., cleave) the disulfide linkages between cysteine residues of the one or more denatured proteins to form one or more reduced proteins.

In various embodiments, the one or more reduced proteins resulting from denaturation and reduction 202 may undergo a process to prevent the reformation of disulfide linkages between, for example, the cysteine residues of the one or more reduced proteins. This process may be implemented using alkylation 204 to form one or more alkylated proteins. For example, alkylation 204 may be used add an acetamide group to a sulfur on each cysteine residue to prevent disulfide linkages from reforming. In various embodiments, an acetamide group can be added by reacting one or more alkylating agents with a reduced protein. The one or more alkylating agents may include, for example, one or more acetamide salts. An alkylating agent may take the form of, for example, iodoacetamide (IAA), 2-chloroacetamide, some other type of acetamide salt, or some other type of alkylating agent.

In some embodiments, alkylation 204 may include a quenching procedure. The quenching procedure may be performed using one or more reducing agents (e.g., one or more of the reducing agents described above).

In various embodiments, the one or more alkylated formed via alkylation 204 can then undergo digestion 206 in preparation for analysis (e.g., mass spectrometry analysis). Digestion 206 of a protein may include cleaving the protein at or around one or more cleavage sites (e.g., site 205 which may be one or more amino acid residues). For example, without limitation, an alkylated protein may be cleaved at the carboxyl side of the lysine or arginine residues. This type of cleavage may break the protein into various segments, which include one or more peptide structures (e.g., glycosylated or aglycosylated).

In various embodiments, digestion 206 is performed using one or more proteolysis catalysts. For example, an enzyme can be used in digestion 206. In some embodiments, the enzyme takes the form of trypsin. In other embodiments, one or more other types of enzymes (e.g., proteases) may be used in addition to or in place of trypsin. These one or more other enzymes include, but are not limited to, LysC, LysN, AspN, GluC, and ArgC. In some embodiments, digestion 206 may be performed using tosyl phenylalanyl chloromethyl ketone (TPCK)-treated trypsin, one or more engineered forms of trypsin, one or more other formulations of trypsin, or a combination thereof. In some embodiments, digestion 206 may be performed in multiple steps, with each involving the use of one or more digestion agents. For example, a secondary digestion, tertiary digestion, etc. may be performed. In one or more embodiments, trypsin is used to digest serum samples. In one or more embodiments, trypsin/LysC cocktails are used to digest plasma samples.

In some embodiments, digestion 206 further includes a quenching procedure. The quenching procedure may be performed by acidifying the sample (e.g., to a pH<3). In some embodiments, formic acid may be used to perform this acidification.

In various embodiments, preparation workflow 200 further includes post-digestion procedure 207. Post-digestion procedure 207 may include, for example, a cleanup procedure. The cleanup procedure may include, for example, the removal of unwanted components in the sample that results from digestion 206. For example, unwanted components may include, but are not limited to, inorganic ions, surfactants, etc. In some embodiments, post-digestion procedure 207 further includes a procedure for the addition of heavy-labeled peptide internal standards.

Although preparation workflow 200 has been described with respect to a sample created or taken from biological sample 112 that is blood-based (e.g., a whole blood sample, a plasma sample, a serum sample, etc.), sample preparation workflow 200 may be similarly implemented for other types of samples (e.g., tears, urine, tissue, interstitial fluids, sputum, etc.) to produce set of peptides structures 122.

IV.B. Peptide Structure Identification and Quantitation

FIG. 2B is a schematic diagram of data acquisition 124 in accordance with one or more embodiments. In various embodiments, data acquisition 124 can commence following sample preparation 200 described in FIG. 2A. In various embodiments, data acquisition 124 can comprise quantification 208, quality control 210, and peak integration and normalization 212.

In various embodiments, targeted quantification 208 of peptides and glycopeptides can incorporate use of liquid chromatography-mass spectrometry LC/MS instrumentation. For example, LC-MS/MS, or tandem MS may be used. In general, LC/MS (e.g., LC-MS/MS) can combine the physical separation capabilities of liquid chromatograph (LC) with the mass analysis capabilities of mass spectrometry (MS). According to some embodiments described herein, this technique allows for the separation of digested peptides to be fed from the LC column into the MS ion source through an interface.

In various embodiments, any LC/MS device can be incorporated into the workflow described herein. In various embodiments, a Triple Quadrupole LC/MS™ includes example instruments suited for identification and targeted quantification 208. In various embodiments, targeted quantification 208 is performed using multiple reaction monitoring mass spectrometry (MRM-MS).

In various embodiments described herein, identification of a particular protein or peptide and an associated quantity can be assessed. In various embodiments described herein, identification of a particular glycan and an associated quantity can be assessed. In various embodiments described herein, particular glycans can be matched to a glycosylation site on a protein or peptide and their absolute or relative quantities assessed.

In some cases, targeted quantification 208 includes using a specific collision energy associated for the appropriate fragmentation to consistently see an abundant product ion. Glycopeptide structures may have a lower collision energy than aglycosylated peptide structures. When analyzing a sample that includes glycopeptide structures, the source voltage and gas temperature may be lowered as compared to generic proteomic analysis.

In various embodiments, quality control 210 procedures can be put in place to optimize data quality. In various embodiments, measures can be put in place allowing only errors within acceptable ranges outside of an expected value. In various embodiments, employing statistical models (e.g. using Westgard rules) can assist in quality control 210. For example, quality control 210 may include, for example, assessing the retention time and abundance of representative peptide structures (e.g., glycosylated and/or aglycosylated) and spiked-in internal standards, in either every sample, or in each quality control sample (e.g., pooled serum digest).

Peak integration and normalization 212 may be performed to process the data that has been generated and transform the data into a format for analysis. For example, peak integration and normalization 212 may include converting abundance data for various product ions that were detected for a selected peptide structure into a single quantification metric (e.g., a relative quantity, an adjusted quantity, a normalized quantity, a relative concentration, an adjusted concentration, a normalized concentration, etc.) for that peptide structure. In some embodiments, peak integration and normalization 212 may be performed using one or more of the techniques described in U.S. Patent Publication No. 2020/0372973A1 and/or US Patent Publication No. 2020/0240996A1, the disclosures of which are incorporated by reference herein in their entireties.

V. Exemplary System for Peptide Structure Data Analysis

V.A. Analysis System for Peptide Structure Data Analysis

Figure 3:
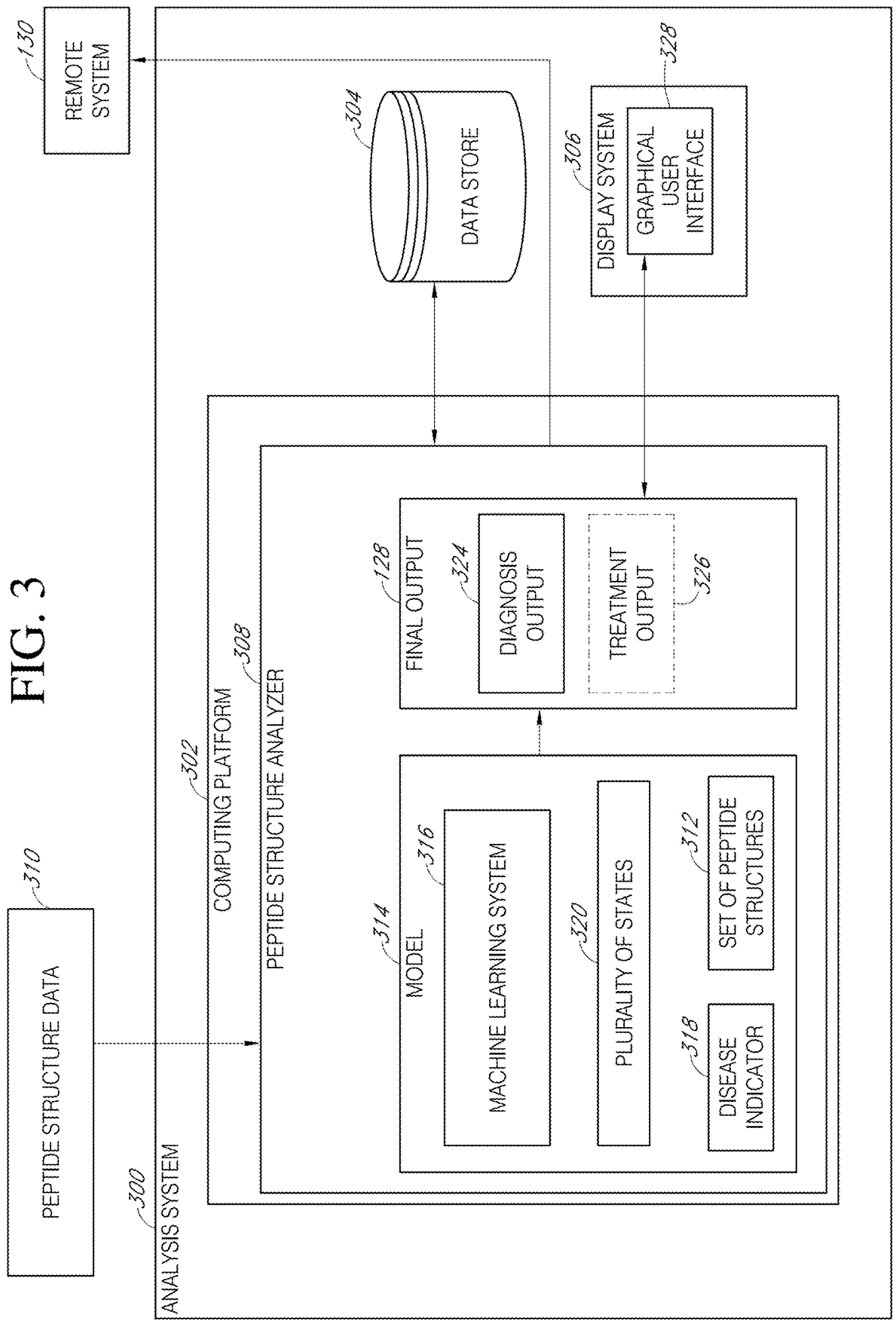
FIG. 3 is a block diagram of an analysis system in accordance with one or more embodiments.

FIG. 3 is a block diagram of an analysis system 300 in accordance with one or more embodiments. Analysis system 300 can be used to both detect and analyze various peptide structures that have been associated with various states of FLD. Analysis system 300 is one example of an implementation for a system that may be used to perform data analysis 108 in FIG. 1. Thus, analysis system 300 is described with continuing reference to workflow 100 as described in FIGS. 1, 2A, and/or 2B.

Analysis system 300 may include computing platform 302 and data store 304. In some embodiments, analysis system 300 also includes display system 306. Computing platform 302 may take various forms. In one or more embodiments, computing platform 302 includes a single computer (or computer system) or multiple computers in communication with each other. In other examples, computing platform 302 takes the form of a cloud computing platform.

Data store 304 and display system 306 may each be in communication with computing platform 302. In some examples, data store 304, display system 306, or both may be considered part of or otherwise integrated with computing platform 302. Thus, in some examples, computing platform 302, data store 304, and display system 306 may be separate components in communication with each other, but in other examples, some combination of these components may be integrated together. Communication between these different components may be implemented using any number of wired communications links, wireless communications links, optical communications links, or a combination thereof.

Analysis system 300 includes, for example, peptide structure analyzer 308, which may be implemented using hardware, software, firmware, or a combination thereof. In one or more embodiments, peptide structure analyzer 308 is implemented using computing platform 302.

Peptide structure analyzer 308 receives peptide structure data 310 for processing. Peptide structure data 310 may be, for example, the peptide structure data that is output from sample preparation and processing 106 in FIGS. 1, 2A, and 2B. Accordingly, peptide structure data 310 may correspond to set of peptide structures 122 identified for biological sample 112 and may thereby correspond to biological sample 112.

Peptide structure data 310 can be sent as input into peptide structure analyzer 308, retrieved from data store 304 or some other type of storage (e.g., cloud storage), accessed from cloud storage, or obtained in some other manner. In some cases, peptide structure data 310 may be retrieved from data store 304 in response to (e.g., directly or indirectly based on) receiving user input entered by a user via an input device.

Peptide structure data 310 may include quantification data for the plurality of peptide structures. For example, peptide structure data 310 may include a set of quantification metrics for each peptide structure of a plurality of peptide structures. A quantification metric for a peptide structure may be selected as one of a relative quantity, an adjusted quantity, a normalized quantity, a relative abundance, an adjusted abundance, and a normalized abundance. In some cases, a quantification metric for a peptide structure is selected from one of a relative concentration, an adjusted concentration, and a normalized concentration. In this manner, peptide structure data 310 may provide abundance information about the plurality of peptide structures with respect to biological sample 112.

In some embodiments, a peptide structure of set of peptide structures 312 comprises a glycosylated peptide structure, or glycopeptide structure, that is defined by a peptide sequence and a glycan structure attached to a linking site of the peptide sequence quantity. For example, the peptide structure may be a glycopeptide or a portion of a glycopeptide. In some embodiments, a peptide structure of set of peptide structures 312 comprises an aglycosylated peptide structure that is defined by a peptide sequence. For example, the peptide structure may be a peptide or a portion of a peptide and may be referred to as a quantification peptide.

Set of peptide structures 312 may be identified as being those most predictive or relevant to the symptomatic disease state based on training of model 314. In one or more embodiments, set of peptide structures 312 includes at least one, at least three, or at least five of the peptide structures identified in Table 1 below. The number of peptide structures selected from Table 1 for inclusion in set of peptide structures 312 may be based on, for example, a desired level of accuracy. In one or more embodiments, 40 peptide structures are selected from Table 1 for inclusion in set of peptide structures 312.

TABLE 1

Peptide Structures associated with FLD

| PS-ID NO. | Peptide Structure (PS) Name | (Protein) SEQ ID NO. | (Peptide) SEQ ID NO. | Mono-isotopic mass (Da) | Linking Site Pos. in Protein Sequence | Linking Site Pos. in Peptide Sequence | Glycan Structure GL NO. |
|---|---|---|---|---|---|---|---|
| PS-1 | A1AT (271) - 5401 | 1 | 23 | 3668.56 | 271 | 4 | 5401 |
| PS-2 | A1AT (271) - 5402 | 1 | 23 | 3959.66 | 271 | 4 | 5402 |
| PS-3 | A1BG (179) - 5402 | 2 | 24 | 6040.44 | 179 | 27 | 5402 |
| PS-4 | A2MG-AIGYLNTGYQR | 3 | 25 | 1254.64 | N/A | N/A | N/A |
| PS-5 | A2MG-TEHPFTVEEFVLPK | 3 | 26 | 1671.85 | N/A | N/A | N/A |
| PS-6 | A2MG (1424) - 5402 | 3 | 27 | 4366.95 | 1424 | 3 | 5402 |
| PS-7 | A2MG (247) - 5200 | 3 | 28 | 4950.31 | 247 | 10 | 5200 |
| PS-8 | A2MG (247) - 5401 | 3 | 28 | 5647.57 | 247 | 10 | 5401 |
| PS-9 | A2MG (247) - 5402 | 3 | 28 | 5938.66 | 247 | 10 | 5402 |
| PS-10 | A2MG (55) - 5402 | 3 | 29 | 4601.00 | 55 | 9 | 5402 |

TABLE 1-continued

Peptide Structures associated with FLD

| PS-ID NO. | Peptide Structure (PS) Name | (Protein) SEQ ID NO. | (Peptide) SEQ ID NO. | Monoisotopic mass (Da) | Linking Site Pos. in Protein Sequence | Linking Site Pos. in Peptide Sequence | Glycan Structure GL NO. |
|---|---|---|---|---|---|---|---|
| PS-11 | A2MG (55) - 5411 | 3 | 29 | 4455.96 | 55 | 9 | 5411 |
| PS-12 | A2MG (55) - 5412 | 3 | 29 | 4747.06 | 55 | 9 | 5412 |
| PS-13 | A2MG (869) - 5200 | 3 | 30 | 4629.04 | 869 | 6 | 5200 |
| PS-14 | A2MG (869) - 6200 | 3 | 30 | 4791.10 | 869 | 6 | 6200 |
| PS-15 | A2MG (869) - 6300 | 3 | 30 | 4994.18 | 869 | 6 | 6300 |
| PS-16 | A2MG (991) - 5402 | 3 | 31 | 8432.83 | 991 | 46 | 5402 |
| PS-17 | AACT (106) - 7604 | 4 | 32 | 5916.41 | 106 | 2 | 7604 |
| PS-18 | AFAM (33) - 5402 | 5 | 33 | 3399.32 | 33 | 6 | 5402 |
| PS-19 | AGP1 (33) - 5402 | 6 | 34 | 4780.18 | 33 | 15 | 5402 |
| PS-20 | AGP1 (93) - 6502 | 6 | 35 | 4484.79 | 93 | 7 | 6502 |
| PS-21 | APOC3 (74) - 1102 | 7 | 36 | 3083.34 | 94 | 14 | 1102 |
| PS-22 | APOC3 (74) - 1202 | 7 | 36 | 3286.42 | 94 | 14 | 1202 |
| PS-23 | APOC3 (74) - 1300 | 7 | 36 | 2907.31 | 94 | 14 | 1300 |
| PS-24 | APOC3 (74) - 2110 | 7 | 36 | 2809.26 | 94 | 14 | 2110 |
| PS-25 | APOM (135) - 5421 | 8 | 37 | 4736.93 | 135 | 15 | 5421 |
| PS-26 | CFAI (70) - 5401 | 9 | 38 | 2976.16 | 70 | 1 | 5401 |
| PS-27 | CLUS (374) - 6501 | 10 | 39 | 3961.64 | 374 | 3 | 6501 |
| PS-28 | CO4A (1328) - 5402 | 11 | 40 | 3308.37 | 1328 | 3 | 5402 |
| PS-29 | CO6 (324) - 5200 | 12 | 41 | 2037.89 | 324 | 3 | 5200 |
| PS-30 | CO6 (324) - 5400 | 12 | 41 | 2444.05 | 324 | 3 | 5400 |
| PS-31 | CO8A (437) - 5200 | 13 | 42 | 2549.04 | 437 | 13 | 5200 |
| PS-32 | CO8A (437) - 5410 | 13 | 42 | 3101.26 | 437 | 13 | 5410 |
| PS-33 | HPT (207) - 10803 | 14 | 43 | 5576.18 | 207 & 211 | 5 & 9 | 5401 & 5402 |
| PS-34 | HPT (207) - 11904 | 14 | 43 | 6232.40 | 207 & 211 | 5 & 9 | 6502 & 5402 |
| PS-35 | HPT (207) - 121005 | 14 | 43 | 6888.63 | 207 & 211 | 5 & 9 | 6503 & 6502 |
| PS-36 | HPT (241) - 5401 | 14 | 44 | 3707.68 | 241 | 6 | 5401 |
| PS-37 | HPT (241) - 5402 | 14 | 44 | 3998.78 | 241 | 6 | 5402 |
| PS-38 | HPT (241) - 5511 | 14 | 44 | 4056.82 | 241 | 6 | 5511 |
| PS-39 | HPT (241) - 6502 | 14 | 44 | 4363.91 | 241 | 6 | 6502 |
| PS-40 | IGA2 (205) - 5510 | 15 | 45 | 2929.27 | 205 | 6 | 5510 |
| PS-41 | IGG1 (297) - 5411 | 16 | 46 | 3248.24 | 180 | 5 | 5411 |
| PS-42 | IGG2 (297) - 4400 | 17 | 46 | 2617.04 | 176 | 5 | 4400 |
| PS-43 | IGG2 (297) - 4411 | 17 | 46 | 3054.20 | 176 | 5 | 4411 |
| PS-44 | IGM (209) - 5401 | 18 | 47 | 4251.75 | 209 | 7 | 5401 |
| PS-45 | KLKB1 (494) - 5401 | 19 | 48 | 4159.85 | 494 | 6 | 5401 |
| PS-46 | KLKB1 (494) - 5402 | 19 | 48 | 4450.95 | 494 | 6 | 5402 |
| PS-47 | KLKB1 (494) - 5410 | 19 | 48 | 4014.82 | 494 | 6 | 5410 |
| PS-48 | KLKB1 (494) - 6503 | 19 | 48 | 5107.18 | 494 | 6 | 6503 |
| PS-49 | TRFE (432) - 5402 | 20 | 49 | 3680.52 | 432 | 12 | 5402 |
| PS-50 | TRFE (432) - 6501 | 20 | 49 | 3754.55 | 432 | 12 | 6501 |
| PS-51 | TRFE (432) - 6502 | 20 | 49 | 4045.65 | 432 | 12 | 6502 |
| PS-52 | VTNC (169) - 5401 | 21 | 50 | 2824.14 | 169 | 1 | 5401 |
| PS-53 | ZA2G (112) - 5402 | 22 | 51 | 4269.72 | 112 | 10 | 5402 |

In one or more embodiments, set of peptide structures 312 includes only peptide structures fragmented from alpha-2-macroglobulin (A2MG) and thus only A2MG glycoforms. In one or more embodiments, set of peptide structures 312 includes only peptide structures fragmented from the alpha-1-acid glycoprotein 1 (AGP1) and thus only AGP1 glycoforms. In one or more embodiments, set of peptide structures 312 includes only peptide structures fragmented from haptoglobin (HPT) and thus only HPT glycoforms. In one or more embodiments, set of peptide structures 312 includes only peptide structures fragmented from Complement Factor H (CFAH) and thus only CFAH glycoforms. In one or more embodiments, set of peptide structures 312 includes only peptide structures fragmented from alpha-1-antitrypsin (A1AT) and thus only A1AT glycoforms. In some embodiments, set of peptide structures 312 includes only peptide structures fragmented from at least one of A2MG, AGP1, HPT, CFAH, or A1AT.

Peptide structure analyzer 308 includes model 314 that is configured to receive peptide structure data 310 for processing. Model 314 may be implemented in any of a number of different ways. Model 314 may be implemented using any number of models, functions, equations, algorithms, and/or other mathematical techniques.

In one or more embodiments, model 314 includes machine learning model 316, which may itself be comprised of any number of machine learning models and/or algorithms. For example, machine learning model 316 may include, without limitation, at least one of a parametric model, a non-parametric model, deep learning model, a neural network, a linear discriminant analysis model, a quadratic discriminant analysis model, a support vector machine, a random forest algorithm, a nearest neighbor algorithm (e.g., a k-Nearest Neighbors algorithm), a combined discriminant analysis model, a k-means clustering algorithm, an unsupervised model, a logistic regression model, a multivariable regression model, a penalized multivariable regression model, or another type of model. In various embodiments, model 314 includes a machine learning model 316 that comprises any number of or combination of the models or algorithms described above.

In various embodiments, model 314 analyzes the portion (e.g., some or all of) peptide structure data 310 corresponding set of peptide structures 312 to generate disease indicator 318 that classifies biological sample 112 as evidencing a corresponding state of a plurality of states 320 associated with FLD progression. Disease indicator 318 may take various forms. In one or more embodiments, disease indicator 318 is a score that indicates a classification of the corresponding state for biological sample 112. For example, each of the states 320 may be associated with a different range of values for the score. If the score falls within a selected range associated with a particular state of the states 320, then the score indicates that biological sample 112 evidences that particular state. Thus, the score provides a classification of biological sample 112 as corresponding to that particular state.

In other embodiments, disease indicator 318 includes a score that indicates a probability that a subject (e.g., subject 114 in FIG. 1) falls within one of the states 320 associated with FLD progression. For example, disease indicator 318 may include one or more scores, each of which may indicate whether biological sample 112 evidences a corresponding state of the states 320 associated with FLD progression. In some examples, disease indicator 318 includes a score for each of the states 320 associated with FLD progression. A higher score indicates a higher probability that biological sample 112 evidences the corresponding state.

In various embodiments, machine learning model 316 takes the form of regression model 320. Regression model 320 may include, for example, at least one LASSO regression model (or LASSO regularization model) that is trained to compute disease indicator 318. Regression model 320 may be trained to identify weight coefficients for peptide structures of set of peptide structures 312.

Peptide structure analyzer 308 may generate final output 128 based on disease indicator 318 that is output by model 314. In other embodiments, final output 128 may be an output generated by model 314.

In some embodiments, final output 128 includes disease indicator 318. In other embodiments, final output 128 includes diagnosis output 324 and/or treatment output 326. Diagnosis output 324 may include, for example, an identification of a classification of which of the states 320 evidenced by biological sample 112 based on disease indicator 318. Treatment output 326 may include, for example, at least one of an identification of a therapeutic to treat the subject, a design for the therapeutic, or a treatment plan for administering the therapeutic. In some embodiments, the therapeutic is an immune checkpoint inhibitor.

Final output 128 may be sent to remote system 130 for processing in some examples. In other embodiments, final output 128 may be displayed on graphical user interface 328 in display system 306 for viewing by a human operator. The human operator may use final output 128 to diagnose and/or treat subject when final output 128 indicates the subject is positive a state (e.g., NASH, HCC) along a disease progression of a disease (e.g., FLD).

V.B. Computer Implemented System

Figure 4:
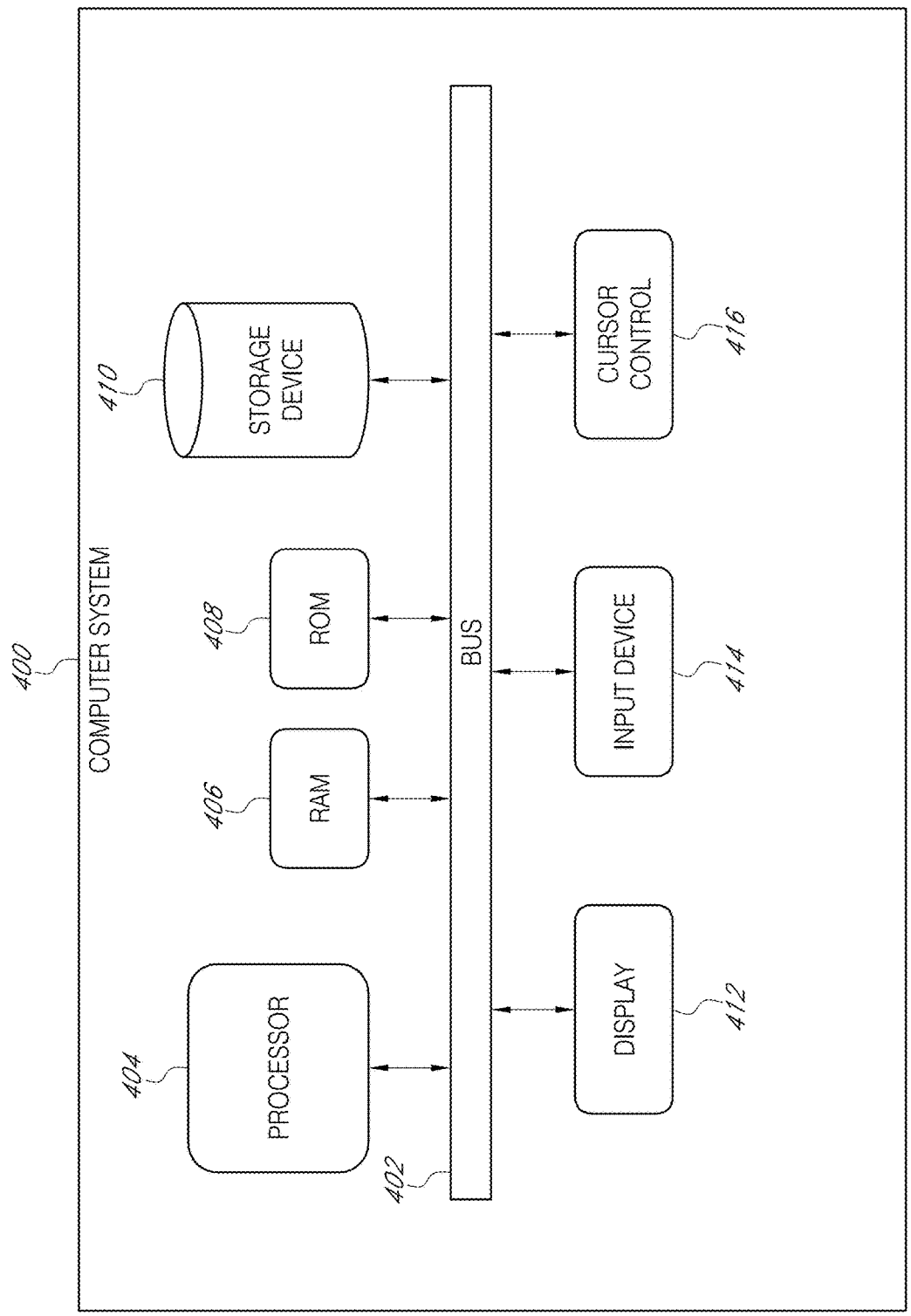
FIG. 4 is a block diagram of a computer system in accordance with various embodiments.

FIG. 4 is a block diagram of a computer system in accordance with various embodiments. Computer system 400 may be an example of one implementation for computing platform 302 described above in FIG. 3.

In one or more examples, computer system 400 can include a bus 402 or other communication mechanism for communicating information, and a processor 404 coupled with bus 402 for processing information. In various embodiments, computer system 400 can also include a memory, which can be a random-access memory (RAM) 406 or other dynamic storage device, coupled to bus 402 for determining instructions to be executed by processor 404. Memory also can be used for storing temporary variables or other intermediate information during execution of instructions to be executed by processor 404. In various embodiments, computer system 400 can further include a read only memory (ROM) 408 or other static storage device coupled to bus 402 for storing static information and instructions for processor 404. A storage device 410, such as a magnetic disk or optical disk, can be provided and coupled to bus 402 for storing information and instructions.

In various embodiments, computer system 400 can be coupled via bus 402 to a display 412, such as a cathode ray tube (CRT) or liquid crystal display (LCD), for displaying information to a computer user. An input device 414, including alphanumeric and other keys, can be coupled to bus 402 for communicating information and command selections to processor 404. Another type of user input device is a cursor control 416, such as a mouse, a joystick, a trackball, a gesture input device, a gaze-based input device, or cursor direction keys for communicating direction information and command selections to processor 404 and for controlling cursor movement on display 412. This input device 414 typically has two degrees of freedom in two axes, a first axis (e.g., x) and a second axis (e.g., y), that allows the device to specify positions in a plane. However, it should be understood that input devices 414 allowing for three-dimensional (e.g., x, y, and z) cursor movement are also contemplated herein.

Consistent with certain implementations of the present teachings, results can be provided by computer system 400 in response to processor 404 executing one or more sequences of one or more instructions contained in RAM 406. Such instructions can be read into RAM 406 from another computer-readable medium or computer-readable storage medium, such as storage device 410. Execution of the sequences of instructions contained in RAM 406 can cause processor 404 to perform the processes described herein. Alternatively, hard-wired circuitry can be used in place of or in combination with software instructions to implement the present teachings. Thus, implementations of the present teachings are not limited to any specific combination of hardware circuitry and software.

The term "computer-readable medium" (e.g., data store, data storage, storage device, data storage device, etc.) or "computer-readable storage medium" as used herein refers to any media that participates in providing instructions to processor 404 for execution. Such a medium can take many forms, including but not limited to, non-volatile media, volatile media, and transmission media. Examples of non-volatile media can include, but are not limited to, optical, solid state, magnetic disks, such as storage device 410. Examples of volatile media can include, but are not limited to, dynamic memory, such as RAM 406. Examples of transmission media can include, but are not limited to, coaxial cables, copper wire, and fiber optics, including the wires that comprise bus 402.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In addition to computer readable medium, instructions or data can be provided as signals on transmission media included in a communications apparatus or system to provide sequences of one or more instructions to processor 404 of computer system 400 for execution. For example, a communication apparatus may include a transceiver having signals indicative of instructions and data. The instructions and data are configured to cause one or more processors to implement the functions outlined in the disclosure herein. Representative examples of data communications transmission connections can include, but are not limited to, telephone modem connections, wide area networks (WAN), local area networks (LAN), infrared data connections, NFC connections, optical communications connections, etc.

It should be appreciated that the methodologies described herein, flow charts, diagrams, and accompanying disclosure can be implemented using computer system 400 as a standalone device or on a distributed network of shared computer processing resources such as a cloud computing network.

The methodologies described herein may be implemented by various means depending upon the application. For example, these methodologies may be implemented in hardware, firmware, software, or any combination thereof. For a hardware implementation, the processing unit may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic devices, other electronic units designed to perform the functions described herein, or a combination thereof.

In various embodiments, the methods of the present teachings may be implemented as firmware and/or a software program and applications written in conventional programming languages such as C, C++, Python, etc. If implemented as firmware and/or software, the embodiments described herein can be implemented on a non-transitory computer-readable medium in which a program is stored for causing a computer to perform the methods described above. It should be understood that the various engines described herein can be provided on a computer system, such as computer system 400, whereby processor 404 would execute the analyses and determinations provided by these engines, subject to instructions provided by any one of, or a combination of, the memory components RAM 406, ROM, 408, or storage device 410 and user input provided via input device 414.

Figure 5:
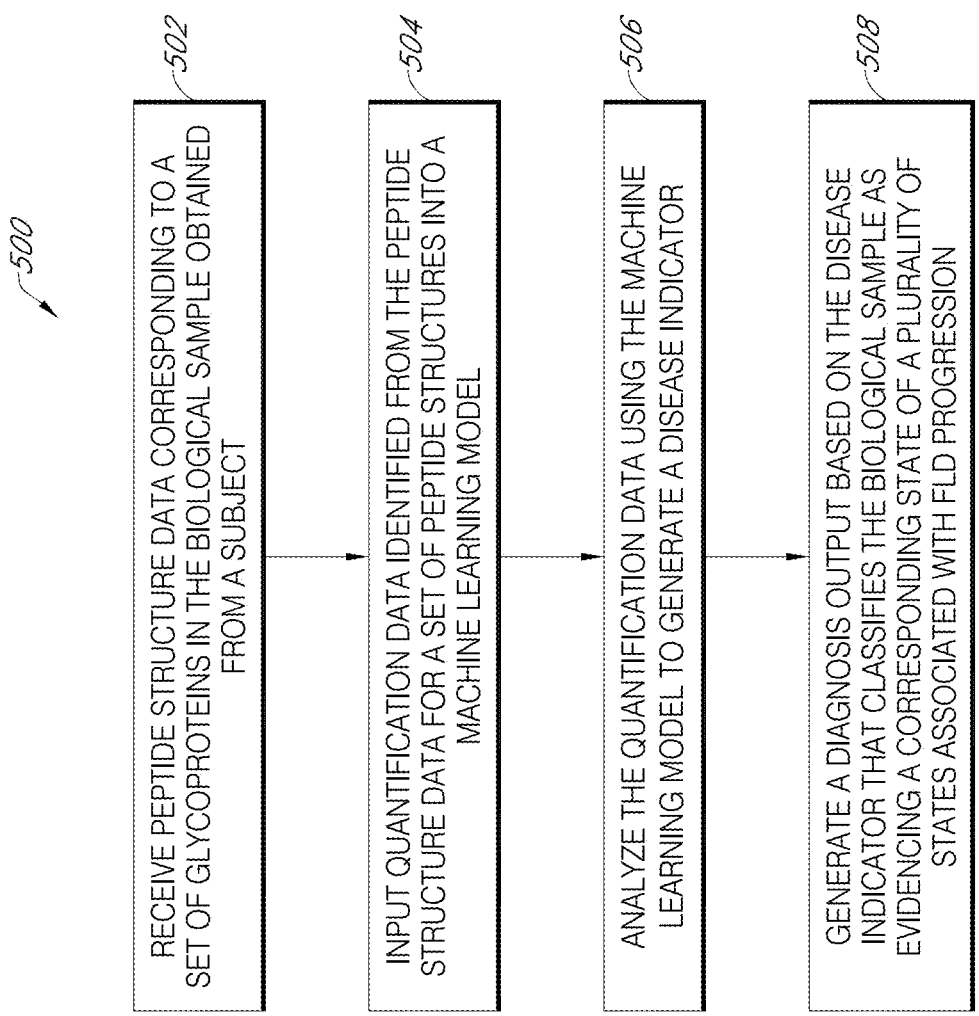
FIG. 5 is a flowchart of a process for evaluating a biological sample obtained from a subject with respect to an FLD progression in accordance with one or more embodiments.

VI. Exemplary Methodologies Relating to Diagnosis Based on Peptide Structure Data Analysis VI.A. General Methodology FIG. 5 is a flowchart of a process for classifying a biological sample obtained from a subject with respect to a plurality of states associated with fatty liver (FLD) progression. Process 500 may be implemented using, for example, at least a portion of workflow 100 as described in FIGS. 1, 2A, and 2B and/or analysis system 300 as described in FIG. 3. Process 500 may be used to generate a diagnosis output such as, for example, diagnosis output 324 in FIG. 3.

Step 502 includes receiving peptide structure data corresponding to a set of glycoproteins in the biological sample obtained from a subject. The peptide structure data may be, for example, one example of an implementation of peptide structure data 310 in FIG. 3. The peptide structure data may include quantification data for each peptide structure of a plurality of peptide structures. The peptide structure data may have been generated using, for example, without limitation, multiple reaction monitoring mass spectrometry (MRM-MS). In one or more embodiments, the peptide structure data includes quantification data for the plurality of peptide structures. This quantification data for a peptide structure may include, for example, without limitation, at least one of an abundance, a relative abundance, a normalized abundance, a relative quantity, an adjusted quantity, a normalized quantity, a relative concentration, an adjusted concentration, or a normalized concentration for the peptide structure.

In one or more embodiments, the peptide structure data is generated for a sample created from the biological sample. For example, the biological sample may be prepared using reduction, alkylation, and enzymatic digestion to form a prepared sample. The prepared sample includes the plurality of peptide structures for which the peptide structure data is generated and then received in step 502.

Step 504 includes inputting quantification data identified from the peptide structure data for a set of peptide structures into a machine learning model. In some embodiments, the set of peptide structures includes at least one peptide structure identified from a plurality of peptide structures in Table 1 above. In various embodiments, at least one peptide structure comprises a glycopeptide structure defined by a peptide sequence and a glycan structure linked to the peptide sequence at a linking site of the peptide sequence, as identified in Table 1.

The quantification data may include, for example, one or more quantification metrics for each peptide structure of the plurality of peptide structures. A quantification metric for a peptide structure may be, for example, but is not limited to, a relative quantity, an adjusted quantity, a normalized quantity, a relative concentration, an adjusted concentration, or a normalized concentration. In this manner, the quantification data for a given peptide structure provides an indication of the abundance of the peptide structure in the biological sample. The machine learning model may be, for example, a supervised machine learning model.

Step 506 includes analyzing the quantification data using the machine learning model to generate a disease indicator. In various embodiments, the disease indicator that is generated may include an indication of whether the biological sample evidences a state associated with FLD progression. For example, the disease indicator may indicate whether the biological sample is likely positive for NASH or HCC or is likely healthy or non-NASH/HCC (e.g., may be indicative of a benign hepatic mass). In various embodiments, the disease indicator comprises a probability that the biological sample evidences a NASH state or a probability that the biological sample evidences an HCC state. In one or more embodiments, the machine learning model may generate an output that classifies the biological sample as positive for the NASH state, positive for the HCC state, or positive for a healthy (or non-NASH/HCC) state. In various embodiments, the disease indicator can be a score.

Step 508 includes generating a diagnosis output based on the disease indicator that classifies the biological sample as evidencing a corresponding state of a plurality of states associated with the FLD progression. In various embodiments, the plurality of states can include a NASH state and a hepatocellular carcinoma (HCC) state. In some embodiments, the plurality of states can include a non-NASH/HCC state that comprises at least one of a healthy state, a benign hepatic mass state, a liver disease-free state, or some other type non-NASH/HCC state.

When the disease indicator is a score, step 508 may include determining that the score falls within a selected range associated with the corresponding state of the plurality of states (e.g., between 0.0 and 0.05 for the non-NASH/HCC state, between 0.05 and 0.4 for the NASH state, and between 0.4 and 1.0 for the HCC state). In some embodiments, step 506 may include determining that the biological sample evidences the corresponding state based on a determination that the score falls within the selected range associated with corresponding state.

In one or more embodiments, generating the diagnosis output in step 508 includes generating the diagnosis output as part of a report that identifies the corresponding state. In some embodiments, step 508 may also include generating a treatment output based on at least one of the diagnosis output or the disease indicator. In some embodiments, the treatment output comprises at least one of an identification of a treatment to treat the subject, a design for the treatment, a manufacturing plan for the treatment, or a treatment plan for administering the treatment.

For a subject that has been diagnosed with NASH, the treatment may include, for example, a therapeutic dosage of at least one of Obeticholic acid (OCA), Tropifexor, Elafibranor, Saroglitazar, Aramchol, Semaglutide, Tirzepatide, Cotadutide, NGM282, MSDC-0602K, Resmetirom, Cenicriviroc, Selonsertib, Emricasan, Simtuzumab, and GR-MD-02. For a subject that has been diagnosed with NASH, the treatment may include, for example, a therapeutic dosage of at least one of Atezolizumab, Bevacizumab, Sorafenib, Lenvatinib, Nivolumab, Regorafenib, Cabozantinib, Pemigatinib, Ramucirumab, or Pembrolizumab.

Figure 6:
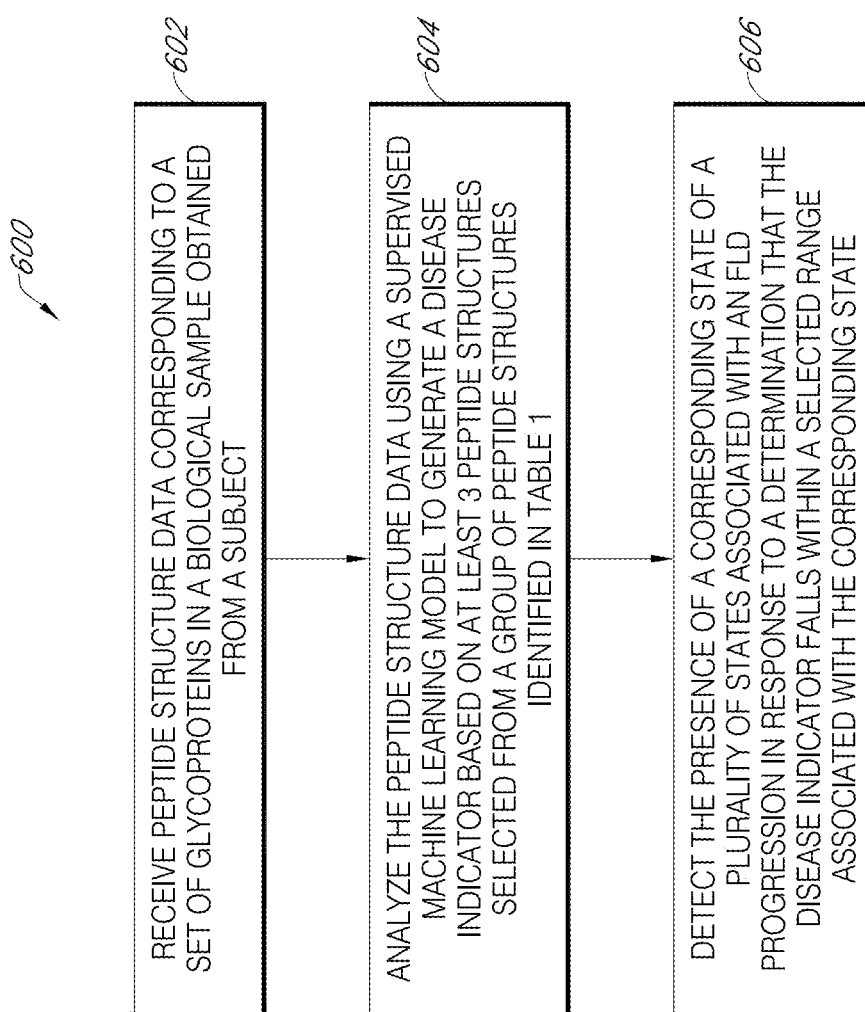
FIG. 6 is a flowchart of a process for detecting the presence of a disease state associated with an FLD progression in accordance with one or more embodiments.

FIG. 6 is a flowchart of a process for detecting a presence of one of a plurality of states associated with fatty liver disease (FLD) progression in a biological sample. Process 600 may be implemented using, for example, at least a portion of workflow 100 as described in FIGS. 1, 2A, and 2B and/or analysis system 300 as described in FIG. 3.

Step 602 includes receiving peptide structure data corresponding to a set of glycoproteins in the biological sample obtained from a subject. The peptide structure data may have been generated from a prepared sample using, for example, multiple reaction monitoring mass spectrometry (MRM-MS). The peptide structure data may include quantification data for each peptide structure of a panel of peptide structures. The quantification data for a peptide structure of the plurality of peptide structures may include at least one of a relative quantity, an adjusted quantity, a normalized quantity, a relative concentration, an adjusted concentration, a normalized concentration, or another quantification metric.

Step 604 includes analyzing the peptide structure data using a supervised machine learning model to generate a disease indicator based on at least 3 peptide structures selected from a group of peptide structures identified in Table 1. In one or more embodiments, the supervised machine learning model comprises a logistic regression model.

In various embodiments, the at least 3 peptide structures comprises a glycopeptide structure defined by a peptide sequence and a glycan structure linked to the peptide sequence at a linking site of the peptide sequence, as identified in Table 1, with the peptide sequence being one of SEQ ID NOS: 23, 24, 25, 29, 30, 31, 33, 35, 36, 37, 38, 39, 40, 41, 42, 43, 44, 45, 46, 47, 48, 49, 50, or 51 as defined in Table 1.

In one or more embodiments, the at least 3 peptide structures include only peptide structures fragmented from alpha-2-macroglobulin (A2MG). In one or more embodiments, the at least 3 peptide structures include only peptide structures fragmented from the alpha-1-acid glycoprotein 1 (AGP1). In one or more embodiments, the at least 3 peptide structures include only peptide structures fragmented from haptoglobin (HPT). In one or more embodiments, the at least 3 peptide structures include only peptide structures fragmented from Complement Factor H (CFAH). In one or more embodiments, the at least 3 peptide structures include only peptide structures fragmented from alpha-1-antitrypsin (A1AT).

In various embodiments, step 604 may include computing a peptide structure profile for the biological sample that identifies a weighted value for each peptide structure of the at least 3 peptide structures. In some embodiments, the weighted value for a peptide structure of the at least 3 peptide structures can be a product of a quantification metric for the peptide structure identified from the peptide structure data and a weight coefficient for the peptide structure. The weight coefficient of a corresponding peptide structure of the at least 3 peptide structures may indicate the relative significance of the corresponding peptide structure to the disease indicator. In one or more embodiments, analyzing the peptide structure data comprises computing the disease indicator using the peptide structure profile. The disease indicator may be, for example, a score that that indicates which state of a plurality of states is evidenced by the biological sample.

In one or more embodiments, the supervised machine learning model employs 3 different models in generating the final disease indicator. These three models may each be, for example, a regression model that is used to analyze the peptide structure quantification data for a particular state versus the other states. For example, each of these 3 regression models may be used to distinguish between a given state of the plurality of states and the other states of the plurality of states.

In one or more embodiments, the at least 3 peptide structures of step 604 may be selected from those peptide structures identified in Table 2 below, where Table 2 includes a subset of the peptide structures identified in Table 1. Table 2 further identifies the weight coefficients associated with distinguishing between the NASH state versus the other states (e.g., HCC state and control state), between the HCC state versus the other states (e.g., the NASH state and the control state), and between the control state versus the other states (e.g., the NASH state and the HCC state).

TABLE 2

Peptide Structures and Associated Coefficients

| PS-ID NO. | Peptide Structure (PS) NAME | (Protein) SEQ ID NO. | (Peptide) SEQ ID NO. | Coefficients (Control v. Rest) | Coefficients (NASH v. Rest) | Coefficients (HCC v. Rest) |
|---|---|---|---|---|---|---|
| PS-1 | A1AT (271) - 5401 | 1 | 23 | 0.514 | 0.013 | 0.412 |
| PS-2 | A1AT (271) - 5402 | 1 | 23 | 0.416 | 0.099 | 0.369 |

TABLE 2-continued

Peptide Structures and Associated Coefficients

| PS-ID NO. | Peptide Structure (PS) NAME | (Protein) SEQ ID NO. | (Peptide) SEQ ID NO. | Coefficients (Control v. Rest) | Coefficients (NASH v. Rest) | Coefficients (HCC v. Rest) |
|---|---|---|---|---|---|---|
| PS-3 | A1BG (179) - 5402 | 2 | 24 | 0.105 | 0.17 | 0.056 |
| PS-8 | A2MG (247) - 5402 | 3 | 28 | 0.021 | 0.045 | 0.235 |
| PS-9 | A2MG (55) - 5402 | 3 | 28 | 0.209 | 0.108 | 0.327 |
| PS-13 | A2MG (869) - 6200 | 3 | 30 | 0.111 | 0.576 | 0.435 |
| PS-17 | AACT (106) - 7604 | 4 | 32 | 0.353 | 0.287 | 0.0507 |
| PS-18 | AGP1 (33) - 5402 | 6 | 33 | 0.113 | 0.138 | 0.11 |
| PS-20 | AGP1 (93) - 6502 | 6 | 35 | 0.378 | 0.119 | 0.701 |
| PS-21 | APOC3 (74) - 1102 | 7 | 36 | 0.551 | 0.312 | 0.123 |
| PS-22 | APOC3 (74) - 1202 | 7 | 36 | 0.39 | 0.31 | 0.071 |
| PS-23 | APOC3 (74) - 1300 | 7 | 36 | 0.293 | −1.44 | 0.588 |
| PS-24 | APOC3 (74) - 2110 | 7 | 36 | 0.798 | 0.55 | 0.391 |
| PS-25 | APOM (135) - 5421 | 8 | 37 | 0.707 | 0.14 | 0.624 |
| PS-26 | CFAI (70) - 5401 | 9 | 38 | 0.389 | 0.68 | 0.075 |
| PS-27 | CLUS (374) - 6501 | 10 | 39 | 0.669 | 1.119 | 0.644 |
| PS-28 | CO4A (1328) - 5402 | 11 | 40 | 0.535 | 0.398 | 0.45 |
| PS-29 | CO6 (324) - 5200 | 13 | 41 | 0.037 | 0.295 | 0.082 |
| PS-30 | CO6 (324) - 5400 | 12 | 41 | 0.025 | 0.186 | 0.101 |
| PS-31 | CO8A (437) - 5200 | 13 | 42 | 0.443 | 0.277 | 0.974 |
| PS-32 | CO8A (437) - 5410 | 13 | 42 | 0.884 | 0.274 | 0.122 |
| PS-34 | HPT (207) - 11904 | 14 | 43 | 0.265 | 0.769 | −1.036 |
| PS-35 | HPT (207) - 121005 | 14 | 43 | 0.304 | 0.335 | 0.606 |
| PS-37 | HPT (241) - 5401 | 14 | 44 | 0.417 | 0.104 | 0.743 |
| PS-38 | HPT (241) - 5402 | 14 | 44 | 0.051 | 0.907 | 0.131 |
| PS-39 | HPT (241) - 5511 | 14 | 44 | 0.428 | 0.318 | 0.249 |
| PS-40 | HPT (241) - 6502 | 14 | 45 | 0.986 | 0.417 | 0.508 |
| PS-41 | IGA2 (205) - 5510 | 15 | 46 | 1.463 | 0.592 | 0.558 |
| PS-42 | IGG2 (297) - 4400 | 16 | 46 | 0.975 | 0.906 | 0.847 |
| PS-43 | IGG2 (297) - 4411 | 17 | 46 | 0.272 | 0.371 | 0.181 |
| PS-44 | IGM (209) - 5401 | 18 | 47 | 0.682 | 0.17 | 0.266 |
| PS-45 | KLKB1 (494) - 5401 | 19 | 48 | 0.459 | 0.017 | 0.086 |
| PS-46 | KLKB1 (494) - 5402 | 19 | 48 | 0.068 | 0.223 | 0.331 |
| PS-47 | KLKB1 (494) - 5410 | 19 | 48 | 1.11 | 0.037 | 0.829 |
| PS-48 | KLKB1 (494) - 6503 | 19 | 48 | 0.231 | 0.707 | 0.646 |
| PS-49 | TRFE (432) - 5402 | 20 | 49 | 0.311 | 0.938 | 1.004 |
| PS-50 | TRFE (432) - 6501 | 20 | 49 | 0.337 | 0.204 | 0.146 |
| PS-51 | TRFE (432) - 6502 | 20 | 49 | 0.107 | 0.539 | 0.2 |
| PS-52 | VTNC (169) - 5401 | 21 | 50 | 0.551 | 0.28 | 0.238 |
| PS-53 | ZA2G (112) - 5402 | 22 | 51 | 0.177 | 0.308 | 0.171 |

Step 606 includes detecting the presence of a corresponding state of the plurality of states associated with the FLD progression in response to a determination that the disease indicator falls within a selected range associated with the corresponding state. In some embodiments, the plurality of states includes at least two selected from a group consisting of a non-alcoholic steatohepatitis (NASH) state, a hepatocellular carcinoma (HCC) state, or a non-NASH/HCC state (e.g., a non-alcoholic fatty liver disease state, a control state, a healthy state, a benign hepatic mass state, a liver disease-free state).

In one or more embodiments, the corresponding state is a non-NASH/HCC state and the selected range for the disease indicator associated with the non-NASH/HCC state is between 0.00 and about 0.05. In some embodiments, the corresponding state is a NASH state and the selected range for the disease indicator associated with the NASH state is between 0.05 and 0.4. In some embodiments, the corresponding state is an HCC state and the selected range for the disease indicator associated with the HCC state is between 0.4 and 1.0.

In one or more embodiments, process 600 may further include generating a report that includes a diagnosis based on the corresponding state detected for the subject. The report may include, for example, the disease indicator.

VI.B. Training a Model

Figure 7:
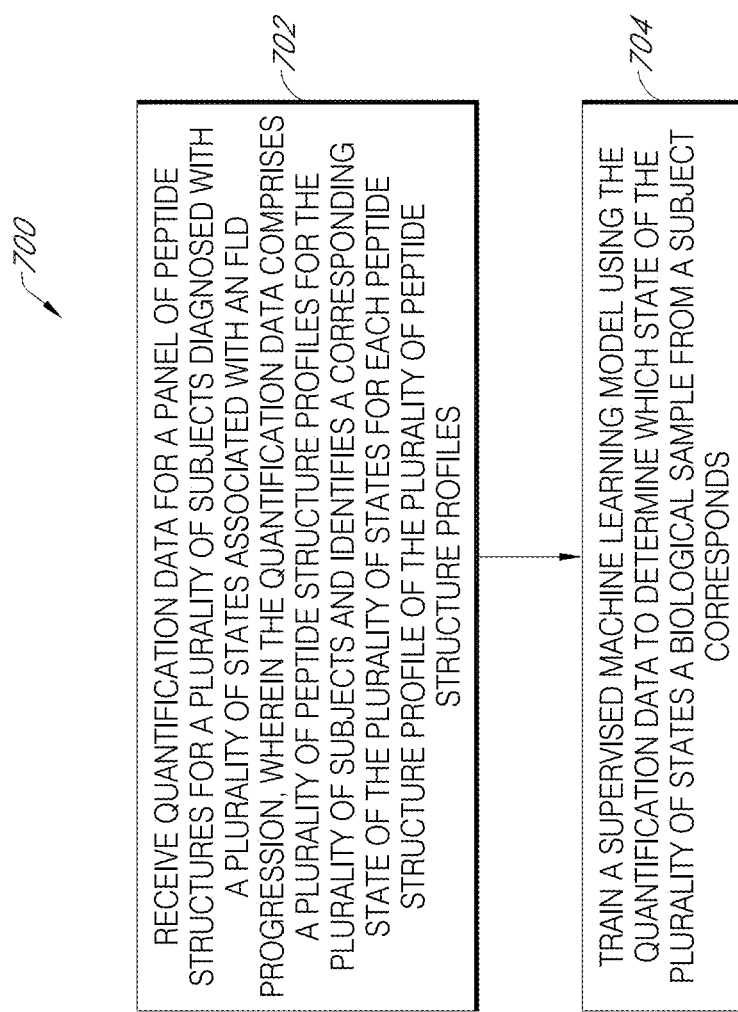
FIG. 7 is a flowchart of a process for training a supervised machine learning model for determining which state of a plurality of states a biological sample corresponds in accordance with various embodiments.

FIG. 7 is a flowchart of a process for training a model to generate a classify a biological sample as belonging to or evidencing one of a plurality of states associated with FLD progression. Process 700 may be implemented using, for example, analysis system 300 as described in FIG. 3. In one or more embodiments, process 700 may be performed to train model 314 in FIG. 3.

Step 702 includes receiving quantification data for a panel of peptide structures for a plurality of subjects diagnosed with the plurality of states associated with the FLD progression, wherein the quantification data comprises a plurality of peptide structure profiles for the plurality of subjects and identifies a corresponding state of the plurality of states for each peptide structure profile of the plurality of peptide structure profiles.

In one or more embodiments, the plurality of peptide structure profiles comprises normalized abundance data for a first number of peptide structures. In one or more embodiments, the quantification data for the panel of peptide structures for the plurality of subjects diagnosed with the plurality of states comprises at least one of an abundance, a relative abundance, a normalized abundance, a relative quantity, an adjusted quantity, a normalized quantity, a relative concentration, an adjusted concentration, or a normalized concentration.

Step 704 includes training a supervised machine learning model using the quantification data to determine which state of the plurality of states a biological sample from a subject corresponds. In various embodiments, the supervised machine learning model comprises a logistic regression model. In one or more embodiments, the logistic regression model may be a LASSO regularization model. The plurality of states may include, for example, at least one of a NASH state, an HCC state, or a non-NASH/HCC state.

In one or more embodiments, step 704 may include, for example, training the supervised machine learning model to make the determination of state based on the quantification data for at least 3 peptide structures from the list of peptide structures identified in Table 1 or in Table 2 above.

The peptide structures selected for training may be peptide structures identified from, for example, a differential expression analysis performed using initial training data to compare the quantification data for peptide structures for a first portion of the plurality of subjects diagnosed with NASH, a second portion of the plurality of subjects diagnosed with HCC, and a third portion of the plurality of subjects diagnosed with a non-NASH/HCC condition (e.g., a healthy state, a benign hepatic mass, liver disease-free state, etc.).

For example, comparisons may be performed to compare peptide structure quantification data between the first portion of subjects with NASH versus the third portion of subjects with the non-NASH/HCC condition (e.g., the control state), to compare the second portion of subjects with HCC versus the first portion of subjects with NASH, and/or to compare the first portion of subjects with NASH versus the second portion of subjects with HCC. In some embodiments, the comparisons may be normalized and compared to one another.

Tables 3A-3C below indicates the fold changes (FC), false discovery rates (FDR), and p-values computed based on such comparisons.

TABLE 3A

Differential Expression Analysis for NASH v. Control

| PS-ID NO. | PS NAME | NASH/ Control (fold change) | NASH/ Control (FDR) | NASH/ Control (p-value) |
|---|---|---|---|---|
| PS-1 | A1AT 271) - 5401 | 0.85 | 0.005 | <0.001 |
| PS-2 | A1AT (271) - 5402 | 0.87 | <0.001 | <0.001 |
| PS-3 | A1BG (179) - 5402 | 1.17 | 0.003 | <0.001 |
| PS-9 | A2MG (247) - 5402 | 1.23 | 0.002 | <0.001 |
| PS-10 | A2MG (55) - 5402 | 1.17 | 0.016 | 0.003 |
| PS-14 | A2MG (869) - 6200 | 0.87 | 0.049 | 0.013 |
| PS-17 | AACT (106) - 7604 | 0.45 | 0.001 | <0.001 |
| PS-19 | AGP1 (33) - 5402 | 0.72 | 0.003 | <0.001 |
| PS-20 | AGP1 (93) - 6502 | 0.82 | 0.038 | 0.009 |
| PS-21 | APOC3 (74) - 1102 | 1.53 | <0.001 | <0.001 |
| PS-22 | APOC3 (74) - 1202 | 1.73 | 0.008 | 0.001 |
| PS-23 | APOC3 (74) - 1300 | 2.01 | 0.005 | <0.001 |
| PS-24 | APOC3 (74) - 2110 | 1.93 | <0.001 | <0.001 |
| PS-25 | APOM (135) - 5421 | 1.62 | 0.049 | 0.014 |
| PS-26 | CFAI (70) - 5401 | 0.76 | 0.024 | 0.004 |
| PS-27 | CLUS (374) - 6501 | 1.46 | 0.005 | <0.001 |
| PS-28 | CO4A (1328) - 5402 | 1.17 | <0.001 | <0.001 |
| PS-29 | CO6 (324) - 5200 | 1.57 | 0.025 | 0.005 |
| PS-30 | CO6 (324) - 5400 | 1.76 | 0.01 | 0.002 |
| PS-31 | CO8A (437) - 5200 | 0.72 | 0.043 | 0.011 |
| PS-32 | CO8A (437) - 5410 | 1.43 | 0.035 | 0.008 |
| PS-34 | HPT (207) - 11904 | 0.82 | 0.031 | 0.006 |
| PS-35 | HPT (207) - 121005 | 0.72 | 0.025 | 0.005 |
| PS-36 | HPT (241) - 5401 | 0.76 | 0.033 | 0.007 |

TABLE 3A-continued

Differential Expression Analysis for NASH v. Control

| PS-ID NO. | PS NAME | NASH/ Control (fold change) | NASH/ Control (FDR) | NASH/ Control (p-value) |
|---|---|---|---|---|
| PS-37 | HPT (241) - 5402 | 0.8 | <0.001 | <0.001 |
| PS-38 | HPT (241) - 5511 | 0.88 | 0.027 | 0.005 |
| PS-39 | HPT (241) - 6502 | 1.25 | 0.021 | 0.004 |
| PS-40 | IGA2 (205) - 5510 | 0.42 | 0.016 | 0.003 |
| PS-42 | IGG2 (297) - 4400 | 0.69 | 0.022 | 0.004 |
| PS-43 | IGG2 (297) - 4411 | 1.24 | 0.035 | 0.008 |
| PS-44 | IGM (209) - 5401 | 1.5 | 0.016 | 0.003 |
| PS-45 | KLKB1 (494) - 5401 | 1.7 | 0.001 | <0.001 |
| PS-46 | KLKB1 (494) - 5402 | 1.84 | 0.017 | 0.003 |
| PS-47 | KLKB1 (494) - 5410 | 1.27 | 0.041 | 0.01 |
| PS-48 | KLKB1 (494) - 6503 | 1.51 | 0.002 | <0.001 |
| PS-49 | TRFE (432) - 5402 | 1.19 | 0.008 | 0.001 |
| PS-50 | TRFE (432) - 6501 | 1.24 | 0.001 | <0.001 |
| PS-51 | TRFE (432) - 6502 | 1.13 | 0.049 | 0.013 |
| PS-52 | VTNC (169) - 5401 | 0.71 | 0.002 | <0.001 |
| PS-53 | ZA2G (112) - 5402 | 1.49 | 0.034 | 0.008 |

TABLE 3B

Differential Expression Analysis for HCC v. Control

| PS-ID NO. | PS-NAME | HCC/ control (fold change) | HCC/ Control (FDR) | HCC/ Control (p-value) |
|---|---|---|---|---|
| PS-1 | A1AT (271) - 5401 | 0.79 | <0.001 | <0.001 |
| PS-2 | A1AT (271) - 5402 | 0.82 | <0.001 | <0.001 |
| PS-3 | A1BG (179) - 5402 | 1.28 | <0.001 | <0.001 |
| PS-9 | A2MG (247) - 5402 | 1.47 | <0.001 | <0.001 |
| PS-10 | A2MG (55) - 5402 | 1.34 | <0.001 | <0.001 |
| PS-14 | A2MG (869) - 6200 | 0.68 | <0.001 | <0.001 |
| PS-17 | AACT (106) - 7604 | 0.63 | 0.009 | 0.003 |
| PS-19 | AGP1 (33) - 5402 | 0.75 | 0.008 | 0.002 |
| PS-20 | AGP1 (93) - 6502 | 0.69 | <0.001 | <0.001 |
| PS-21 | APOC3 (74) - 1102 | 1.77 | <0.001 | <0.001 |
| PS-22 | APOC3 (74) - 1202 | 2.55 | <0.001 | <0.001 |
| PS-23 | APOC3 (74) - 1300 | 7.53 | <0.001 | <0.001 |
| PS-24 | APOC3 (74) - 2110 | 2.98 | <0.001 | <0.001 |
| PS-25 | APOM (135) - 5421 | 2.3 | 0.002 | <0.001 |
| PS-26 | CFAI (70) - 5401 | 0.74 | 0.0124 | 0.004 |
| PS-27 | CLUS (374) - 6501 | 1.53 | 0.003 | <0.001 |
| PS-28 | CO4A (1328) - 5402 | 1.39 | <0.001 | <0.001 |
| PS-29 | CO6 (324) - 5200 | 2.42 | <0.001 | <0.001 |
| PS-30 | CO6 (324) - 5400 | 1.9 | 0.023 | 0.008 |
| PS-31 | CO8A (437) - 5200 | 0.57 | <0.001 | <0.001 |
| PS-32 | CO8A (437) - 5410 | 1.75 | 0.006 | 0.002 |
| PS-34 | HPT (207) - 11904 | 0.54 | <0.001 | <0.001 |
| PS-35 | HPT (207) - 121005 | 0.56 | <0.001 | <0.001 |
| PS-36 | HPT (241) - 5401 | 0.55 | <0.001 | <0.001 |
| PS-37 | HPT (241) - 5402 | 0.75 | <0.001 | <0.001 |
| PS-38 | HPT (241) - 5511 | 0.85 | 0.008 | 0.002 |
| PS-39 | HPT (241) - 6502 | 1.68 | <0.001 | <0.001 |
| PS-40 | IGA2 (205) - 5510 | 0.08 | <0.001 | <0.001 |
| PS-42 | IGG2 (297) - 4400 | 0.52 | <0.001 | <0.001 |
| PS-43 | IGG2 (297) - 4411 | 1.59 | <0.001 | <0.001 |
| PS-44 | IGM (209) - 5401 | 1.47 | 0.031 | 0.011 |
| PS-45 | KLKB1 (494) - 5401 | 2.87 | <0.001 | <0.001 |
| PS-46 | KLKB1 (494) - 5402 | 2.99 | <0.001 | <0.001 |
| PS-47 | KLKB1 (494) - 5410 | 1.79 | <0.001 | <0.001 |
| PS-48 | KLKB1 (494) - 6503 | 1.6 | <0.001 | <0.001 |
| PS-49 | TRFE (432) - 5402 | 1.66 | <0.001 | <0.001 |
| PS-50 | TRFE (432) - 6501 | 1.47 | <0.001 | <0.001 |
| PS-51 | TRFE (432) - 6502 | 1.42 | <0.001 | <0.001 |
| PS-52 | VTNC (169) - 5401 | 0.54 | <0.001 | <0.001 |
| PS-53 | ZA2G (112) - 5402 | 2.06 | <0.001 | <0.001 |

TABLE 3C

Differential Expression Analysis for NASH v. HCC

| PS-ID NO. | PS-NAME | NASH/HCC (fold change) | NASH/HCC (FDR) | NASH/HCC (p-value) |
|---|---|---|---|---|
| PS-1 | A1AT (271) - 5401 | 0.94 | 0.499 | 0.323 |
| PS-2 | A1AT (271) - 5402 | 0.95 | 0.499 | 0.319 |
| PS-3 | A1BG (179) - 5402 | 1.12 | 0.29 | 0.134 |
| PS-9 | A2MG (247) - 5402 | 1.134 | 0.153 | 0.051 |
| PS-10 | A2MG (55) - 5402 | 1.1 | 0.371 | 0.186 |
| PS-14 | A2MG (869) - 6200 | 0.85 | 0.23 | 0.095 |
| PS-17 | AACT (106) - 7604 | 1.43 | 0.466 | 0.281 |
| PS-19 | AGP1 (33) - 5402 | 1 | 0.989 | 0.979 |
| PS-20 | AGP1 (93) - 6502 | 0.88 | 0.464 | 0.2767 |
| PS-21 | APOC3 (74) - 1102 | 1.11 | 0.576 | 0.412 |
| PS-22 | APOC3 (74) - 1202 | 1.22 | 0.499 | 0.319 |
| PS-23 | APOC3 (74) - 1300 | 2.51 | 0.013 | 0.0003 |
| PS-24 | APOC3 (74) - 2110 | 1.43 | 0.228 | 0.094 |
| PS-25 | APOM (135) - 5421 | 1.29 | 0.23 | 0.097 |
| PS-26 | CFAI (70) - 5401 | 1.06 | 0.733 | 0.597 |
| PS-27 | CLUS (374) - 6501 | 1.045 | 0.844 | 0.792 |
| PS-28 | CO4A (1328) - 5402 | 1.19 | 0.013 | 0.0004 |
| PS-29 | CO6 (324) - 5200 | 1.41 | 0.135 | 0.04 |
| PS-30 | CO6 (324) - 5400 | 0.97 | 0.923 | 0.899888442 |
| PS-31 | CO8A (437) - 5200 | 0.88 | 0.614 | 0.449 |
| PS-32 | CO8A (437) - 5410 | 1.22 | 0.55 | 0.377 |
| PS-34 | HPT (207) - 11904 | 0.63 | 0.013 | 0.0004 |
| PS-35 | HPT (207) - 121005 | 0.78 | 0.341 | 0.164 |
| PS-36 | HPT (241) - 5401 | 0.77 | 0.152 | 0.051 |
| PS-37 | HPT (241) - 5402 | 0.93 | 0.356 | 0.175 |
| PS-38 | HPT (241) - 5511 | 0.94 | 0.341 | 0.165 |
| PS-39 | HPT (241) - 6502 | 1.37 | 0.102 | 0.024 |
| PS-40 | IGA2 (205) - 5510 | 0.25 | 0.222 | 0.09 |
| PS-42 | IGG2 (297) - 4400 | 0.89 | 0.385 | 0.203 |
| PS-43 | IGG2 (297) - 4411 | 1.29 | 0.102 | 0.024 |
| PS-44 | IGM (209) - 5401 | 1.11 | 0.689 | 0.55 |
| PS-45 | KLKB1 (494) - 5401 | 1.51 | 0.141 | 0.045 |
| PS-46 | KLKB1 (494) - 5402 | 1.52 | 0.371 | 0.186 |
| PS-47 | KLKB1 (494) - 5410 | 1.42 | 0.072 | 0.013 |
| PS-48 | KLKB1 (494) - 6503 | 1.02 | 0.923 | 0.902 |
| PS-49 | TRFE (432) - 5402 | 1.38 | 0.046 | 0.006 |
| PS-50 | TRFE (432) - 6501 | 1.17 | 0.23 | 0.095 |
| PS-51 | TRFE (432) - 6502 | 1.25 | 0.07 | 0.012 |
| PS-52 | VTNC (169) - 5401 | 0.82 | 0.425 | 0.243 |
| PS-53 | ZA2G (112) - 5402 | 1.11 | 0.76 | 0.657 |

VI.C. Combined Training and Diagnosis

The exemplary methodologies described in Section VI. may be used to diagnose a subject who may be suffering from FLD. This diagnosis may be used to determine a method of treatment for a subject. The embodiments described herein may enable faster and more accurate diagnosis of a state of NASH versus HCC. Being able to more quickly and accurately diagnose a subject (or patient) that has advanced from NASH to HCC in the FLD progression may enable treating the subject more quickly, which may lead to a more desirable treatment outcome for the subject. Further, being able to more quickly and accurately determine when a subject has advanced from NASH to HCC may be particularly useful reducing the need for hospitalization and avoidance of death.

Figure 8:
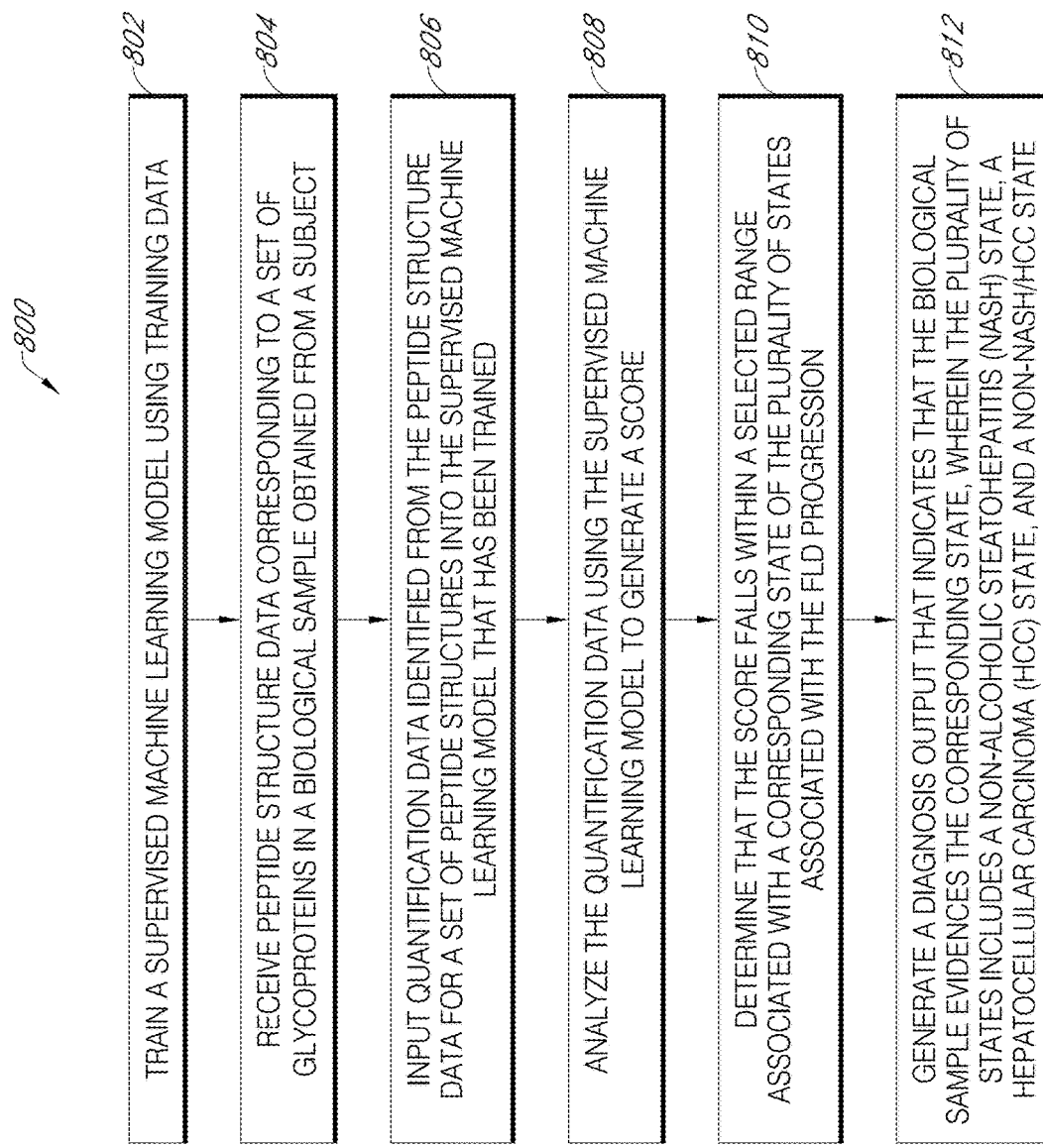
FIG. 8 is a flow chart of a process for classifying a biological sample as corresponding to one of a plurality of states associated with fatty liver disease (FLD) progression in accordance with one or more embodiments.

FIG. 8 is a flow chart of a process for classifying a biological sample as corresponding to one of a plurality of states associated with fatty liver disease (FLD) progression in accordance with one or more embodiments. Process 800 may be implemented using at least a portion of workflow 100 as described FIGS. 1, 2A, and/or 2B and/or analysis system 300 as described in FIG. 3.

Step 802 includes training a supervised machine learning model using training data. In some embodiments, the training data comprises a plurality of peptide structure profiles for a plurality of training subjects and identifies a corresponding state of the plurality of states for each peptide structure profile of the plurality of peptide structure profiles.

Step 804 includes receiving peptide structure data corresponding to a set of glycoproteins in the biological sample obtained from a subject.

Step 806 includes inputting quantification data identified from the peptide structure data for a set of peptide structures into the supervised machine learning model that has been trained. In some embodiments, the set of peptide structures includes at least one peptide structure identified in Table 1.

Step 808 includes analyzing the quantification data using the supervised machine learning model to generate a score.

Step 810 includes determining that the score falls within a selected range associated with a corresponding state of the plurality of states associated with the FLD progression.

Step 812 includes generating a diagnosis output that indicates that the biological sample evidences the corresponding state. In some embodiments, the plurality of states includes a non-alcoholic steatohepatitis (NASH) state, a hepatocellular carcinoma (HCC) state, and a non-NASH/HCC (e.g., control or healthy) state.

VII. Exemplary Methodologies for Treatment

VII.A. Treating NASH

Figure 9:
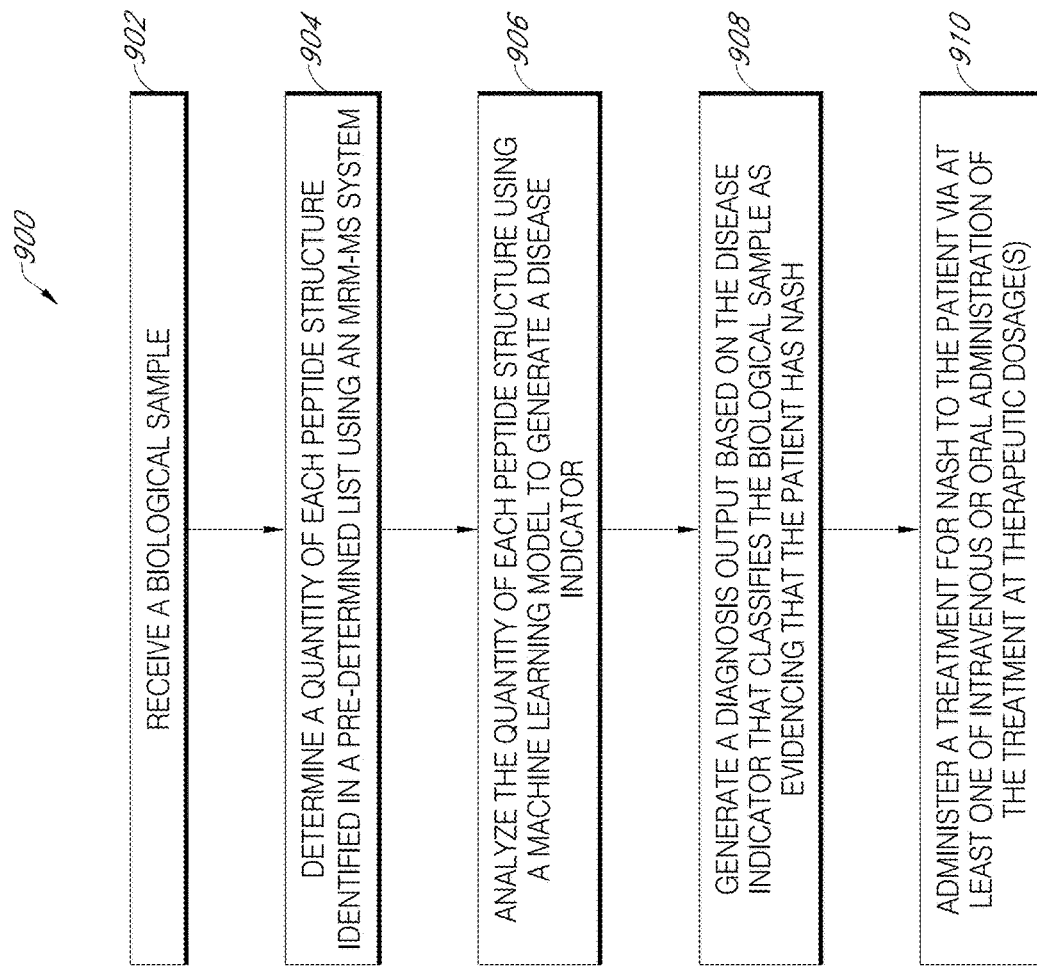
FIG. 9 is a flowchart of a process for treating a subject for NASH in accordance with one or more embodiments.

FIG. 9 is a flowchart of a process for treating a subject for NASH in accordance with one or more embodiments. Process 900 may be at least partially implemented using at least a portion of workflow 100 as described FIGS. 1, 2A, and/or 2B and/or analysis system 300 as described in FIG. 3.

Step 902 includes receiving a biological sample from the patient.

Step 904 includes determining a quantity of each peptide structure identified in a predetermined list using MRM-MS. The predetermined list may be, for example, the list identified in Table 1 or the list identified in Table 2.

Step 906 includes analyzing the quantity of each peptide structure using a machine learning model to generate a disease indicator.

Step 908 includes generating a diagnosis output based on the disease indicator that classifies the biological sample as evidencing that the patient has NASH.

Step 910 includes administering a treatment for NASH to the patient via at least one of intravenous or oral administration of the treatment at therapeutic dosage(s). The treatment may be comprised of one or more therapeutics or derivatives thereof.

The treatment may include, for example, without limitation, at least one compound or derivative thereof selected from the group consisting of Obeticholic acid (OCA), Tropifexor, Elafibranor, Saroglitazar, Aramchol, Semaglutide, Tirzepatide, Cotadutide, NGM282, MSDC-0602K, Resmetirom, Cenicriviroc, Selonsertib, Emricasan, Simtuzumab, and GR-MD-02. In one or more embodiments, a therapeutic dosage for Obeticholic acid (OCA) may include a dosage within a range of 10-25 mg daily.

Process 900 may include one or more additional steps. For example, process 900 may further include designing the therapeutic for treating the subject in response to determining that the biological sample obtained from the subject evidences NASH. Process 900 may include generating a treatment plan for treating the subject in response to determining that the biological sample obtained from the subject evidences NASH.

VII.B. Treating HCC

Figure 10:
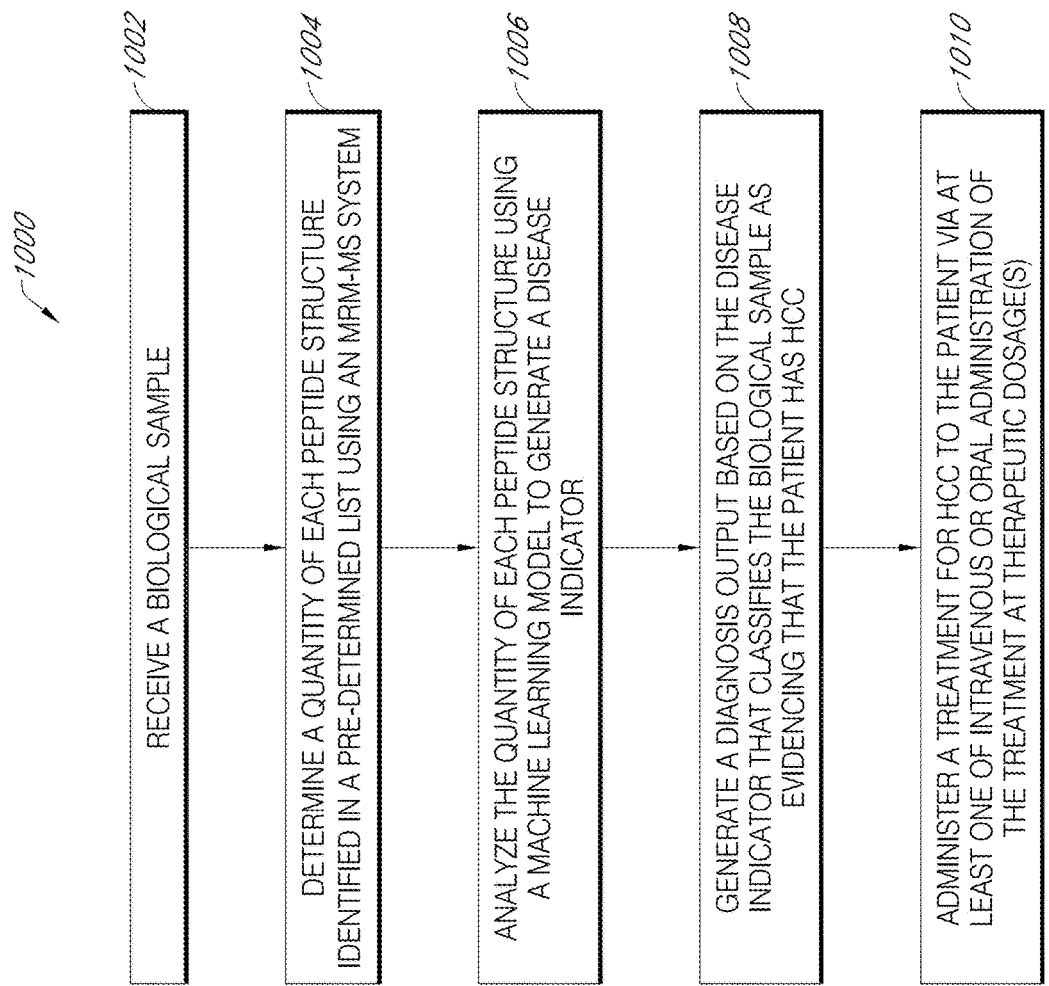
FIG. 10 is a flowchart of a process for treating a subject for NASH in accordance with one or more embodiments.

FIG. 10 is a flowchart of a process for treating a subject for HCC in accordance with one or more embodiments. Process 1000 may be at least partially implemented using at least a portion of workflow 100 as described FIGS. 1, 2A, and/or 2B and/or analysis system 300 as described in FIG. 3.

Step 1002 includes receiving a biological sample from the patient.

Step 1004 includes determining a quantity of each peptide structure identified in a predetermined list using MRM-MS. The predetermined list may be, for example, the list identified in Table 1 or the list identified in Table 2.

Step 1006 includes analyzing the quantity of each peptide structure using a machine learning model to generate a disease indicator.

Step 1008 includes generating a diagnosis output based on the disease indicator that classifies the biological sample as evidencing that the patient has the HCC disorder.

Step 1010 includes administering a treatment for HCC to the patient via at least one of intravenous or oral administration of the treatment at therapeutic dosage(s). The treatment may be comprised of one or more therapeutics or derivatives thereof.

The treatment may include, for example, without limitation, at least one compound or derivative thereof selected from the group consisting of Atezolizumab, Bevacizumab, Sorafenib (e.g., Sorafenib Tosylate), Lenvatinib (e.g., Lenvatinib Mesylate), Nivolumab, Regorafenib, Cabozantinib (e.g., Cabozantinib-S-Malate), Pemigatinib, Ramucirumab, or Pembrolizumab. In one or more embodiments, step 1010 includes administering Sorafenib or a derivative thereof to the patient via at least one of intravenous or oral administration in a range of 775-825 mg daily. In one or more embodiments, step 1010 includes administering Lenvatinib or a derivative thereof to the patient via at least one of intravenous or oral administration in a range of 7.5-8.5 mg/day when the patient weighs <60 kg and 11.5-12.5 mg/day when the patient weighs >60 kg. In one or more embodiments, step 1010 includes administering Nivolumab or a derivative thereof to the patient via at least one of intravenous or oral administration in a range of 0.75-1.25 mg/kg. In one or more embodiments, step 1010 includes administering Regorafenib or a derivative thereof to the patient via oral administration in a range of 150-170 mg/day. In one or more embodiments, step 1010 includes administering Cabozantinib or a derivative thereof to the patient via at least one of intravenous or oral administration in a range of 50-70 mg/day. In one or more embodiments, step 1010 includes administering Ramucirumab or a derivative thereof to the patient via at least one of intravenous or oral administration in a range of 8-12 mg/kg.

Process 1000 may include one or more additional steps. For example, process 1000 may further include designing the therapeutic for treating the subject in response to determining that the biological sample obtained from the subject evidences HCC. Process 900 may include generating a treatment plan for treating the subject in response to determining that the biological sample obtained from the subject evidences HCC.

VIII. Peptide Structure and Product Ion Compositions, Kits and Reagents

Aspects of the disclosure include compositions comprising one or more of the peptide structures listed in Table 1. In some embodiments, a composition comprises a plurality of the peptide structures listed in Table 1. In some embodiments, a composition comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 of the peptide structures listed in Table 1. In some embodiments, a composition comprises a peptide structure having an amino acid sequence with at least 80% sequence identity, such as, for example, at least 81%, 82%, 83%, 84%, 85%, 86%, 87%, 88%, 89%, 90%, 91%, 92%, 93%, 94%, 95%, 96%, 97%, 98%, 99%, or 100% sequence identity to any one of SEQ ID NOs: 23-51, listed in Table 1.

Aspects of the disclosure include compositions comprising one or more precursor ions having a defined charge and/or defined mass-to-charge (m/z) ratio, as listed in Table 4. Aspects of the disclosure include compositions comprising one or more product ions having a defined mass-to-charge (m/z) ratio, which product ions are produced by converting a peptide structure described herein (e.g., a peptide structure listed in Table 1) into a gas phase ion in a mass spectrometry system. Conversion of the peptide structure into a gas phase ion can take place using any of a variety of techniques, including, but not limited to, matrix assisted laser desorption ionization (MALDI); electron ionization (EI); electrospray ionization (ESI); atmospheric pressure chemical ionization (APCI); and/or atmospheric pressure photo ionization (APPI).

Aspects of the disclosure include compositions comprising one or more product ions produced from one or more of the peptide structures described herein (e.g., a peptide structure listed in Table 1). In some embodiments, a composition comprises a set of the product ions listed in Table 4, having an m/z ratio selected from the list provided for each peptide structure in Table 1 or Table 4.

In some embodiments, a composition comprises at least one of peptide structures PS-1 to PS-53 identified in Table 1.

In some embodiments, a composition comprises a peptide structure or a product ion. The peptide structure or product ion comprises an amino acid sequence having at least 90% sequence identity to any one of SEQ ID NOS: 23-51, as identified in Table 5, corresponding to peptide structures PS-1 to PS-53 in Table 1.

In some embodiments, the product ion is selected as one from a group consisting of product ions identified in Table 4, including product ions falling within an identified m/z range of the m/z ratio identified in Table 4 and characterized as having a precursor ion having an m/z ratio within an identified m/z range of the m/z ratio identified in Table 4. A first range for the product ion m/z ratio may be ±0.5. A second range for the product ion m/z ratio may be ±0.8. A third range for the product ion m/z ratio may be ±1.0. A first range for the precursor ion m/z ratio may be ±1.0; a second range for the precursor ion m/z ratio may be (±1.5). Thus, a composition may include a product ion having an m/z ratio that falls within at least one of the first range (±0.5), the second range (±0.8), or the third range (±1.0) of the product ion m/z ratio identified in Table 4, and characterized as having a precursor ion having an m/z ratio that falls within at least one of first range (±0.5), a second range (±1.0), or a third range (±1.0 of the precursor ion m/z ratio identified in Table 4.

TABLE 4

Peptide Structure and Mass Spectrometry-Related Characteristics

| PS-ID NO. | RT (min) | Collision Energy | Precursor m/z | Precursor Charge | 1st Product m/z | 1st Product Charge | 2nd Product m/z | 2nd Product Charge |
|---|---|---|---|---|---|---|---|---|
| PS-1 | 37.5 | 30 | 1224.5 | 3 | 366.1 | 1 | 980 | 2 |
| PS-2 | 38.3 | 24 | 991.2 | 4 | 366.1 | 1 | 980.5 | 2 |
| PS-3 | 33.15 | 15 | 1209.7 | 5 | 1347.9 | 3 | 366.1 | 1 |
| PS-4 | 18.54 | 20 | 628.3 | 2 | 1071.5 | 1 | 738.4 | 1 |
| PS-5 | 32.56 | 30 | 836.9 | 2 | 721.9 | 2 | 1305.7 | 1 |
| PS-6 | 44.1 | 22 | 1093.2 | 4 | 366.1 | 1 | 1183.6 | 2 |
| PS-7 | 38.9 | 25 | 1239.1 | 4 | 1314.2 | 3 | N/A | N/A |
| PS-8 | 39.3 | 30 | 1413.6 | 4 | 366.1 | 1 | 1313.3 | 3 |
| PS-9 | 39.9 | 26 | 1189.2 | 5 | 366.1 | 1 | N/A | N/A |
| PS-10 | 42.1 | 25 | 1151.7 | 4 | 366.1 | 1 | 1300.7 | 2 |
| PS-11 | 41.5 | 22 | 1115.4 | 4 | 366.1 | 1 | N/A | N/A |
| PS-12 | 42 | 25 | 1188.2 | 4 | 366.1 | 1 | N/A | N/A |
| PS-13 | 34.6 | 23 | 1158.8 | 4 | 1206.9 | 3 | 366.1 | 1 |
| PS-14 | 34.5 | 30 | 1199.3 | 4 | 1206.9 | 3 | 366.1 | 1 |
| PS-15 | 34.4 | 24 | 1249.6 | 4 | 366.1 | 1 | 1206.9 | 3 |
| PS-16 | 41.4 | 20 | 1206.3 | 7 | 366.1 | 1 | N/A | N/A |
| PS-17 | 38.4 | 30 | 1184.9 | 5 | 274.1 | 1 | N/A | N/A |
| PS-18 | 11.4 | 20 | 851.1 | 4 | 366.1 | 1 | 1398.6 | 1 |
| PS-19 | 38.1 | 30 | 1196.5 | 4 | 366.1 | 1 | N/A | N/A |
| PS-20 | 23 | 28 | 1122.5 | 4 | 366.1 | 1 | 1060 | 2 |
| PS-21 | 38.2 | 20 | 1028.8 | 3 | 274.1 | 1 | 1069 | 2 |
| PS-22 | 38.1 | 27 | 1096.5 | 3 | 274.1 | 1 | N/A | N/A |
| PS-23 | 37.5 | 23 | 970.1 | 3 | 366.1 | 1 | N/A | N/A |
| PS-24 | 37 | 22 | 937.4 | 3 | 366.1 | 1 | N/A | N/A |
| PS-25 | 34.7 | 36 | 1185.3 | 4 | 366.1 | 1 | N/A | N/A |
| PS-26 | 6.2 | 25 | 993.1 | 3 | 366.1 | 1 | N/A | N/A |
| PS-27 | 23.3 | 33 | 991.4 | 4 | 366.1 | 1 | N/A | N/A |
| PS-28 | 17.5 | 34 | 1103.8 | 3 | 366.1 | 1 | 1307.7 | 1 |
| PS-29 | 15 | 32 | 1020 | 2 | 366.1 | 1 | N/A | N/A |
| PS-30 | 15 | 27 | 815.7 | 3 | 366.1 | 1 | N/A | N/A |
| PS-31 | 14.1 | 45 | 850.7 | 3 | 366.1 | 1 | N/A | N/A |
| PS-32 | 13.5 | 32 | 1034.8 | 3 | 366.1 | 1 | N/A | N/A |
| PS-33 | 13.1 | 27 | 1116.4 | 5 | 366.1 | 1 | N/A | N/A |
| PS-34 | 13.2 | 31 | 1247.7 | 5 | 366.1 | 1 | N/A | N/A |
| PS-35 | 13.3 | 35 | 1378.9 | 5 | 366.1 | 1 | N/A | N/A |
| PS-36 | 29.3 | 31 | 1237.3 | 3 | 366.1 | 1 | 999.5 | 2 |
| PS-37 | 30.5 | 24 | 1001.2 | 4 | 366.1 | 1 | 999.5 | 2 |
| PS-38 | 29.2 | 30 | 1015.5 | 4 | 366.1 | 1 | 999.5 | 2 |
| PS-39 | 30.3 | 20 | 1092.3 | 4 | 366.1 | 1 | N/A | N/A |
| PS-40 | 12.4 | 24 | 977.8 | 3 | 366.1 | 1 | N/A | N/A |
| PS-41 | 8.3 | 27 | 1084.1 | 3 | 366.1 | 1 | 1392.6 | 1 |
| PS-42 | 13.2 | 21 | 873.4 | 3 | 204.1 | 1 | 1360.6 | 1 |
| PS-43 | 14 | 30 | 1019.4 | 3 | 204.1 | 1 | 1360.6 | 1 |
| PS-44 | 25.5 | 30 | 1064.4 | 4 | 366.1 | 1 | 1271.6 | 2 |
| PS-45 | 31.9 | 25 | 1041.5 | 4 | 366.1 | 1 | N/A | N/A |
| PS-46 | 33.1 | 35 | 1114.2 | 4 | 204.1 | 1 | 1225.6 | 2 |
| PS-47 | 30.4 | 20 | 1004.7 | 4 | 366.1 | 1 | N/A | N/A |
| PS-48 | 33.7 | 38 | 1277.8 | 4 | 366.1 | 1 | N/A | N/A |
| PS-49 | 27.3 | 22 | 921.4 | 4 | 366.1 | 1 | N/A | N/A |
| PS-50 | 25.9 | 20 | 1252.5 | 3 | 366.1 | 1 | 840.4 | 2 |
| PS-51 | 26.9 | 25 | 1012.7 | 4 | 366.1 | 1 | 840.4 | 2 |
| PS-52 | 24 | 23 | 942.4 | 3 | 366.1 | 1 | 1114.6 | 1 |
| PS-53 | 27.5 | 30 | 1068.7 | 4 | 366.1 | 1 | N/A | N/A |

Table 5 defines the peptide sequences for SEQ ID NOS: 23-51 from Table 1. Table 5 further identifies a corresponding protein SEQ ID NO for each peptide sequence.

TABLE 5

Peptide SEQ ID NOS

| SEQ ID NO: | Peptide Sequence | Corresponding Protein SEQ ID NO: |
|---|---|---|
| 23 | YLGNATAIFFLPDEGK | 1 |
| 24 | EGDHEFLEVPEAQEDVEATFPVHQPGNYSCSYR | 2 |
| 25 | AIGYLNTGYQR | 3 |

TABLE 5-continued

Peptide SEQ ID NOS

| SEQ ID NO: | Peptide Sequence | Corresponding Protein SEQ ID NO: |
|---|---|---|
| 26 | TEHPFTVEEFVLPK | 3 |
| 27 | VSNQTLSLFFTVLQDVPVR | 3 |
| 28 | IITILEEEMNVSVCGLYTYGKPVPGHVTVSICR | 3 |
| 29 | GCVLLSYLNETVTVSASLESVR | 3 |
| 30 | SLGNVNFTVSAEALESQELCGTEVPSVPEHGR | 3 |
| 31 | ASVSVLGDILGSAMQNTQNLLQMPYGCGEQNMVLFAPNIYVLDYLNETQQLTPEIK | 3 |
| 32 | FNLTETSEAEIHQSFQHLLR | 4 |
| 33 | DIENFNSTQK | 5 |
| 34 | QIPLCANLVPVPITNATLDQITGK | 6 |
| 35 | QDQCIYNTTYLNVQR | 7 |
| 36 | FSEFWDLDPEVRPTSAVAA | 8 |
| 37 | TELESSSCPGGIMLNETGQGYQR | 9 |
| 38 | NGTAVCATNR | 10 |
| 39 | LANLTQGEDQYYLR | 11 |
| 40 | GLNVTLSSTGR | 12 |
| 41 | VLNFTTK | 13 |
| 42 | GGSSGWSGGLAQNR | 14 |
| 43 | NLFLNHSENATAK | 15 |
| 44 | VVLHPNYSQVDIGLIK | 15 |
| 45 | TPLTANITK | 16 |
| 46 | EEQYNSTYR | 17, 18 |
| 47 | GLTFQQNASSMCVPDQDTAIR | 19 |
| 48 | LQAPLNYTEFQKPICLPSK | 20 |
| 49 | CGLVPVLAENYNK | 21 |
| 50 | NGSLFAFR | 22 |
| 51 | DIVEYYNDSNGSHVLQGR | 23 |

Table 6 identifies the proteins of SEQ ID NOS: 1-22 from Table 1. Table 6 identifies a corresponding protein abbreviation and protein name for each of protein SEQ ID NOS: 1-22. Further, Table 6 identifies a corresponding Uniprot ID for each of protein SEQ ID NOS: 1-22.

TABLE 6

Protein SEQ ID NOS

| SEQ ID NO. | Protein Abbreviation | Protein Name | Uniprot ID |
|---|---|---|---|
| 1 | A1AT | Alpha-1 Antitrypsin | P01009 |
| 2 | A1BG | Alpha-1-B Glycoprotein | P04217 |
| 3 | A2MG | Alpha-2-Macroglobulin | P01023 |
| 4 | AACT | Alpha 1-Antichymotrypsin | P01011 |
| 5 | AFAM | Afamin | P43652 |
| 6 | AGP1 | Alpha-1-acid glycoprotein 1 | P02763 |
| 7 | APOC3 | Apolipoprotein C-III | P02656 |
| 8 | APOM | Apolipoprotein M | O95445 |
| 9 | CFAI | Complement Factor I | P05156 |
| 10 | CLUS | Clusterin | P10909 |
| 11 | CO4A | Complement C4-alpha | P0C0L4 |
| 12 | CO6 | Complement component C6 | P13671 |
| 13 | CO8A | Complement C8-alpha | P07357 |
| 14 | HPT | Haptoglobin | P00738 |
| 15 | IGA2 | Immunoglobulin alpha-2 | P01877 |

TABLE 6-continued

Protein SEQ ID NOS

| SEQ ID NO. | Protein Abbreviation | Protein Name | Uniprot ID |
|---|---|---|---|
| 16 | IGG1 | Immunoglobulin gamma-1 | P01857 |
| 17 | IGG2 | Immunoglobulin gamma-2 | P01859 |
| 18 | IGM | Immunoglobulin M | P01871 |
| 19 | KLKB1 | Prekallikrein | P03952 |
| 20 | TRFE | Transferrin | P02787 |
| 21 | VTNC | Vitronectin | P04004 |
| 22 | ZA2G | Zinc-alpha-2-glycoprotein | P25311 |

Aspects of the disclosure include kits comprising one or more compositions, each comprising one or more peptide structures of the disclosure that can be used as assay standards, and instructions for use. Kits in accordance with one or more embodiments described herein may include a label indicating the intended use of the contents of the kit. The term "label" as used herein with respect to a kit includes any writing, or recorded material supplied on or with a kit, or that otherwise accompanies a kit.

The peptide structures and the transitions produced therefrom, as described herein, may be useful for diagnosing and treating various disease states within FLD, including, without limitation, NASH and HCC. A transition includes a precursor ion and at least one product ion grouping. As reviewed herein, the peptide structures in Table 1, as well as their corresponding precursor ion and product ion groupings (these ions having defined m/z ratios or m/z ratios that fall within the m/z ranges identified herein), can be used in mass spectrometry-based analyses to diagnose and facilitate treatment of diseases, such as, for examples, NASH and HCC.

Aspects of the disclosure include methods for analyzing one or more peptide structures, as described herein. In some embodiments, the methods involve processing a sample from a patient to generate a prepared sample that can be inputted into a mass spectrometry system (e.g., a reaction monitoring mass spectrometry system) using, for example, a liquid chromatography system (e.g., a high-performance liquid chromatography system (HPLC)). In certain embodiments, processing the sample can comprise performing one or more of: a denaturation procedure, a reduction procedure, an alkylation procedure, and a digestion procedure. The denaturation and reduction procedures may be implemented in a manner similar to, for example, denaturation and reduction 202 in FIG. 2. The alkylation procedure may be implemented in a manner similar to, for example, alkylation procedure 204 in FIG. 2. The digestion procedure may be implemented in a manner similar to, for example, digestion procedure 206 in FIG. 2.

In some embodiments, the methods for analyzing one or more peptide structures involve detecting a set of product ions generated by a reaction monitoring mass spectrometry system in which one or more product ions may correspond to each of the one or more peptide structures that have been inputted into the mass spectrometry system. As described herein, each peptide structure can be converted into a set of product ions having a defined m/z ratio, as provided in Table 4 or an m/z ratio within an identified m/z ratio as provided in Table 4. In some embodiments, the methods involve generating quantification (e.g., abundance) data for the one or more product ions detected using the reaction monitoring mass spectrometry system.

In some embodiments, the methods further comprise generating a diagnosis output using the quantification data and a model that has been trained using supervised or unsupervised machine learning. In certain embodiments, the reaction monitoring mass spectrometry system may include multiple/selected reaction monitoring mass spectrometry (MRM/SRM-MS) to detect the one or more product ions and generate the quantification data.

IX. Representative Experimental Results

IX.A. Sample Preparation and Mass Spectrometry Data Production

FIG. 11 is a table of the sample population used for the experiments in accordance with one or more embodiments. The samples used to generate the experimental results included serum samples from 23 patients with a biopsy-proven diagnosis of NASH (10 male, 13 female; Indivumed AG, Hamburg, Germany), 20 patients with a diagnosis of HCC (16 male, 4 female; 6 stage I, 8 stage II, 6 stage III, 2 stage IV; Indivumed AG), and from 56 healthy subjects with no history of liver disease (controls, 26 male, 30 female) which were sourced from iSpecimen, Palleon Pharmaceuticals Inc. and Human Immune Monitoring Center (HIMC) of Stanford. Clinical diagnoses of patients with NASH and HCC were based on histopathological characterization of hepatic tissue obtained either via needle biopsy or at surgery.

FIG. 12 is a table of the sample population used for validation in accordance with one or more embodiments. The validation sample population consisted of serum samples from 28 control subjects diagnosed with a benign hepatic mass (16 male, 12 female) and 28 subjects (20 male, 8 female) diagnosed with HCC, all obtained from Indivumed AG. Clinical diagnoses of patients were based on histopathological characterization of hepatic tissue obtained either via needle biopsy or at surgery.

Prior to analysis, serum samples were reduced with DTT and alkylated with IAA followed by digestion with trypsin in a water bath at 37° C. for 18 hours. To quench the digestion, formic acid was added to each sample after incubation to a final concentration of 1%.

Digested serum samples were injected into a triple quadrupole mass spectrometer (MS). Separation of the peptide structures (glycosylated and aglycosylated) was performed using a 70-min binary gradient. The triple quadrupole MS was operated in dynamic multiple reaction monitoring (dMRM) mode. Samples were injected in a randomized fashion with regard to underlying phenotype, and reference pooled serum digests were injected interspersed with study samples, at every $10^{th}$ sample position throughout the run.

An MRM analysis was performed on the peptide structures, representing a total of 73 high-abundance serum glycoproteins. A transition list consisted of glycopeptide structures as well as of aglycosylated peptide structures from each glycoprotein. The python library Scikit-learn (https://scikit-learn.org/stable/) was used for statistical analyses and for building machine learning models.

Normalized abundance data was generated for the peptide structures using the following formula:

Normalized abundance=(raw abundance of a peptide structure in sample/raw abundance of the corresponding aglycosylated peptide from the same glycoprotein)/average relative abundance of the same glycopeptides or peptides in the flanking pooled reference serum samples Relative abundance was calculated as the ratio of the raw abundance of any given glycopeptide to the sum of raw abundances of all glycopeptides.

Figure 13:
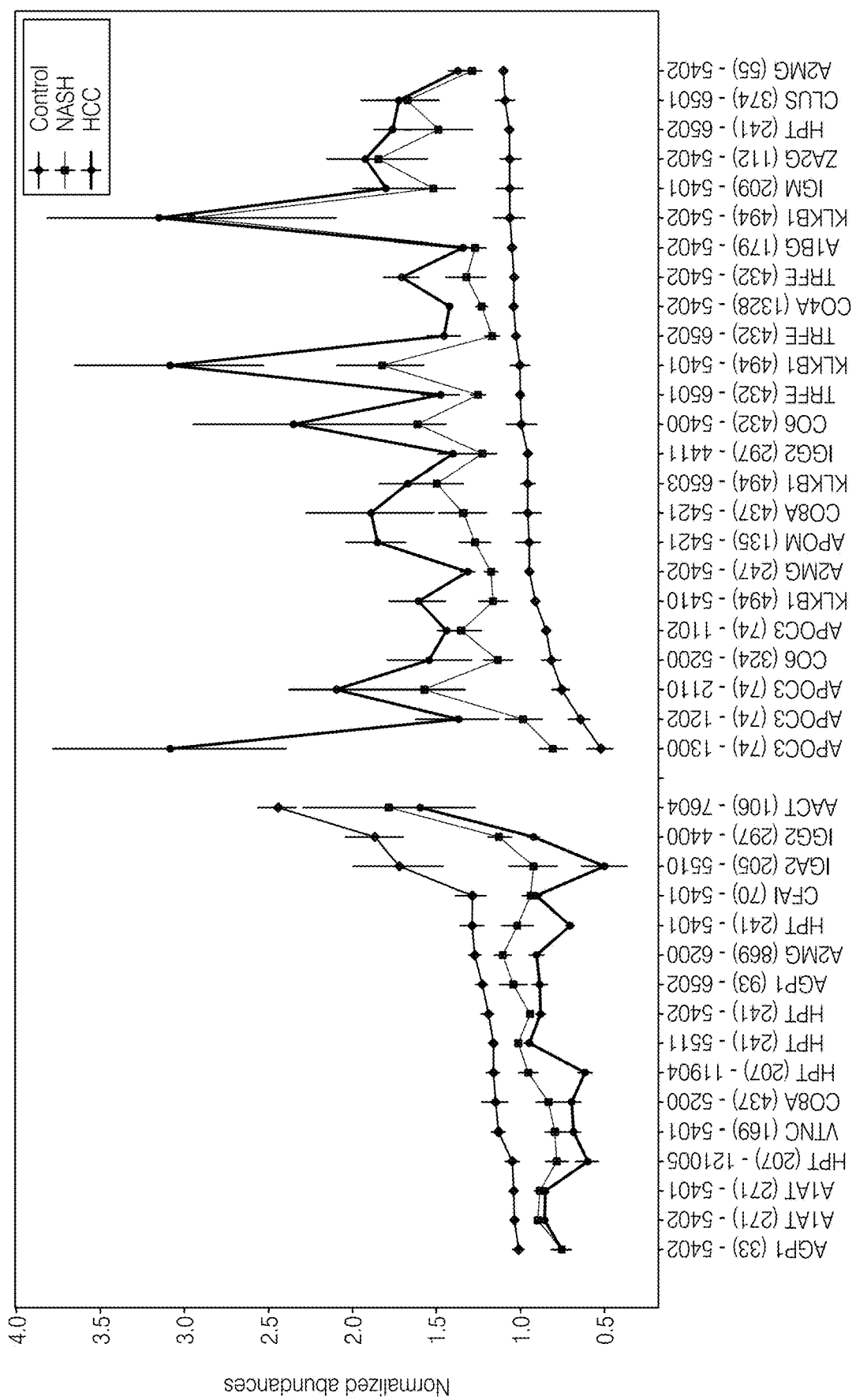
FIG. 13 is an illustration of a plot of the mean normalized abundance for selected peptide structures identified and quantified via mass spectrometry depicted in accordance with one or more embodiments.

IX.B. Analysis of Peptide Structure Data (e.g., Abundance Data) and Confirming their Diagnostic Power FIG. 13 is an illustration of a plot of the mean normalized abundance for selected peptide structures identified and quantified via mass spectrometry depicted in accordance with one or more embodiments. As depicted, changes in the mean normalized abundances for the peptide structures increased or decreased in a single direction for the progression from the control state to the NASH state to the HCC state. This abundance data shows that such peptide structures can be used to distinguish between the control state, the NASH state, and the HCC state.

Figure 14:
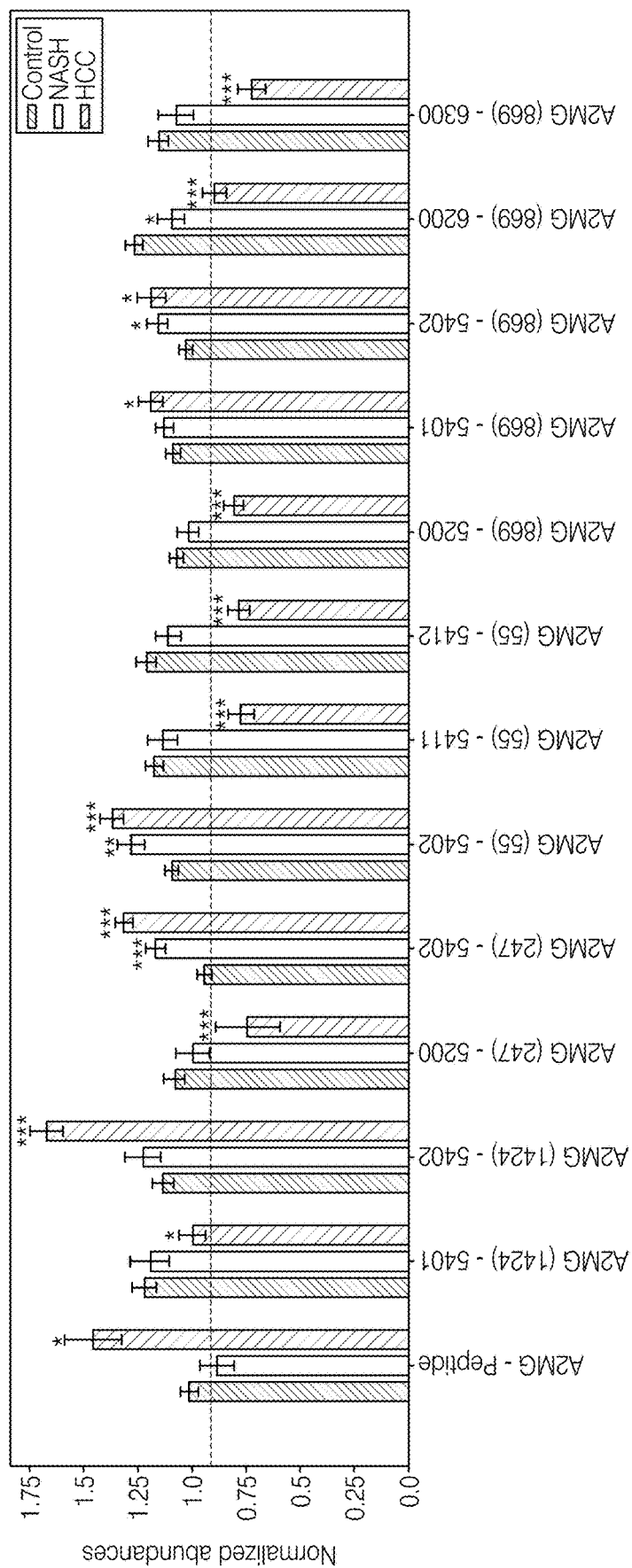
FIG. 14 is an illustration of a plot of the normalized abundances for selected peptide structures of A2MG in accordance with one or more embodiments.

FIG. 14 is an illustration of a plot of the normalized abundances for selected peptide structures of A2MG in accordance with one or more embodiments.

Figure 15:
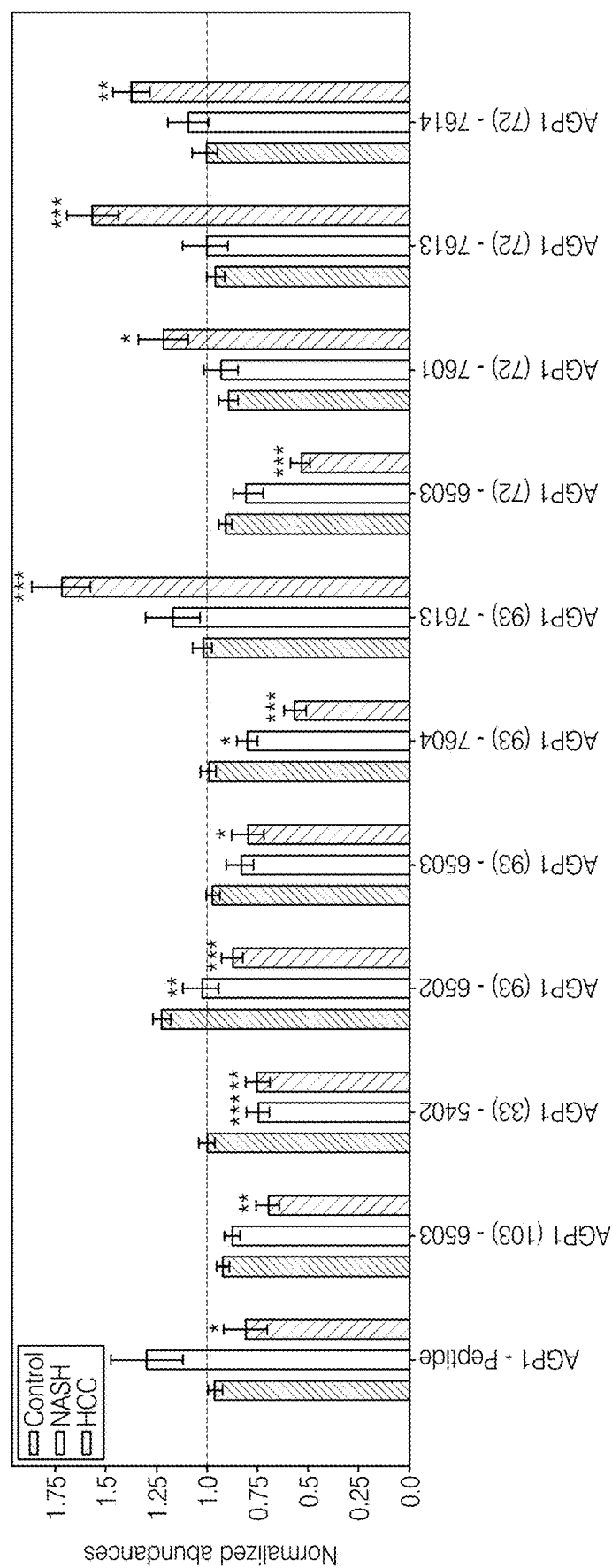
FIG. 15 is an illustration of a plot of the normalized abundances for selected peptide structures of AGP1 in accordance with one or more embodiments.

FIG. 15 is an illustration of a plot of the normalized abundances for selected peptide structures of AGP1 in accordance with one or more embodiments.

Figure 16:
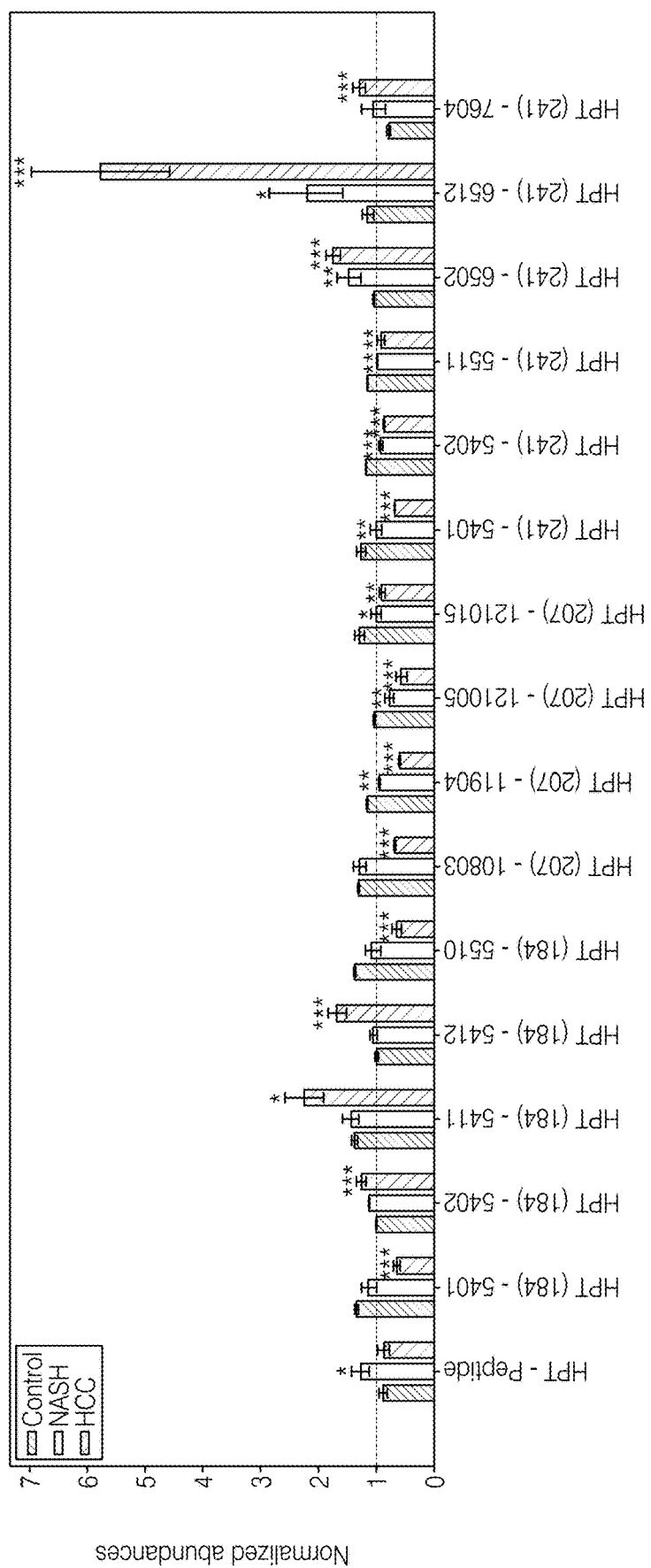
FIG. 16 is an illustration of a plot of the normalized abundances for selected peptide structures of HPT in accordance with one or more embodiments.

FIG. 16 is an illustration of a plot of the normalized abundances for selected peptide structures of HPT in accordance with one or more embodiments.

Figure 17:
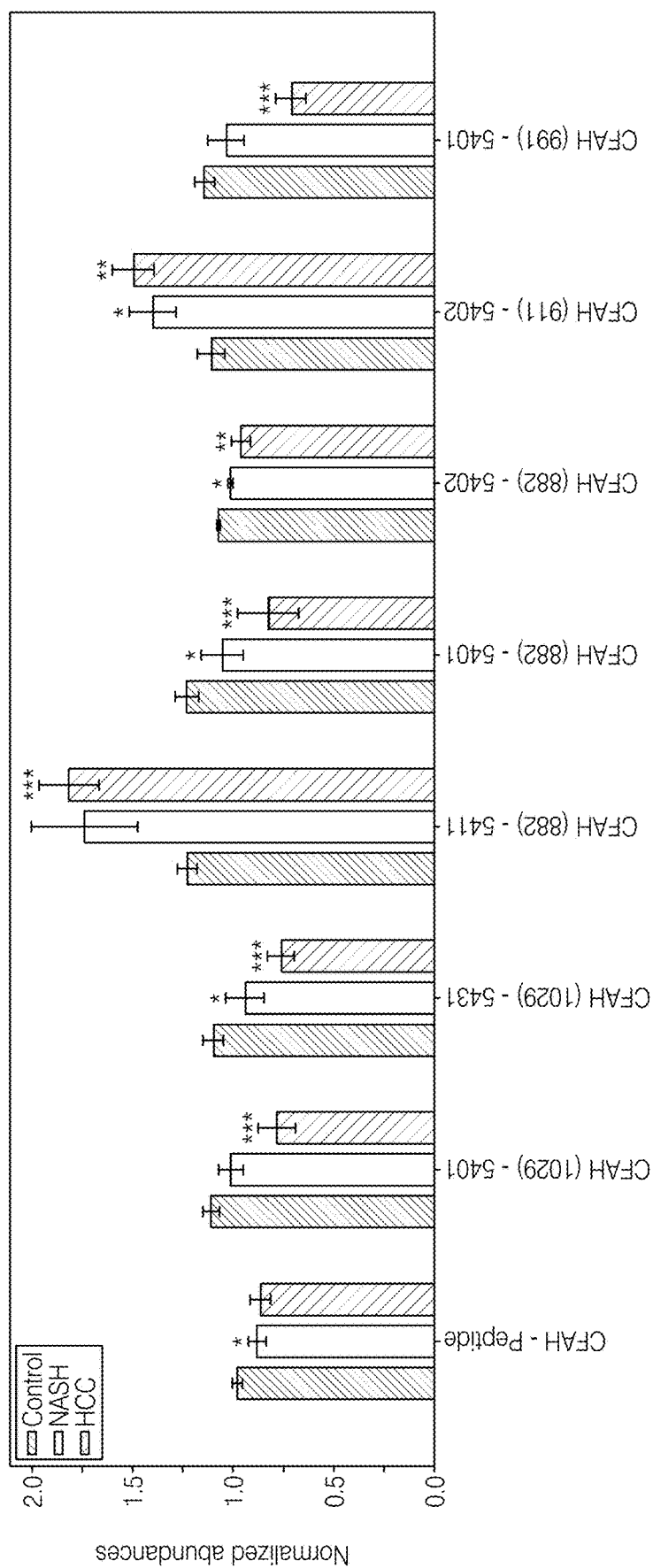
FIG. 17 is an illustration of a plot of the normalized abundances for selected peptide structures of CFAH in accordance with one or more embodiments.

FIG. 17 is an illustration of a plot of the normalized abundances for selected peptide structures of CFAH in accordance with one or more embodiments.

Figure 18:
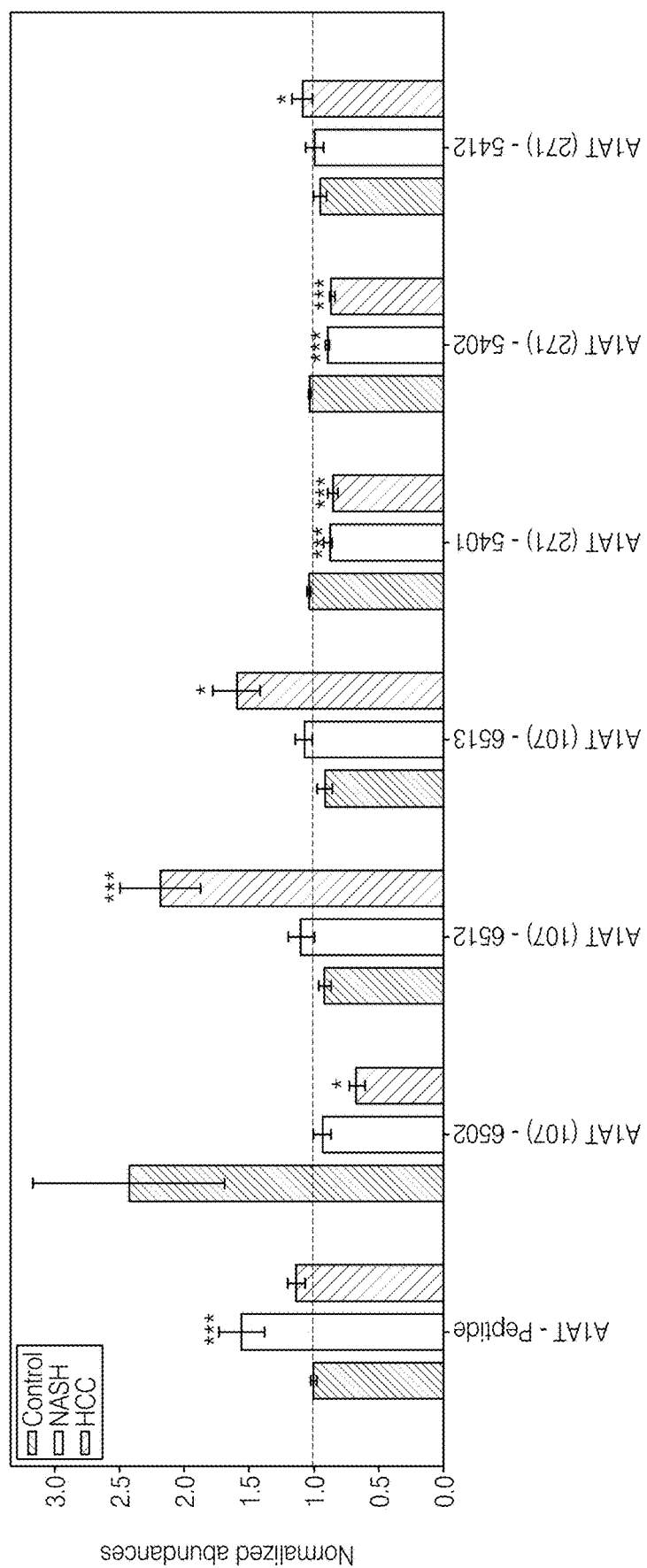
FIG. 18 is an illustration of a plot of the normalized abundances for selected peptide structures of A1AT in accordance with one or more embodiments.

FIG. 18 is an illustration of a plot of the normalized abundances for selected peptide structures of A1AT in accordance with one or more embodiments.

FIGS. 14-18 illustrate that peptide structures for a single glycoprotein (e.g., A2MG, AGP1, HPT, CFAH, A1AT) as well as peptide structures for a combination of such glycoproteins may be useful in diagnosing when a subject has progressed from a non-NASH/HCC (e.g., healthy state) to NASH or from NASH to HCC.

The normalized abundances of various peptide structures (e.g., those peptide structures identified in Table 2) were used to train a first regression model (e.g., Model 1) to generate a disease indicator for a subject. The disease indicator was generated as a score (e.g., probability score) in which the range in which the score falls enables diagnosis or classification as a non-NASH/HCC state (e.g., a control state), a NASH state, or an HCC state.

IX.C. Validation

Figure 19:
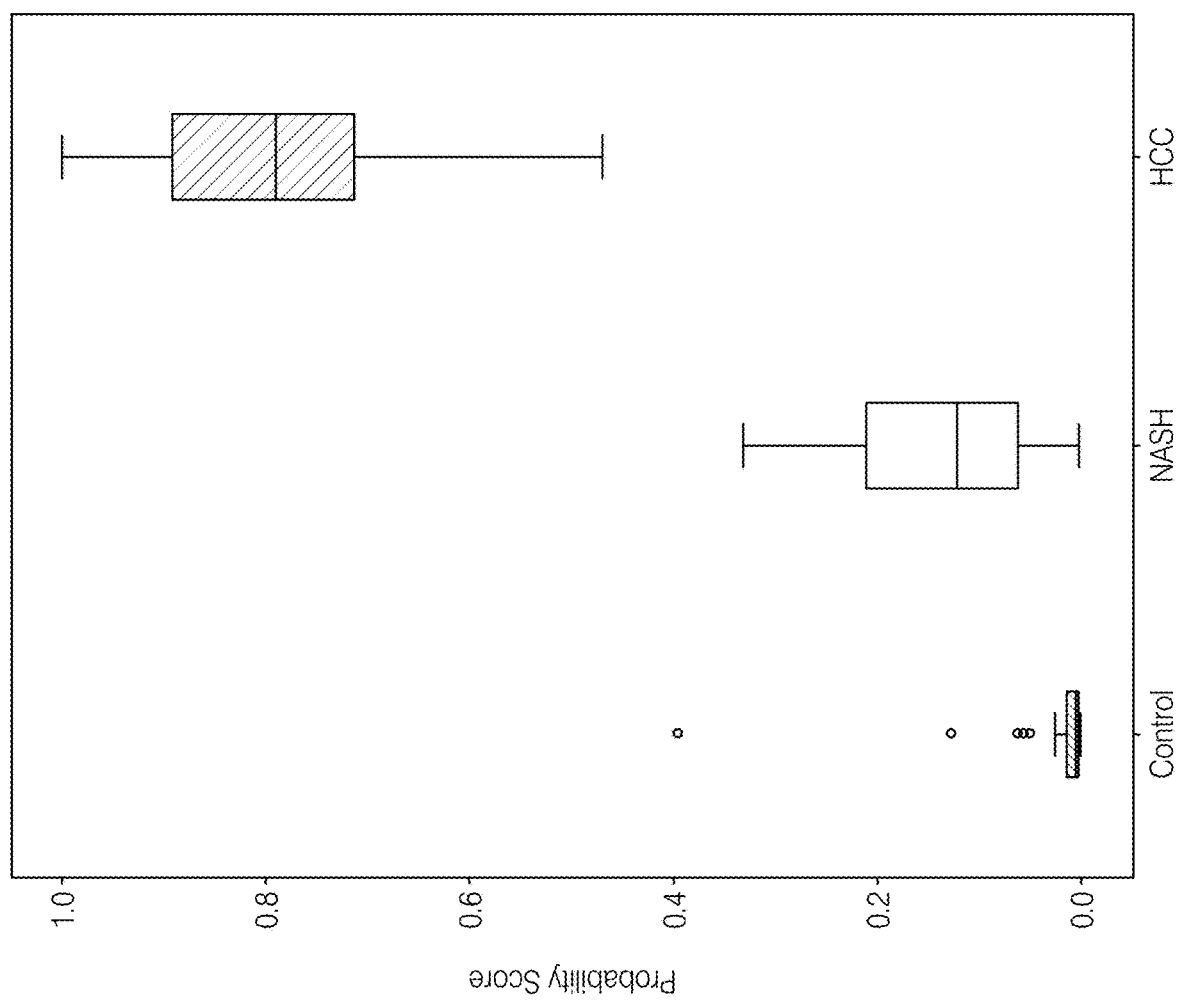
FIG. 19 is a plot diagram illustrating validation of the disease indicator's ability to distinguish between the control state, the NASH state, and the HCC state in accordance with one or more embodiments.

FIG. 19 is a plot diagram illustrating validation of the disease indicator's ability to distinguish between the control state, the NASH state, and the HCC state in accordance with one or more embodiments. As depicted, a disease indicator of about 0.0 to about 0.05 was generally accurate in classifying as a control state; a disease indicator of about 0.05 to about 0.4 was generally accurate in classifying as a NASH state; and a disease indicator of about 0.5 to about 1.00 was generally accurate in classifying as an HCC state.

IX.C.1. Validation Using the Second Sample Population

To validate the ability of peptide structures in distinguishing between HCC and other states, a second sample population (see FIG. 12) was analyzed using a second regression model (Model 2). Model 2 was trained using a smaller set of peptide structures to distinguish between HCC and benign hepatic mass. For example, the subjects used as controls were individuals with a diagnosis of a benign hepatic mass. This enabled directly assessing the discriminant power of differential peptide structure abundance for HCC.

Analysis was conducted for 10 peptide structures (8 glycopeptide structures and 2 peptide structures). The 10 peptide structures were all associated with A2MG. Model 2 was built using least absolute shrinkage and selection operator (LASSO) regularization and leave-one-out-cross-validation (LOOCV).

Figure 20:
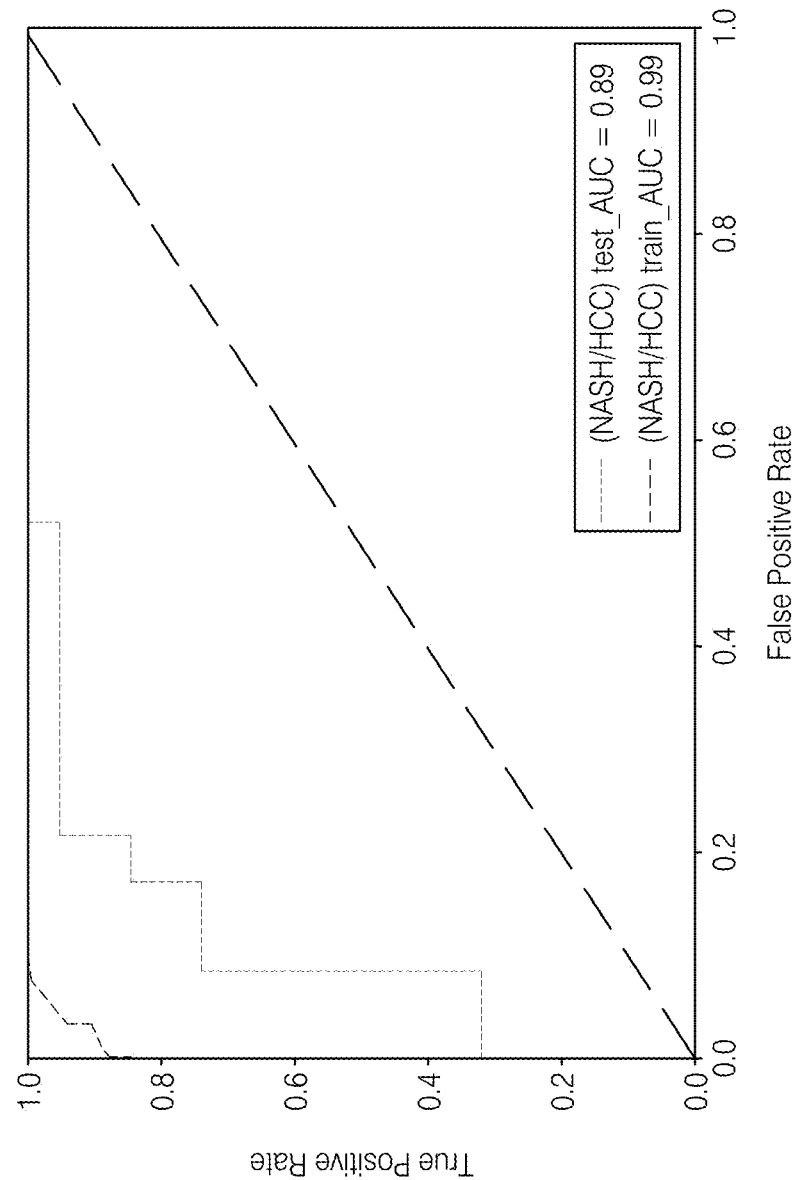
FIG. 20 is a plot of normalized abundances for these 10 peptide structures with respect to a control (e.g., healthy) state versus HCC and benign hepatic mass versus HCC in accordance with one or more embodiments.

FIG. 20 is a plot of normalized abundances for these 10 peptide structures with respect to a control (e.g., healthy) state versus HCC and benign hepatic mass versus HCC in accordance with one or more embodiments.

Figure 21:
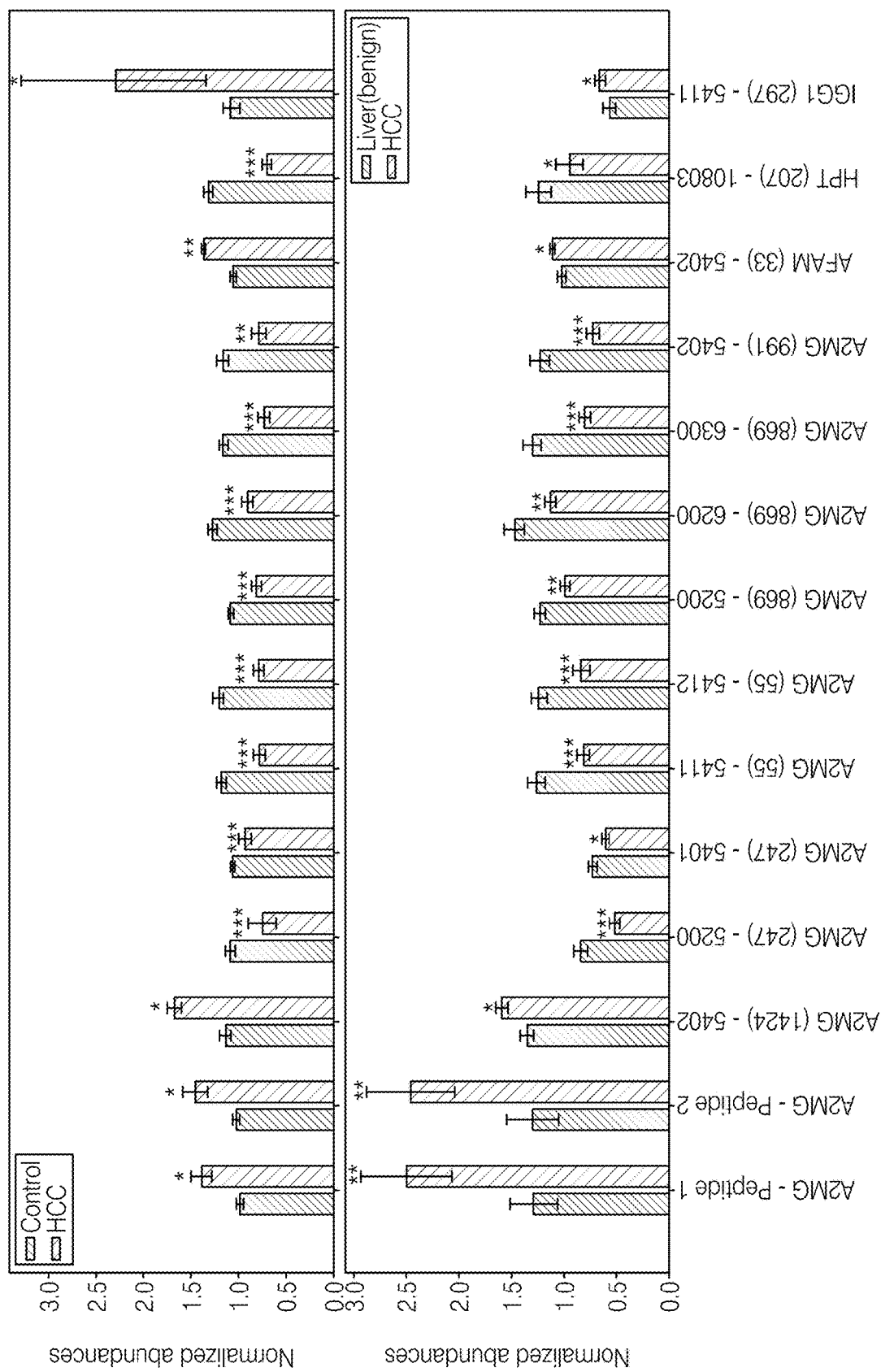
FIG. 21 is a plot of the receiver-operating-characteristic (ROC) curve for both the training and testing sets in accordance with one or more embodiments.
Figure 22:
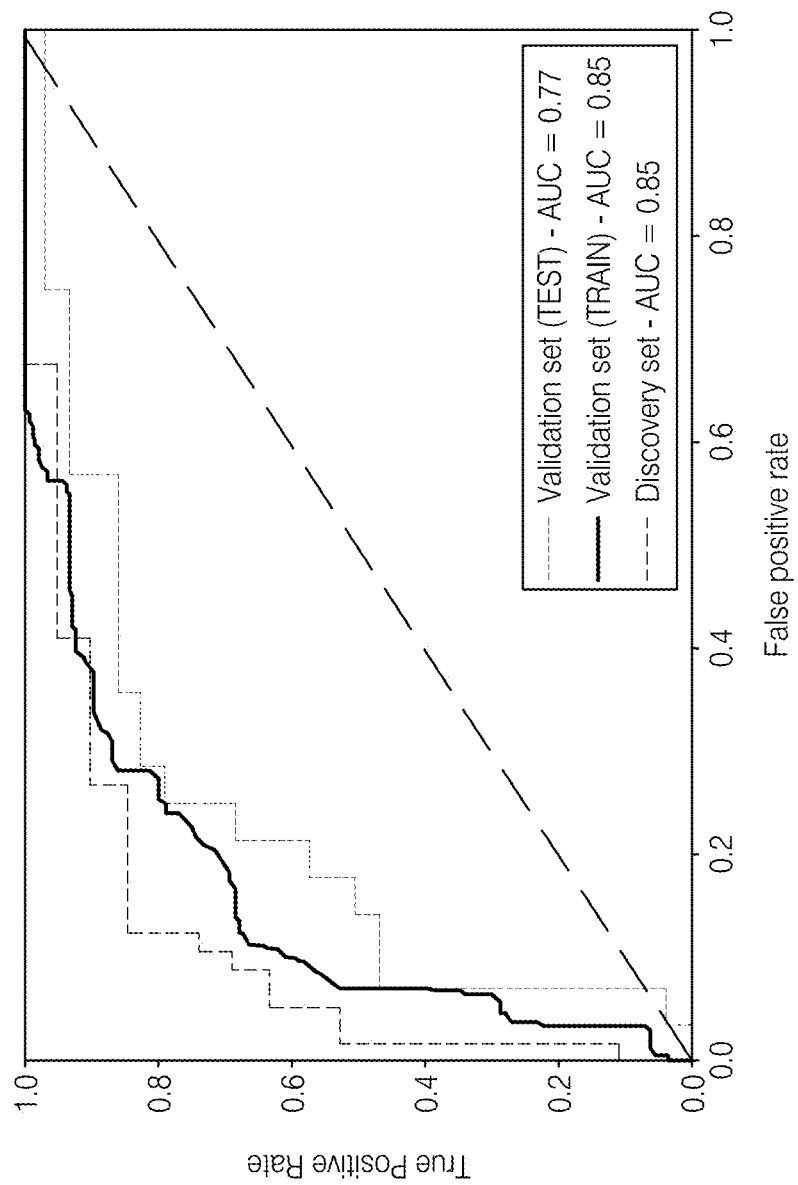
FIG. 22 is a plot of the receiver-operating-characteristic (ROC) curve for distinguishing between HCC and benign hepatic mass for both the training and testing sets in accordance with one or more embodiments.
Figure 24:
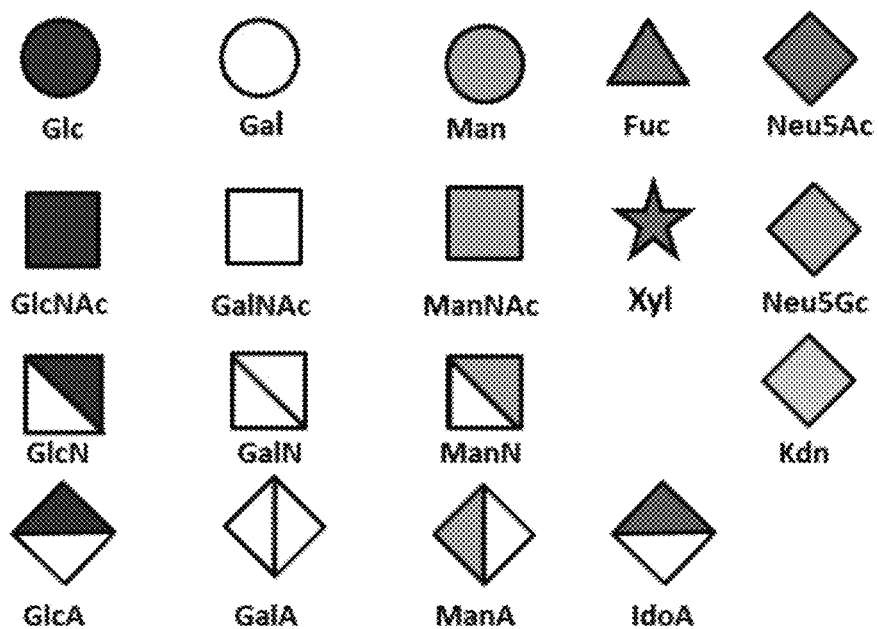
FIG. 24 is a legend for FIGS. 23A-F, identifying the components that correspond to the different graphical representations used in FIGS. 23A-F.

FIG. 21 is a plot of the receiver-operating-characteristic (ROC) curve for both the training and testing sets in accordance with one or more embodiments. The area under the ROC curve (AUROC) for the training set was found to be 0.85, and 0.77 for the testing set. The AUROC for the discovery set (e.g., the same set used for Model 1) was found to be 0.85.

Table 7 provides the weighted coefficients of the trained Model 2 and the AUC for each of the 10 peptide structures.

TABLE 7

Model 2 Analysis for AM2G-Derived Peptide Structures

| PS-ID NO. | Peptide Structure Name | Model 2 Coefficients (HCC v. Benign Hepatic Mass) | Area Under Curve (AUC) |
|---|---|---|---|
| PS-14 | A2MG (869) - 6300 | −0.569 | 0.823 |
| PS-6 | A2MG (247) - 5200 | −0.421 | 0.827 |
| PS-15 | A2MG (991) - 5402 | −0.261 | 0.806 |
| PS-10 | A2MG (55) - 5411 | 0.000 | 0.816 |
| PS-11 | A2MG (55) - 5412 | 0.000 | 0.825 |
| PS-13 | A2MG (869) - 6200 | 0.000 | 0.733 |
| PS-4 | A2MG - TEHPFTVEEFVLPK | 0.000 | 0.676 |
| PS-12 | A2MG (869) - 5200 | 0.000 | 0.76 |
| PS-16 | A2MG - AIGYLNTGYQR | 0.088 | 0.668 |
| PS-5 | A2MG (1424) - 5402 | 0.167 | 0.673 |

IX.C.2. Validation Using 3 Representative Patients

Three representative patients were tested using a trained regression model trained to distinguish between HCC and one or more other states. Table 8 provides the normalized abundances determined for each patient for various peptide structures. At the bottom of Table 9, the disease indicators computed for these patients. The disease indicator is a probability score that indicates the likelihood that the subject has HCC. The disease indicator was used to classify only patient 3 as having HCC, which was a correct diagnosis.

TABLE 8

Patient Examples

| Peptide Structure Name | Normalized abundance (patient 1) | Normalized abundance (patient 2) | Normalized abundance (patient 3) |
|---|---|---|---|
| TRFE (432) - 6502 | 1.28 | 1.12 | 1.20 |
| KLKB1 (494) - 5410 | 0.60 | 1.02 | 1.49 |
| KLKB1 (494) - 5402 | 0.51 | 1.41 | 3.91 |
| ZA2G (112) - 5402 | 0.45 | 1.07 | 1.39 |
| APOC3 (74) - 2110 | 2.19 | 1.71 | 2.02 |

TABLE 8-continued

Patient Examples

| Peptide Structure Name | Normalized abundance (patient 1) | Normalized abundance (patient 2) | Normalized abundance (patient 3) |
|---|---|---|---|
| A2MG (55) - 5402 | 1.22 | 1.47 | 1.69 |
| A2MG (247) - 5402 | 0.82 | 1.38 | 1.42 |
| CO6 (324) - 5400 | 1.15 | 1.49 | 0.90 |
| TRFE (432) - 6501 | 1.18 | 1.36 | 1.03 |
| CO4A (1328) - 5402 | 1.02 | 0.98 | 1.68 |
| TRFE (432) - 5402 | 0.93 | 0.91 | 1.65 |
| APOC3 (74) - 1102 | 1.33 | 1.08 | 1.82 |
| IGM (209) - 5401 | 1.05 | 0.93 | 2.49 |
| CO8A (437) - 5410 | 3.05 | 1.28 | 6.00 |
| APOC3 (74) - 1202 | 1.42 | 0.41 | 0.65 |
| KLKB1 (494) - 6503 | 0.95 | 0.71 | 2.69 |
| APOC3 (74) - 1300 | 0.87 | 0.99 | 4.52 |
| KLKB1 (494) - 5401 | 1.03 | 1.71 | 4.30 |
| HPT (241) - 6502 | 1.34 | 1.03 | 1.58 |
| CLUS (374) - 6501 | 1.17 | 1.83 | 1.12 |
| APOM (135) - 5421 | 1.30 | 1.19 | 2.03 |
| A1BG (179) - 5402 | 1.07 | 1.07 | 1.47 |
| IGG2 (297) - 4411 | 1.21 | 0.96 | 1.24 |
| CO6 (324) - 5200 | 2.27 | 0.81 | 1.02 |
| HPT (207) - 11904 | 1.20 | 0.92 | 0.57 |
| HPT (241) - 5401 | 0.92 | 0.75 | 0.47 |
| AGP1 (93) - 6502 | 1.34 | 0.87 | 1.16 |
| HPT (241) - 5511 | 1.37 | 1.06 | 0.80 |
| CFAI (70) - 5401 | 0.86 | 1.03 | 0.53 |
| HPT (241) - 5402 | 1.49 | 0.98 | 0.83 |
| A2MG (869) - 6200 | 0.81 | 0.98 | 0.97 |
| VTNC (169) - 5401 | 1.44 | 0.89 | 0.97 |
| AACT (106) - 7604 | 2.35 | 2.77 | 0.78 |
| IGG2 (297) - 4400 | 1.16 | 0.79 | 0.78 |
| CO8A (437) - 5200 | 1.54 | 0.72 | 0.50 |
| A1AT (271) - 5402 | 1.01 | 0.98 | 0.79 |
| AGP1 (33) - 5402 | 1.11 | 0.87 | 0.59 |
| IGA2 (205) - 5510 | 3.00 | 0.41 | 0.09 |
| A1AT (271) - 5401 | 0.90 | 0.95 | 0.76 |
| HPT (207) - 121005 | 1.17 | 0.69 | 0.30 |
| Probability of HCC vs rest | 0.01 | 0.23 | 0.90 |

X. Additional Considerations

Any headers and/or subheaders between sections and subsections of this document are included solely for the purpose of improving readability and do not imply that features cannot be combined across sections and subsection. Accordingly, sections and subsections do not describe separate embodiments.

While the present teachings are described in conjunction with various embodiments, it is not intended that the present teachings be limited to such embodiments. On the contrary, the present teachings encompass various alternatives, modifications, and equivalents, as will be appreciated by those of skill in the art. The present description provides preferred exemplary embodiments, and is not intended to limit the scope, applicability or configuration of the disclosure. Rather, the present description of the preferred exemplary embodiments will provide those skilled in the art with an enabling description for implementing various embodiments.

It is understood that various changes may be made in the function and arrangement of elements without departing from the spirit and scope as set forth in the appended claims. Thus, such modifications and variations are considered to be within the scope set forth in the appended claims. Further, the terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

In describing the various embodiments, the specification may have presented a method and/or process as a particular sequence of steps. However, to the extent that the method or process does not rely on the particular order of steps set forth herein, the method or process should not be limited to the particular sequence of steps described, and one skilled in the art can readily appreciate that the sequences may be varied and still remain within the spirit and scope of the various embodiments.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

Specific details are given in the present description to provide an understanding of the embodiments. However, it is understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

SEQUENCE LISTING

```
Sequence total quantity: 54
SEQ ID NO: 1            moltype = AA  length = 418
FEATURE                 Location/Qualifiers
source                  1..418
                        mol_type = protein
                        organism = synthetic construct
CARBOHYD                271
                        note = N is linked to Hex(5)HexNAc(4)Fuc(0)NeuAc(1)
CARBOHYD                271
                        note = N is linked to Hex(5)HexNAc(4)Fuc(0)NeuAc(2)
SEQUENCE: 1
MPSSVSWGIL LLAGLCCLVP VSLAEDPQGD AAQKTDTSHH DQDHPTFNKI TPNLAEFAFS   60
```

```
LYRQLAHQSN STNIFFSPVS IATAFAMLSL GTKADTHDEI LEGLNFNLTE IPEAQIHEGF   120
QELLRTLNQP DSQLQLTTGN GLFLSEGLKL VDKFLEDVKK LYHSEAFTVN FGDTEEAKKQ   180
INDYVEKGTQ GKIVDLVKEL DRDTVFALVN YIFFKGKWER PFEVKDTEEE DFHVDQVTTV   240
KVPMMKRLGM FNIQHCKKLS SWVLLMKYLG NATAIFFLPD EGKLQHLENE LTHDIITKFL   300
ENEDRRSASL HLPKLSITGT YDLKSVLGQL GITKVFSNGA DLSGVTEEAP LKLSKAVHKA   360
VLTIDEKGTE AAGAMFLEAI PMSIPPEVKF NKPFVFLMIE QNTKSPLFMG KVVNPTQK     418

SEQ ID NO: 2            moltype = AA  length = 495
FEATURE                 Location/Qualifiers
source                  1..495
                        mol_type = protein
                        organism = synthetic construct
CARBOHYD                179
                        note = N is linked to Hex(5)HexNAc(4)Fuc(0)NeuAc(2)
SEQUENCE: 2
MSMLVVFLLL WGVTWGPVTE AAIFYETQPS LWAESESLLK PLANVTLTCQ AHLETPDFQL    60
FKNGVAQEPV HLDSPAIKHQ FLLTGDTQGR YRCRSGLSTG WTQLSKLLEL TGPKSLPAPW   120
LSMAPVSWIT PGLKTTAVCR GVLRGVTFLL RREGDHEFLE VPEAQEDVEA TFPVHQPGNY   180
SCSYRTDGEG ALSEPSATVT IEELAAPPPP VLMHHGESSQ VLHPGNKVTL TCVAPLSGVD   240
FQLRRGEKEL LVPRSSTSPD RIFFHLNAVA LGDGGHYTCR YRLHDNQNGW SGDSAPVELI   300
LSDETLPAPE FSPEPESGRA LRLRCLAPLE GARFALVRED RGGRRVHRFQ SPAGTEALFE   360
LHNISVADSA NYSCVYVDLK PPFGGSAPSE RLELHVDGPP PRPQLRATWS GAVLAGRDAV   420
LRCEGPIPDV TFELLREGET KAVKTVRTPG AAANLELIFV GPQHAGNYRC RYRSWVPHTF   480
ESELSDPVEL LVAES                                                   495

SEQ ID NO: 3            moltype = AA  length = 1474
FEATURE                 Location/Qualifiers
source                  1..1474
                        mol_type = protein
                        organism = synthetic construct
CARBOHYD                1424
                        note = N is linked to Hex(5)HexNAc(4)Fuc(0)NeuAc(2)
CARBOHYD                247
                        note = N is linked to Hex(5)HexNAc(2)Fuc(0)NeuAc(0)
CARBOHYD                247
                        note = N is linked to Hex(5)HexNAc(4)Fuc(0)NeuAc(1)
CARBOHYD                247
                        note = N is linked to Hex(5)HexNAc(4)Fuc(0)NeuAc(2)
CARBOHYD                55
                        note = N is linked to Hex(5)HexNAc(4)Fuc(0)NeuAc(2)
CARBOHYD                55
                        note = N is linked to Hex(5)HexNAc(4)Fuc(1)NeuAc(1)
CARBOHYD                55
                        note = N is linked to Hex(5)HexNAc(4)Fuc(1)NeuAc(2)
CARBOHYD                869
                        note = N is linked to Hex(5)HexNAc(2)Fuc(0)NeuAc(0)
CARBOHYD                869
                        note = N is linked to Hex(6)HexNAc(2)Fuc(0)NeuAc(0)
CARBOHYD                869
                        note = N is linked to Hex(6)HexNAc(3)Fuc(0)NeuAc(0)
CARBOHYD                991
                        note = N is linked to Hex(5)HexNAc(4)Fuc(0)NeuAc(2)
SEQUENCE: 3
MGKNKLLHPS LVLLLLVLLP TDASVSGKPQ YMVLVPSLLH TETTEKGCVL LSYLNETVTV    60
SASLESVRGN RSLFTDLEAE NDVLHCVAFA VPKSSSNEEV MFLTVQVKGP TQEFKKRTTV   120
MVKNEDSLVF VQTDKSIYKP GQTVKFRVVS MDENFHPLNE LIPLVYIQDP KGNRIAQWQS   180
FQLEGGLKQF SFPLSSEPFQ GSYKVVVQKK SGGRTEHPPT VEEFVLPKFE VQVTVPKIIT   240
ILEEEMNVSV CGLYTYGKPV PGHVTVSICR KYSDASDCHG EDSQAFCEKF SGQLNSHGCF   300
YQQVKTKVFQ LKRKEYEMKL HTEAQIQEEG TVVELTGRQS SEITRTITKL SFVKVDSHFR   360
QGIPFFGQVR LVDGKGVPIP NKVIFIRGNE ANYYSNATTD EHGLVQFSIN TTNVMGTSLT   420
VRVNYKDRSP CYGYQWVSEE HEEAHHTAYL VFSPSKSFVH LEPMSHELPC GHTQTVQAHY   480
ILNGGTLLGL KKLSFYYLIM AKGGIVRTGT HGLLVKQEDM KGHFSISIPV KSDIAPVARL   540
LIYAVLPTGD VIGDSAKYDV ENCLANKVDL SFSPSQSLPA SHAHLRVTAA PQSVCALRAV   600
DQSVLLMKPD AELSASSVYN LLPEKDLTGF PGPLNDQDNE DCINRHNVYI NGITYTPVSS   660
TNEKDMYSFL EDMGLKAFTN SKIRKPKMCP QLQQYEMHGP EGLRVGFYES DVMGRGHARL   720
VHVEEPHTET VRKYFPETWI WDLVVVNSAG VAEVGVTVPD TITEWKAGAF CLSEDAGLGI   780
SSTASLRAFQ PFFVELTMPY SVIRGEAFTL KATVLNYLPK CIRVSVQLEA SPAFLAVPVE   840
KEQAPHCICA NGRQTVSWAV TPKSLGNVNF TVSAEALESQ ELCGTEVPSV PEHGRKDTVI   900
KPLLVEPEGL EKETTFNSLL CPSGGEVSEE LSLKLPPNVV EESARASVSV LGDILGSAMQ   960
NTQNLLQMPY GCGEQNMVLF APNIYVLDYL NETQQLTPEI KSKAIGYLNT GYQRQLNYKH  1020
YDGSYSTFGE RYGRNQGNTW LTAFVLKTFA QARAYIFIDE AHITQALIWL SQRQKDNGCF  1080
RSSGSLLNNA IKGGVEDEVT LSAYITIALL EIPLTVTHPV VRNALFCLES AWKTAQEGDH  1140
GSHVYTKALL AYAFALAGNQ DKRKEVLKSL NEEAVKKDNS HWERPQKPK APVGHFYEPQ   1200
APSAEVEMTS YVLLAYLTAQ PAPTSEDLTS ATNIVKWITK QQNAQGGFSS TQDTVVALHA  1260
LSKYGAATFT RTGKAAQVTI QSSGTFSSKF QVDNNRLLLL QQVSLPELPG EYSMKVTGEG  1320
CVYLQTSLKY NILPEKEEFP FALGVQTLPQ TCDEPKAHTS FQISLSVSYT GSRSASNMAI  1380
VDVKMVSGFI PLKPTVKMLE RSNHVSRTEV SSNHVLIYLD KVSNQTLSLF FTVLQDPVPR  1440
DLKPAIVKVY DYYETDEFAI AEYNAPCSKD LGNA                              1474
```

```
SEQ ID NO: 4              moltype = AA  length = 423
FEATURE                   Location/Qualifiers
source                    1..423
                          mol_type = protein
                          organism = synthetic construct
CARBOHYD                  106
                          note = N is linked to Hex(7)HexNAc(6)Fuc(0)NeuAc(4)
SEQUENCE: 4
MERMLPLLAL GLLAAGFCPA VLCHPNSPLD EENLTQENQD RGTHVDLGLA SANVDFAFSL   60
YKQLVLKAPD KNVIFSPLSI STALAFLSLG AHNTTLTEIL KGLKFNLTET SEAEIHQSFQ  120
HLLRTLNQSS DELQLSMGNA MFVKEQLSLL DRFTEDAKRL YGSEAFATDF QDSAAAKKLI  180
NDYVKNGTRG KITDLIKDLD SQTMMVLVNY IFFKAKWEMP FDPQDTHQSR FYLSKKKWVM  240
VPMMSLHHLT IPYFRDEELS CTVVELKYTG NASALFILPD QDKMEEVEAM LLPETLKRWR  300
DSLEFREIGE LYLPKFSISR DYNLNDILLQ LGIEEAFTSK ADLSGITGAR NLAVSQVVHK  360
AVLDVFEEGT EASAATAVKI TLLSALVETR TIVRFNRPFL MIIVPTDTQN IFFMSKVTNP  420
KQA                                                                423

SEQ ID NO: 5              moltype = AA  length = 599
FEATURE                   Location/Qualifiers
source                    1..599
                          mol_type = protein
                          organism = synthetic construct
CARBOHYD                  33
                          note = N is linked to Hex(5)HexNAc(4)Fuc(0)NeuAc(2)
SEQUENCE: 5
MKLLLKLTGFI FFLFFLTESL TLPTQPRDIE NFNSTQKFIE DNIEYITIIA FAQYVQEATF   60
EEMEKLVKDM VEYKDRCMAD KTLPECSKLP NNVLQEKICA MEGLPQKHNF SHCCSKVDAQ  120
RRLCFFYNKK SDVGFLPPFP TLDPEEKCQA YESNRESLLN HFLYEVARRN PFVFAPTLLT  180
VAVHFEEVAK SCCEEQNKVN CLQTRAIPVT QYLKAFSSYQ KHVCGALLKF GTKVVHFIYI  240
AILSQKFPKI EFKELISLVE DVSSNYDGCC EGDVVQCIRD TSKVMNHICS KQDSISSKIK  300
ECCEKKIPER GQCIINSNKD DRPKDLSLRE GKFTDSENVC QERDADPDTF FAKFTFEYSR  360
RHPDLSIPEL LRIVQIYKDL LRNCCNTENP PGCYRYAEDK FNETTEKSLK MVQQECKHFQ  420
NLGKDGLKYH YLIRLTKIAP QLSTEELVSL GEKMVTAFTT CCTLSEEFAC VDNLADLVFG  480
ELCGVNENRT INPAVDHCCK TNFAFRRPCF ESLKADKTYV PPPFSQDLFT PHADMCQSQN  540
EELQRKTDRF LVNLVKLKHE LTDEELQSLF TNFANVVDKC CKAESPEVCF NEESPKIGN   599

SEQ ID NO: 6              moltype = AA  length = 201
FEATURE                   Location/Qualifiers
source                    1..201
                          mol_type = protein
                          organism = synthetic construct
CARBOHYD                  33
                          note = N is linked to Hex(5)HexNAc(4)Fuc(0)NeuAc(2)
CARBOHYD                  93
                          note = N is linked to Hex(6)HexNAc(5)Fuc(0)NeuAc(2)
SEQUENCE: 6
MALSWVLTVL SLLPLLEAQI PLCANLVPVP ITNATLDQIT GKWFYIASAF RNEEYNKSVQ   60
EIQATFFYFT PNKTEDTIFL REYQTRQDQC IYNTTYLNVQ RENGTISRYV GGQEHFAHLL  120
ILRDTKTYML AFDVNDEKNW GLSVYADKPE TTKEQLGEFY EALDCLRIPK SDVVYTDWKK  180
DKCEPLEKQH EKERKQEEGE S                                            201

SEQ ID NO: 7              moltype = AA  length = 99
FEATURE                   Location/Qualifiers
source                    1..99
                          mol_type = protein
                          organism = synthetic construct
CARBOHYD                  94
                          note = T is linked to Hex(1)HexNAc(1)Fuc(0)NeuAc(2)
CARBOHYD                  94
                          note = T is linked to Hex(1)HexNAc(2)Fuc(0)NeuAc(2)
CARBOHYD                  94
                          note = T is linked to Hex(1)HexNAc(3)Fuc(0)NeuAc(0)
CARBOHYD                  94
                          note = T is linked to Hex(2)HexNAc(1)Fuc(1)NeuAc(0)
SEQUENCE: 7
MQPRVLLVVA LLALLASARA SEAEDASLLS FMQGYMKHAT KTAKDALSSV QESQVAQQAR   60
GWVTDGFSSL KDYWSTVKDK FSEFWDLDPE VRPTSAVAA                          99

SEQ ID NO: 8              moltype = AA  length = 188
FEATURE                   Location/Qualifiers
source                    1..188
                          mol_type = protein
                          organism = synthetic construct
CARBOHYD                  135
                          note = N is linked to Hex(5)HexNAc(4)Fuc(2)NeuAc(1)
SEQUENCE: 8
MFHQIWAALL YFYGIILNSI YQCPEHSQLT TLGVDGKEFP EVHLGQWYFI AGAAPTKEEL   60
ATFDPVDNIV FNMAAGSAPM QLHLRATIRM KDGLCVPRKW IYHLTEGSTD LRTEGRPDMK  120
TELFSSSCPG GIMLNETGQG YQRFLLYNRS PHPPEKCVEE FKSLTSCLDS KAFLLTPRNQ  180
```

```
EACELSNN                                                                              188

SEQ ID NO: 9            moltype = AA  length = 583
FEATURE                 Location/Qualifiers
source                  1..583
                        mol_type = protein
                        organism = synthetic construct
CARBOHYD                70
                        note = N is linked to Hex(5)HexNAc(4)Fuc(0)NeuAc(1)
SEQUENCE: 9
MKLLHVFLLF LCFHLRFCKV TYTSQEDLVE KKCLAKKYTH LSCDKVFCQP WQRCIEGTCV    60
CKLPYQCPKN GTAVCATNRR SFPTYCQQKS LECLHPGTKF LNNGTCTAEG KFSVSLKHGN   120
TDSEGIVEVK LVDQDKTMFI CKSSWSMREA NVACLDLGFQ QGADTQRRFK LSDLSINSTE   180
CLHVHCRGLE TSLAECTFTK RRTMGYQDFA DVVCYTQKAD SPMDDFFQCV NGKYISQMKA   240
CDGINDCGDQ SDELCCKACQ GKGFHCKSGV CIPSQYQCNG EVDCITGEDE VGCAGFASVT   300
QEETEILTAD MDAERRRIKS LLPKLSCGVK NRMHIRRKRI VGGKRAQLGD LPWQVAIKDA   360
SGITCGGIYI GGCWILTAAH CLRASKTHRY QIWTTVVDWI HPDLKRIVIE YVDRIIFHEN   420
YNAGTYQNDI ALIEMKKDGN KKDCELPRSI PACVPWSPYL FQPNDTCIVS GWGREKDNER   480
VFSLQWGEVK LISNCSKFYG NRFYEKEMEC AGTYDGSIDA CKGDSGGPLV CMDANNVTYV   540
WGVVSWGENC GKPEFPGVYT KVANYFDWIS YHVGRPFISQ YNV                    583

SEQ ID NO: 10           moltype = AA  length = 449
FEATURE                 Location/Qualifiers
source                  1..449
                        mol_type = protein
                        organism = synthetic construct
CARBOHYD                374
                        note = N is linked to Hex(6)HexNAc(5)Fuc(0)NeuAc(1)
SEQUENCE: 10
MMKTLLLFVG LLLTWESGQV LGDQTVSDNE LQEMSNQGSK YVNKEIQNAV NGVKQIKTLI    60
EKTNEERKTL LSNLEEAKKK KEDALNETRE SETKLKELPG VCNETMMALW EECKPCLKQT   120
CMKFYARVCR SGSGLVGRQL EEFLNQSSPF YFWMNGDRID SLLENDRQQT HMLDVMQDHF   180
SRASSIIDEL FQDRFFTREP QDTYHYLPFS LPHRRPHFFF PKSRIVRSLM PFSPYEPLNF   240
HAMFQPFLEM IHEAQQAMDI HFHSPAFQHP PTEFIREGDD DRTVCREIRH NSTGCLRMKD   300
QCDKCREILS VDCSTNNPSQ AKLRRELDES LQVAERLTRK YNELLKSYQW KMLNTSSLLE   360
QLNEQFNWVS RLANLTQGED QYYLRVTTVA SHTSDSDVPS GVTEVVVKLF DSDPITVTVP   420
VEVSRKNPKF METVAEKALQ EYRKKHREE                                    449

SEQ ID NO: 11           moltype = AA  length = 1744
FEATURE                 Location/Qualifiers
source                  1..1744
                        mol_type = protein
                        organism = synthetic construct
CARBOHYD                1328
                        note = N is linked to Hex(5)HexNAc(4)Fuc(0)NeuAc(2)
SEQUENCE: 11
MRLLWGLIWA SSFFTLSLQK PRLLLFSPSV VHLGVPLSVG VQLQDVPRGQ VVKGSVFLRN    60
PSRNNVPCSP KVDFTLSSER DFALLSLQVP LKDAKSCGLH QLLRGPEVQL VAHSPWLKDS   120
LSRTTNIQGI NLLFSSRRGH LFLQTDQPIY NPGQRVRYRV FALDQKMRPS TDTITVMVEN   180
SHGLRVRKKE VYMPSSIFQD DFVIPDISEP GTWKISARFS DGLESNSSTQ FEVKKYVLPN   240
FEVKITPGKP YILTVPGHLD EMQLDIQARY IYGKPVQGVA YVRFGLLDED GKKTFFRGLE   300
SQTKLVNGQS HISLSKAEFQ DALEKLNMGI TDLQGLRLYV AAAIIESPGG EMEEAELTSW   360
YFVSSPFSLD LSKTKRHLVP GAPFLLQALV REMSGSPASG IPVKVSATVS SPGSVPEVQD   420
IQQNTDGSGQ VSIPIIIPQT ISELQLSVSA GSPHPAIARL TVAAPPSGGP GFLSIERPDS   480
RPPRVGDTLN LNLRAVGSGA TFSHYYYMIL SRGQIVFMNR EPKRTLTSVS LVFVDHHLAPS  540
FYFVAFYYHG DHPVANSLRV DVQAGACEGK LELSVDGAKQ YRNGESVKLH LETDSLALVA   600
LGALDTALYA AGSKSHKPLN MGKVFEAMNS YDLGCGPGGG DSALQVFQAA GLAFSDGDQW   660
TLSRKRLSCP KEKTTRKKRN VNFQKAINEK LGQYASPTAK RCCQDGVTRL PMMRSCEQRA   720
ARVQQPDCRE PFLSCCQFAE SLRKKSRDKG QAGLQRALEI LQEEDLIDED DIPVRSFFPE   780
NWLWRVETVD RFQILTLWLP DSLTTWEIHG LSLSKTKGLC VATPVQLRVF REFHLHLRLP   840
MSVRRFEQLE LRPVLYNYLD KNLTVSVHVS PVEGLCLAGG GGLAQQVLVP AGSARPVAFS   900
VVPTAAAAVS LKVVARGSFE FPVGDAVSKV LQIEKEGAIH REELVYELNP LDHRGRTLEI   960
PGNSDPNMIP DGDFNSYVRV TASDPLDTLG SEGALSPGGV ASLLRLPRGC GEQTMIYLAP  1020
TLAASRYLDK TEQWSTLPPE TKDHAVDLIQ KGYMRIQQFR KADGSYAAWL SRDSSTWLTA  1080
FVLKVLSLAQ EQVGGSPEKL QETSNWLLSQ QQADGSFQDP CPVLDRSMQG GLVGNDETVA  1140
LTAFVTIALH HGLAVFQDEG AEPLKQRVEA SISKANSFLG EKASAGLLGA HAAAITAYAL  1200
TLTKAPVDLL GVAHNNLMAM AQETGDNLYW GSVTGSQSNA VSPTPAPRNP SDPMPQAPAL  1260
WIETTAYALL HLLLHEGKAE MADQASAWLT RQGSFQGGFR STQDTVIALD ALSAYWIASH  1320
TTEERGLNVT LSSTGRNGFK SHALQLNNRQ IRGLEEELQF SLGSKINVKV GGNSKGTLKV  1380
LRTYNVLDMK NTTCQDLQIE VTVKGHVEYT MEANEDYEDY EYDELPAKDD PDAPLQPVTP  1440
LQLFEGRRNR RRREAPKVVE EQESRVHYTV CIWRNGKVGL SGMAIADVTL LSGFHALRAD  1500
LEKLTSLSDR YVSHFETEGP HVLLYFDSVP TSRECVGFEA VQEVPVGLVQ PASATLYDYY  1560
NPERRCSVFY GAPSKSRLLA TLCSAEVCQC AEGKCPRQRR ALERGLQDED GYRMKFACYY  1620
PRVEYGFQVK VLREDSRAAF RLFETKITQV LHFTKDVKAA ANQMRNFLVR ASCRLRLEPG  1680
KEYLIMGLDG ATYDLEGHPQ YLLDSNSWIE EMPSERLCRS TRQRAACAQL NDFLQEYGTQ  1740
GCQV                                                              1744

SEQ ID NO: 12           moltype = AA  length = 934
FEATURE                 Location/Qualifiers
```

-continued

```
source                  1..934
                        mol_type = protein
                        organism = synthetic construct
CARBOHYD                324
                        note = N is linked to Hex(5)HexNAc(2)Fuc(0)NeuAc(0)
CARBOHYD                324
                        note = N is linked to Hex(5)HexNAc(4)Fuc(0)NeuAc(0)
SEQUENCE: 12
MARRSVLYFI LLNALINKGQ ACFCDHYAWT QWTSCSKTCN SGTQSRHRQI VVDKYYQENF    60
CEQICSKQET RECNWQRCPI NCLLGDFGPW SDCDPCIEKQ SKVRSVLRPS QFGGQPCTAP   120
LVAFQPCIPS KLCKIEEADC KNKFRCDSGR CIARKLECNG ENDCGDNSDE RDCGRTKAVC   180
TRKYNPIPSV QLMGNGFHFL AGEPRGEVLD NSFTGGICKT VKSSRTSNPY RVPANLENVG   240
FEVQTAEDDL KTDFYKDLTS LGHNENQQGS FSSQGGSSFS VPIFYSSKRS ENINHNSAFK   300
QAIQASHKKD SSFIRIHKVM KVLNFTTKAK DLHLSDVFLK ALNHLPLEYN SALYSRIFDD   360
FGTHYFTSGS LGGVYDLLYQ FSSEELKNSG LTEEEAKHCV RIETKKRVLF AKKTKVEHRC   420
TTNKLSEKHE GSFIQGAEKS ISLIRGGRSE YGAALAWEKG SSGLEEKTFS EWLESVKENP   480
AVIDFELAPI VDLVRNIPCA VTKRNNLRKA LQEYAAKFDP CQCAPCPNNG RPTLSGTECL   540
CVCQSGTYGE NCEKQSPDYK SNAVDGQWGC WSSWSTCDAT YKRSRTRECN NPAPQRGGKR   600
CEGEKRQEED CTFSIMENNG QPCINDDEEM KEVDLPEIEA DSGCPQPVPP ENGFIRNEKQ   660
LYLVGEDVEI SCLTGFETVG YQYFRCLPDG TWRQGDVECQ RTECIKPVVQ EVLTITPFQR   720
LYRIGESIEL TCPKGFVVAG PSRYTCQGNS WTPPISNSLT CEKDTLTKLK GHCQLGKQS    780
GSECICMSPE EDCHHSEDL CVFDTDSNDY FTSPACKFKA EKCLNNQQLH FLHIGSCQDG    840
RQLEWGLERT RLSSNSTKKE SCGYDTCYDW EKCSASTSKC VCLLPPQCFK GGNQLYCVKM   900
GSSTSEKTLN ICEVGTIRCA NRKMEILHPG KCLA                              934

SEQ ID NO: 13           moltype = AA   length = 584
FEATURE                 Location/Qualifiers
source                  1..584
                        mol_type = protein
                        organism = synthetic construct
CARBOHYD                437
                        note = N is linked to Hex(5)HexNAc(2)Fuc(0)NeuAc(0)
CARBOHYD                437
                        note = N is linked to Hex(5)HexNAc(4)Fuc(1)NeuAc(0)
SEQUENCE: 13
MFAVVFFILS LMTCQPGVTA QEKVNQRVRR AATPAAVTCQ LSNWSEWTDC FPCQDKKYRH    60
RSLLQPNKFG GTICSGDIWD QASCSSSTTC VRQAQCGQDF QCKETGRCLK RHLVCNGDQD   120
CLDGSDEDDC EDVRAIDEDC SQYEPIPGSQ KAALGYNILT QEDAQSVYDA SYYGGQCETV   180
YNGEWRELRY DSTCERLYYG DDEKYFRKPY NFLKYHFEAL ADTGISSEFY DNANDLLSKV   240
KKDKSDSFGV TIGIGPAGSP LLVGVGVSHS QDTSFLNELN KYNEKKFIFT RIFTKVQTAH   300
FKMRKDDIML DEGMLQSLME LPDQYNYGMY AKFINDYGTH YITSGSMGGI YEYILVDKA    360
KMESLGITSR DITTCFGGSL GIQYEDKINV GGGLSGDHCK KFGGGKTERA RKAMAVEDII   420
SRVRGGSSGW SGGLAQNRST ITYRSWGRSL KYNPVVIDFE MQPIHEVLRH TSLGPLEAKR   480
QNLRRALDQY LMEFNACRCG PCFNNGVPIL EGTSCRCQCR LGSLGAACEQ TQTEGAKADG   540
SWSCWSSWSV CRAGIQERRR ECDNPAPQNG GASCPGRKVQ TQAC                   584

SEQ ID NO: 14           moltype = AA   length = 406
FEATURE                 Location/Qualifiers
source                  1..406
                        mol_type = protein
                        organism = synthetic construct
CARBOHYD                207
                        note = N is linked to Hex(5)HexNAc(4)Fuc(0)NeuAc(1)
CARBOHYD                211
                        note = N is linked to Hex(5)HexNAc(4)Fuc(0)NeuAc(2)
CARBOHYD                207
                        note = N is linked to Hex(6)HexNAc(5)Fuc(0)NeuAc(2)
CARBOHYD                207
                        note = N is linked to Hex(6)HexNAc(5)Fuc(0)NeuAc(3)
CARBOHYD                211
                        note = N is linked to Hex(6)HexNAc(5)Fuc(0)NeuAc(2)
CARBOHYD                241
                        note = N is linked to Hex(5)HexNAc(4)Fuc(0)NeuAc(1)
CARBOHYD                241
                        note = N is linked to Hex(5)HexNAc(4)Fuc(0)NeuAc(2)
CARBOHYD                241
                        note = N is linked to Hex(5)HexNAc(5)Fuc(1)NeuAc(1)
CARBOHYD                241
                        note = N is linked to Hex(6)HexNAc(5)Fuc(0)NeuAc(2)
SEQUENCE: 14
MSALGAVIAL LLWGQLFAVD SGNDVTDIAD DGCPKPPEIA HGYVEHSVRY QCKNYYKLRT    60
EGDGVYTLND KKQWINKAVG DKLPECEADD GCPKPPEIAH GYVEHSVRYQ CKNYYKLRTE   120
GDGVYTLNNE KKQWINKAVGD KLPECEAVCG KPKNPANPVQ RILGGHLDAK GSFPWQAKMV  180
SHHNLTTGAT LINEQWLLTT AKNLFLNHSE NATAKDIAPT LTLYVGKKQL VEIEKVVLHP   240
NYSQVDIGLI KLKQKVSVNE RVMPICLPSK DYAEVGRVGY VSGWGRNANF KFTDHLKYVM   300
LPVADQDQCI RHYEGSTVPE KKTPKSPVGV QPILNEHTFC AGMSKYQEDT CYGDAGSAFA   360
VHDLEEDTWY ATGILSFDKS CAVAEYGVYV KVTSIQDWVQ KTIAEN                 406

SEQ ID NO: 15           moltype = AA   length = 340
```

```
FEATURE             Location/Qualifiers
source              1..340
                    mol_type = protein
                    organism = synthetic construct
CARBOHYD            205
                    note = N is linked to Hex(5)HexNAc(5)Fuc(1)NeuAc(0)
SEQUENCE: 15
ASPTSPKVFP LSLDSTPQDG NVVVACLVQG FFPQEPLSVT WSESGQNVTA RNFPPSQDAS    60
GDLYTTSSQL TLPATQCPDG KSVTCHVKHY TNSSQDVTVP CRVPPPPPCC HPRLSLHRPA  120
LEDLLLGSEA NLTCTLTGLR DASGATFTWT PSSGKSAVQG PPERDLCGCY SVSSVLPGCA  180
QPWNHGETFT CTAAHPELKT PLTANITKSG NTFRPEVHLL PPPSEELALN ELVTLTCLAR  240
GFSPKDVLVR WLQGSQELPR EKYLTWASRQ EPSQGTTTYA VTSILRVAAE DWKKGETFSC  300
MVGHEALPLA FTQKTIDRMA GKPTHINVSV VMAEADGTCY                        340

SEQ ID NO: 16       moltype = AA   length = 330
FEATURE             Location/Qualifiers
source              1..330
                    mol_type = protein
                    organism = synthetic construct
CARBOHYD            180
                    note = N is linked to Hex(5)HexNAc(4)Fuc(1)NeuAc(1)
SEQUENCE: 16
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 17       moltype = AA   length = 326
FEATURE             Location/Qualifiers
source              1..326
                    mol_type = protein
                    organism = synthetic construct
CARBOHYD            176
                    note = N is linked to Hex(4)HexNAc(4)Fuc(0)NeuAc(0)
CARBOHYD            176
                    note = N is linked to Hex(4)HexNAc(4)Fuc(1)NeuAc(1)
SEQUENCE: 17
ASTKGPSVFP LAPCSRSTSE STAALGCLVK DYFPEPVTVS WNSGALTSGV HTFPAVLQSS    60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVVHQ DWLNGKEYKC KVSNKGLPAP IEKTISKTKG QPREPQVYTL PPSREEMTKN  240
QVSLTCLVKG FYPSDISVEW ESNGQPENNY KTTPPMLDSD GSFFLYSKLT VDKSRWQQGN  300
VFSCSVMHEA LHNHYTQKSL SLSPGK                                       326

SEQ ID NO: 18       moltype = AA   length = 453
FEATURE             Location/Qualifiers
source              1..453
                    mol_type = protein
                    organism = synthetic construct
CARBOHYD            209
                    note = N is linked to Hex(5)HexNAc(4)Fuc(0)NeuAc(1)
SEQUENCE: 18
GSASAPTLFP LVSCENSPSD TSSVAVGCLA QDFLPDSITF SWKYKNNSDI SSTRGFPSVL    60
RGGKYAATSQ VLLPSKDVMQ GTDEHVVCKV QHPNGNKEKN VPLPVIAELP PKVSVFVPPR  120
DGFFGNPRKS KLICQATGFS PRQIQVSWLR EGKQVGSGVT TDQVQAEAKE SGPTTYKVTS  180
TLTIKESDWL GQSMFTCRVD HRGLTFQQNA SSMCVPDQDT AIRVFAIPPS FASIFLTKST  240
KLTCLVTDLT TYDSVTISWT RQNGEAVKTH TNISESHPNA TFSAVGEASI CEDDWNSGER  300
FTCTVTHTDL PSPLKQTISR PKGVALHRPD VYLLPPAREQ LNLRESATIT CLVTGFSPAD  360
VFVQWMQRGQ PLSPEKYVTS APMPEPQAPG RYFAHSILTV SEEEWNTGET YTCVVAHEAL  420
PNRVTERTVD KSTGKPTLYN VSLVMSDTAG TCY                                453

SEQ ID NO: 19       moltype = AA   length = 638
FEATURE             Location/Qualifiers
source              1..638
                    mol_type = protein
                    organism = synthetic construct
CARBOHYD            494
                    note = N is linked to Hex(5)HexNAc(4)Fuc(0)NeuAc(1)
CARBOHYD            494
                    note = N is linked to Hex(5)HexNAc(4)Fuc(0)NeuAc(2)
CARBOHYD            494
                    note = N is linked to Hex(5)HexNAc(4)Fuc(1)NeuAc(0)
CARBOHYD            494
                    note = N is linked to Hex(6)HexNAc(5)Fuc(0)NeuAc(3)
SEQUENCE: 19
MILFKQATYF ISLFATVSCG CLTQLYENAF FRGGDVASMY TPNAQYCQMR CTFHPRCLLF    60
SFLPASSIND MEKRFGCFLK DSVTGTLPKV HRTGAVSGHS LKQCGHQISA CHRDIYKGVD  120
```

-continued

```
MRGVNFNVSK VSSVEECQKR CTNNIRCQFF SYATQTFHKA EYRNNCLLKY SPGGTPTAIK    180
VLSNVESGFS LKPCALSEIG CHMNIFQHLA FSDVDVARVL TPDAFVCRTI CTYHPNCLFF    240
TFYTNVWKIE SQRNVCLLKT SESGTPSSST PQENTISGYS LLTCKRTLPE PCHSKIYPGV    300
DFGGEELNVT FVKGVNVCQE TCTKMIRCQF FTYSLLPEDC KEEKCKCFLR LSMDGSPTRI    360
AYGTQGSSGY SLRLCNTGDN SVCTTKTSTR IVGGTNSSWG EWPWQVSLQV KLTAQRHLCG    420
GSLIGHQWVL TAAHCFDGLP LQDVWRIYSG ILNLSDITKD TPFSQIKEII IHQNYKVSEG    480
NHDIALIKLQ APLNYTEFQK PICLPSKGDT STIYTNCWVT GWGFSKEKGE IQNILQKVNI    540
PLVTNEECQK RYQDYKITQR MVCAGYKEGG KDACKGDSGG PLVCKHNGMW RLVGITSWGE    600
GCARREQPGV YTKVAEYMDW ILEKTQSSDG KAQMQSPA                            638

SEQ ID NO: 20              moltype = AA  length = 698
FEATURE                    Location/Qualifiers
source                     1..698
                           mol_type = protein
                           organism = synthetic construct
CARBOHYD                   432
                           note = N is linked to Hex(5)HexNAc(4)Fuc(0)NeuAc(2)
CARBOHYD                   432
                           note = N is linked to Hex(6)HexNAc(5)Fuc(0)NeuAc(1)
CARBOHYD                   432
                           note = N is linked to Hex(6)HexNAc(5)Fuc(0)NeuAc(2)
SEQUENCE: 20
MRLAVGALLV CAVLGLCLAV PDKTVRWCAV SEHEATKCQS FRDHMKSVIP SDGPSVACVK     60
KASYLDCIRA IAANEADAVT LDAGLVYDAY LAPNNLKPVV AEFYGSKEDP QTFYYAVAVV    120
KKDSGFQMNQ LRGKKSCHTG LGRSAGWNIP IGLLYCDLPE PRKPLEKAVA NFFSGSCAPC    180
ADGTDFPQLC QLCPGCGCST LNQYFGYSGA FKCLKDGAGD VAPVKHSTIF ENLANKADRD    240
QYELLCLDNT RKPVDEYKDC HLAQVPSHTV VARSMGGKED LIWELLNQAQ EHFGKDKSKE    300
FQLFSSPHGK DLLFKDSAHG FLKVPPRMDA KMYLGYEYVT AIRNLREGTC PEAPTDECKP    360
VKWCALSHHE RLKCDEWSVN SVGKIECVSA ETTEDCIAKI MNGEADAMSL DGGFVYIAGK    420
CGLVPVLAEN YNKSDNCEDT PEAGYFAIAV VKKSASDLTW DNLKGKKSCH TAVGRTAGWN    480
IPMGLLYNKI NHCRFDEFFS EGCAPGSKKD SSLCKLCMGS GLNLCEPNNK EGYYGYTGAF    540
RCLVEKGDVA FVKHQTVPQN TGGKNPDPWA KNLNEKDYEL LCLDGTRKPV EEYANCHLAR    600
APNHAVVTRK DKEACVHKIL RQQQHLFGSN VTDCSGNFCL FRSETKDLLF RDDTVCLAKL    660
HDRNTYEKYL GEEYVKAVGN LRKCSTSSLL EACTFRRP                            698

SEQ ID NO: 21              moltype = AA  length = 478
FEATURE                    Location/Qualifiers
source                     1..478
                           mol_type = protein
                           organism = synthetic construct
CARBOHYD                   169
                           note = N is linked to Hex(5)HexNAc(4)Fuc(0)NeuAc(1)
SEQUENCE: 21
MAPLRPLLIL ALLAWVALAD QESCKGRCTE GFNVDKKCQC DELCSYYQSC CTDYTAECKP     60
QVTRGDVFTM PEDEYTVYDD GEEKNNATVH EQVGGPSLTS DLQAQSKGNP EQTPVLKPEE    120
EAPAPEVGAS KPEGIDSRPE TLHPGRPQPP AEEELCSGKP FDAFTDLKNG SLFAFRGQYC    180
YELDEKAVRP GYPKLIRDVW GIEGPIDAAF TRINCQGKTY LFKGSQYWRF EDGVLDPDYP    240
RNISDGFDGI PDNVDAALAL PAHSYSGRER VYFFKGKQYW EYQFQHQPSQ EECEGSSLSA    300
VFEHFAMMQR DSWEDIFELL FWGRTSAGTR QPQFISRDWH GVPGQVDAAM AGRIYISGMA    360
PRPSLAKKQR FRHRNRKGYR SQRGHSRGRN QNSRRPSRAT WLSLFSSEES NLGANNYDDY    420
RMDWLVPATC EPIQSVFFFS GDKYYRVNLR TRRVDTVDPP YPRSIAQYWL GCPAPGHL      478

SEQ ID NO: 22              moltype = AA  length = 298
FEATURE                    Location/Qualifiers
source                     1..298
                           mol_type = protein
                           organism = synthetic construct
CARBOHYD                   112
                           note = N is linked to Hex(5)HexNAc(4)Fuc(0)NeuAc(2)
SEQUENCE: 22
MVRMVPVLLS LLLLLGPAVP QENQDGRYSL TYIYTGLSKH VEDVPAFQAL GSLNDLQFFR     60
YNSKDRKSQP MGLWRQVEGM EDWKQDSQLQ KAREDIFMET LKDIVEYYND SNGSHVLQGR    120
FGCEIENNRS SGAFWKYYYD GKDYIEFNKE IPAWVPFDPA AQITKQKWEA EPVYVQRAKA    180
YLEEECPATL RKYLKYSKNI LDRQDPPSVV VTSHQAPGEK KKLKCLAYDF YPGKIDVHWT    240
RAGEVQEPEL RGDVLHNGNG TYQSWVVVAV PPQDTAPYSC HVQHSSLAQP LVVPWEAS      298

SEQ ID NO: 23              moltype = AA  length = 16
FEATURE                    Location/Qualifiers
source                     1..16
                           mol_type = protein
                           organism = synthetic construct
CARBOHYD                   4
                           note = N is linked to Hex(5)HexNAc(4)Fuc(0)NeuAc(1)
CARBOHYD                   4
                           note = N is linked to Hex(5)HexNAc(4)Fuc(0)NeuAc(2)
SEQUENCE: 23
YLGNATAIFF LPDEGK                                                     16

SEQ ID NO: 24              moltype = AA  length = 33
```

```
FEATURE                 Location/Qualifiers
source                  1..33
                        mol_type = protein
                        organism = synthetic construct
CARBOHYD                27
                        note = N is linked to Hex(5)HexNAc(4)Fuc(0)NeuAc(2)
SEQUENCE: 24
EGDHEFLEVP EAQEDVEATF PVHQPGNYSC SYR                              33

SEQ ID NO: 25           moltype = AA  length = 11
FEATURE                 Location/Qualifiers
source                  1..11
                        mol_type = protein
                        organism = synthetic construct
SEQUENCE: 25
AIGYLNTGYQ R                                                     11

SEQ ID NO: 26           moltype = AA  length = 14
FEATURE                 Location/Qualifiers
source                  1..14
                        mol_type = protein
                        organism = synthetic construct
SEQUENCE: 26
TEHPFTVEEF VLPK                                                  14

SEQ ID NO: 27           moltype = AA  length = 19
FEATURE                 Location/Qualifiers
source                  1..19
                        mol_type = protein
                        organism = synthetic construct
CARBOHYD                3
                        note = N is linked to Hex(5)HexNAc(4)Fuc(0)NeuAc(2)
SEQUENCE: 27
VSNQTLSLFF TVLQDVPVR                                             19

SEQ ID NO: 28           moltype = AA  length = 33
FEATURE                 Location/Qualifiers
source                  1..33
                        mol_type = protein
                        organism = synthetic construct
CARBOHYD                10
                        note = N is linked to Hex(5)HexNAc(2)Fuc(0)NeuAc(0)
CARBOHYD                10
                        note = N is linked to Hex(5)HexNAc(4)Fuc(0)NeuAc(1)
CARBOHYD                10
                        note = N is linked to Hex(5)HexNAc(4)Fuc(0)NeuAc(2)
SEQUENCE: 28
IITILEEEMN VSVCGLYTYG KPVPGHVTVS ICR                              33

SEQ ID NO: 29           moltype = AA  length = 22
FEATURE                 Location/Qualifiers
source                  1..22
                        mol_type = protein
                        organism = synthetic construct
CARBOHYD                9
                        note = N is linked to Hex(5)HexNAc(4)Fuc(0)NeuAc(2)
CARBOHYD                9
                        note = N is linked to Hex(5)HexNAc(4)Fuc(1)NeuAc(1)
CARBOHYD                9
                        note = N is linked to Hex(5)HexNAc(4)Fuc(1)NeuAc(2)
SEQUENCE: 29
GCVLLSYLNE TVTVSASLES VR                                         22

SEQ ID NO: 30           moltype = AA  length = 32
FEATURE                 Location/Qualifiers
source                  1..32
                        mol_type = protein
                        organism = synthetic construct
CARBOHYD                6
                        note = N is linked to Hex(5)HexNAc(2)Fuc(0)NeuAc(0)
CARBOHYD                6
                        note = N is linked to Hex(6)HexNAc(2)Fuc(0)NeuAc(0)
CARBOHYD                6
                        note = N is linked to Hex(6)HexNAc(3)Fuc(0)NeuAc(0)
SEQUENCE: 30
SLGNVNFTVS AEALESQELC GTEVPSVPEH GR                               32

SEQ ID NO: 31           moltype = AA  length = 56
FEATURE                 Location/Qualifiers
```

```
source                         1..56
                               mol_type = protein
                               organism = synthetic construct
CARBOHYD                       46
                               note = N is linked to Hex(5)HexNAc(4)Fuc(0)NeuAc(2)
SEQUENCE: 31
ASVSVLGDIL GSAMQNTQNL LQMPYGCGEQ NMVLFAPNIY VLDYLNETQQ LTPEIK            56

SEQ ID NO: 32                  moltype = AA  length = 20
FEATURE                        Location/Qualifiers
source                         1..20
                               mol_type = protein
                               organism = synthetic construct
CARBOHYD                       2
                               note = N is linked to Hex(7)HexNAc(6)Fuc(0)NeuAc(4)
SEQUENCE: 32
FNLTETSEAE IHQSFQHLLR                                                    20

SEQ ID NO: 33                  moltype = AA  length = 10
FEATURE                        Location/Qualifiers
source                         1..10
                               mol_type = protein
                               organism = synthetic construct
CARBOHYD                       6
                               note = N is linked to Hex(5)HexNAc(4)Fuc(0)NeuAc(2)
SEQUENCE: 33
DIENFNSTQK                                                               10

SEQ ID NO: 34                  moltype = AA  length = 24
FEATURE                        Location/Qualifiers
source                         1..24
                               mol_type = protein
                               organism = synthetic construct
CARBOHYD                       15
                               note = N is linked to Hex(5)HexNAc(4)Fuc(0)NeuAc(2)
SEQUENCE: 34
QIPLCANLVP VPITNATLDQ ITGK                                               24

SEQ ID NO: 35                  moltype = AA  length = 15
FEATURE                        Location/Qualifiers
source                         1..15
                               mol_type = protein
                               organism = synthetic construct
CARBOHYD                       7
                               note = N is linked to Hex(6)HexNAc(5)Fuc(0)NeuAc(2)
SEQUENCE: 35
QDQCIYNTTY LNVQR                                                         15

SEQ ID NO: 36                  moltype = AA  length = 19
FEATURE                        Location/Qualifiers
source                         1..19
                               mol_type = protein
                               organism = synthetic construct
CARBOHYD                       14
                               note = T is linked to Hex(1)HexNAc(1)Fuc(0)NeuAc(2)
CARBOHYD                       14
                               note = T is linked to Hex(1)HexNAc(2)Fuc(0)NeuAc(2)
CARBOHYD                       14
                               note = T is linked to Hex(1)HexNAc(3)Fuc(0)NeuAc(0)
CARBOHYD                       14
                               note = T is linked to Hex(2)HexNAc(1)Fuc(1)NeuAc(0)
SEQUENCE: 36
FSEFWDLDPE VRPTSAVAA                                                     19

SEQ ID NO: 37                  moltype = AA  length = 23
FEATURE                        Location/Qualifiers
source                         1..23
                               mol_type = protein
                               organism = synthetic construct
CARBOHYD                       15
                               note = N is linked to Hex(5)HexNAc(4)Fuc(2)NeuAc(1)
SEQUENCE: 37
TELFSSSCPG GIMLNETGQG YQR                                                23

SEQ ID NO: 38                  moltype = AA  length = 10
FEATURE                        Location/Qualifiers
source                         1..10
                               mol_type = protein
                               organism = synthetic construct
```

```
CARBOHYD                      1
                              note = N is linked to Hex(5)HexNAc(4)Fuc(0)NeuAc(1)
SEQUENCE: 38
NGTAVCATNR                                                                    10

SEQ ID NO: 39                 moltype = AA  length = 14
FEATURE                       Location/Qualifiers
source                        1..14
                              mol_type = protein
                              organism = synthetic construct
CARBOHYD                      3
                              note = N is linked to Hex(6)HexNAc(5)Fuc(0)NeuAc(1)
SEQUENCE: 39
LANLTQGEDQ YYLR                                                               14

SEQ ID NO: 40                 moltype = AA  length = 11
FEATURE                       Location/Qualifiers
source                        1..11
                              mol_type = protein
                              organism = synthetic construct
CARBOHYD                      3
                              note = N is linked to Hex(5)HexNAc(4)Fuc(0)NeuAc(2)
SEQUENCE: 40
GLNVTLSSTG R                                                                  11

SEQ ID NO: 41                 moltype = AA  length = 7
FEATURE                       Location/Qualifiers
source                        1..7
                              mol_type = protein
                              organism = synthetic construct
CARBOHYD                      3
                              note = N is linked to Hex(5)HexNAc(2)Fuc(0)NeuAc(0)
CARBOHYD                      3
                              note = N is linked to Hex(5)HexNAc(4)Fuc(0)NeuAc(0)
SEQUENCE: 41
VLNFTTK                                                                        7

SEQ ID NO: 42                 moltype = AA  length = 14
FEATURE                       Location/Qualifiers
source                        1..14
                              mol_type = protein
                              organism = synthetic construct
CARBOHYD                      13
                              note = N is linked to Hex(5)HexNAc(2)Fuc(0)NeuAc(0)
CARBOHYD                      13
                              note = N is linked to Hex(5)HexNAc(4)Fuc(1)NeuAc(0)
SEQUENCE: 42
GGSSGWSGGL AQNR                                                               14

SEQ ID NO: 43                 moltype = AA  length = 13
FEATURE                       Location/Qualifiers
source                        1..13
                              mol_type = protein
                              organism = synthetic construct
CARBOHYD                      5
                              note = N is linked to Hex(5)HexNAc(4)Fuc(0)NeuAc(1)
CARBOHYD                      9
                              note = N is linked to Hex(5)HexNAc(4)Fuc(0)NeuAc(2)
CARBOHYD                      5
                              note = N is linked to Hex(6)HexNAc(5)Fuc(0)NeuAc(2)
CARBOHYD                      5
                              note = N is linked to Hex(6)HexNAc(5)Fuc(0)NeuAc(3)
CARBOHYD                      9
                              note = N is linked to Hex(6)HexNAc(5)Fuc(0)NeuAc(2)
SEQUENCE: 43
NLFLNHSENA TAK                                                                13

SEQ ID NO: 44                 moltype = AA  length = 16
FEATURE                       Location/Qualifiers
source                        1..16
                              mol_type = protein
                              organism = synthetic construct
CARBOHYD                      6
                              note = N is linked to Hex(5)HexNAc(4)Fuc(0)NeuAc(1)
CARBOHYD                      6
                              note = N is linked to Hex(5)HexNAc(4)Fuc(0)NeuAc(2)
CARBOHYD                      6
                              note = N is linked to Hex(5)HexNAc(5)Fuc(1)NeuAc(1)
CARBOHYD                      6
```

-continued

```
                        note = N is linked to Hex(6)HexNAc(5)Fuc(0)NeuAc(2)
SEQUENCE: 44
VVLHPNYSQV DIGLIK                                               16

SEQ ID NO: 45           moltype = AA   length = 9
FEATURE                 Location/Qualifiers
source                  1..9
                        mol_type = protein
                        organism = synthetic construct
CARBOHYD                6
                        note = N is linked to Hex(5)HexNAc(5)Fuc(1)NeuAc(0)
SEQUENCE: 45
TPLTANITK                                                       9

SEQ ID NO: 46           moltype = AA   length = 9
FEATURE                 Location/Qualifiers
source                  1..9
                        mol_type = protein
                        organism = synthetic construct
CARBOHYD                5
                        note = N is linked to Hex(5)HexNAc(4)Fuc(1)NeuAc(1)
SEQUENCE: 46
EEQYNSTYR                                                       9

SEQ ID NO: 47           moltype = AA   length = 9
FEATURE                 Location/Qualifiers
source                  1..9
                        mol_type = protein
                        organism = synthetic construct
CARBOHYD                5
                        note = N is linked to Hex(4)HexNAc(4)Fuc(0)NeuAc(0)
CARBOHYD                5
                        note = N is linked to Hex(4)HexNAc(4)Fuc(1)NeuAc(1)
SEQUENCE: 47
EEQFNSTFR                                                       9

SEQ ID NO: 48           moltype = AA   length = 21
FEATURE                 Location/Qualifiers
source                  1..21
                        mol_type = protein
                        organism = synthetic construct
CARBOHYD                7
                        note = N is linked to Hex(5)HexNAc(4)Fuc(0)NeuAc(1)
SEQUENCE: 48
GLTFQQNASS MCVPDQDTAI R                                         21

SEQ ID NO: 49           moltype = AA   length = 19
FEATURE                 Location/Qualifiers
source                  1..19
                        mol_type = protein
                        organism = synthetic construct
CARBOHYD                6
                        note = N is linked to Hex(5)HexNAc(4)Fuc(0)NeuAc(1)
CARBOHYD                6
                        note = N is linked to Hex(5)HexNAc(4)Fuc(0)NeuAc(2)
CARBOHYD                6
                        note = N is linked to Hex(5)HexNAc(4)Fuc(1)NeuAc(0)
CARBOHYD                6
                        note = N is linked to Hex(6)HexNAc(5)Fuc(0)NeuAc(3)
SEQUENCE: 49
LQAPLNYTEF QKPICLPSK                                            19

SEQ ID NO: 50           moltype = AA   length = 13
FEATURE                 Location/Qualifiers
source                  1..13
                        mol_type = protein
                        organism = synthetic construct
CARBOHYD                12
                        note = N is linked to Hex(5)HexNAc(4)Fuc(0)NeuAc(2)
CARBOHYD                12
                        note = N is linked to Hex(6)HexNAc(5)Fuc(0)NeuAc(1)
CARBOHYD                12
                        note = N is linked to Hex(6)HexNAc(5)Fuc(0)NeuAc(2)
SEQUENCE: 50
CGLVPVLAEN YNK                                                  13

SEQ ID NO: 51           moltype = AA   length = 8
FEATURE                 Location/Qualifiers
source                  1..8
```

```
                          mol_type = protein
                          organism = synthetic construct
CARBOHYD                  1
                          note = N is linked to Hex(5)HexNAc(4)Fuc(0)NeuAc(1)
SEQUENCE: 51
NGSLFAFR                                                                    8

SEQ ID NO: 52             moltype = AA  length = 18
FEATURE                   Location/Qualifiers
source                    1..18
                          mol_type = protein
                          organism = synthetic construct
CARBOHYD                  10
                          note = N is linked to Hex(5)HexNAc(4)Fuc(0)NeuAc(2)
SEQUENCE: 52
DIVEYYNDSN GSHVLQGR                                                        18

SEQ ID NO: 53             moltype = AA  length = 7
FEATURE                   Location/Qualifiers
REGION                    1..7
                          note = Description of Artificial Sequence: Synthetic peptide
source                    1..7
                          mol_type = protein
                          organism = synthetic construct
SEQUENCE: 53
ECDMHYK                                                                     7

SEQ ID NO: 54             moltype = AA  length = 7
FEATURE                   Location/Qualifiers
REGION                    1..7
                          note = Description of Artificial Sequence: Synthetic peptide
MOD_RES                   2
                          note = Alkylated-Cysteine
source                    1..7
                          mol_type = protein
                          organism = synthetic construct
SEQUENCE: 54
ECDMHYK                                                                     7
```

What is claimed is:

1. A method of classifying a biological sample with respect to a plurality of states associated with fatty liver disease (FLD) progression, the method comprising:
receiving peptide structure data corresponding to a set of glycoproteins in the biological sample obtained from a subject;
inputting quantification data identified from the peptide structure data for a set of peptide structures into a machine learning model, wherein the set of peptide structures includes at least one peptide structure identified from a plurality of peptide structures in Table 5, wherein the machine learning model is a regression model;
analyzing the quantification data using the machine learning model to generate a disease indicator; and generating a diagnosis output based on the disease indicator that classifies the biological sample as evidencing a corresponding state of the plurality of states associated with the FLD progression.

2. The method of claim 1, wherein the disease indicator comprises a score and wherein generating the diagnosis output comprises:
determining that the score falls within a selected range associated with the corresponding state of the plurality of states; and
determining that the biological sample evidences the corresponding state in response to a determination that the score falls within the selected range associated with corresponding state.

3. The method of claim 1, wherein the plurality of states includes a non-alcoholic steatohepatitis (NASH) state and a hepatocellular carcinoma (HCC) state.

4. The method of claim 1, wherein the plurality of states includes a non-NASH/HCC state that comprises at least one of a healthy state, a liver disease-free state, or a benign hepatic mass state.

5. The method of claim 1, wherein the at least one peptide structure comprises a glycopeptide structure defined by a peptide sequence and a glycan structure linked to the peptide sequence at a linking site of the peptide sequence, as identified in Table 5, with the peptide sequence being one of SEQ ID NOS: 23, 24, 25, 29, 30, 31, 33, 35, 36, 37, 38, 39, 40, 41, 42, 43, 44, 45, 46, 47, 48, 49, 50, 51, or 52 as defined in Table 5.

6. The method of claim 1, wherein the quantification data for a peptide structure of the set of peptide structures comprises at least one of an abundance, a relative abundance, a normalized abundance, a relative quantity, an adjusted quantity, a normalized quantity, a relative concentration, an adjusted concentration, or a normalized concentration.

7. The method of claim 1, wherein the peptide structure data is generated using multiple reaction monitoring mass spectrometry (MRM-MS).

8. A method of detecting a presence of one of a plurality of states associated with fatty liver disease (FLD) progression in a biological sample, the method comprising:
receiving peptide structure data corresponding to a set of glycoproteins in the biological sample obtained from a subject;
analyzing the peptide structure data using a supervised machine learning model to generate a disease indicator based on at least 3 peptide structures selected from a group of peptide structures identified in Table 5, wherein the machine learning model is a regression model; and detecting the presence of a corresponding state of the plurality of states associated with the FLD progression in response to a determination that the disease indicator falls within a selected range associated with the corresponding state.

9. The method of claim 8, wherein a peptide structure of the at least 3 peptide structures comprises a glycopeptide structure defined by a peptide sequence and a glycan structure linked to the peptide sequence at a linking site of the peptide sequence, as identified in Table 5, with the peptide sequence being one of SEQ ID NOS: 23, 24, 25, 29, 30, 31, 33, 35, 36, 37, 38, 39, 40, 41, 42, 43, 44, 45, 46, 47, 48, 49, 50, 52, or 52 as defined in Table 5.

10. The method of claim 8, wherein the supervised machine learning model comprises a logistic regression model.

11. The method of claim 8, wherein the supervised machine learning model comprises a penalized multivariable logistic regression model.

12. The method of claim 8, wherein the peptide structure data comprises quantification data, the quantification data for a peptide structure of the group of peptide structures comprising at least one of an abundance, a relative abundance, a normalized abundance, a relative quantity, an adjusted quantity, a normalized quantity, a relative concentration, an adjusted concentration, or a normalized concentration.

13. The method of claim 8, wherein the disease indicator is a probability score.

14. The method of claim 8, further comprising:
generating a report that includes a diagnosis based on the corresponding state detected for the subject.

15. The method of claim 8, wherein the plurality of states includes at least two selected from a group consisting of a non-alcoholic steatohepatitis (NASH) state, a hepatocellular carcinoma (HCC) state, and a non-NASH/HCC state.

16. The method of claim 1, wherein the regression model comprises a LASSO model, or a LASSO regularization model.

17. The method of claim 16, wherein the regression model is trained to compute a disease indicator or identify weight coefficients for peptide structures of a set of peptide structures.

18. The method of claim 8, wherein the regression model is a LASSO model, or a LASSO regularization model.

19. The method of claim 18, wherein the regression model is trained to compute a disease indicator or identify weight coefficients for peptide structures of a set of peptide structures.

* * * * *